(12) United States Patent
Kim et al.

(10) Patent No.: US 7,824,373 B2
(45) Date of Patent: Nov. 2, 2010

(54) SELF-CONTAINED POWER-ASSISTED SYRINGE

(76) Inventors: Ducksoo Kim, 9 Ceder Hill Rd., Dover, MA (US) 02030; Joseph L. Smith, Jr., 113 Oak Rd., Concord, MA (US) 01742; James A. Crunkleton, 46 Sunset Rd., Weston, MA (US) 02493

( * ) Notice: Subject to any disclaimer, the term of this patent is extended or adjusted under 35 U.S.C. 154(b) by 1859 days.

(21) Appl. No.: 10/848,714

(22) Filed: May 19, 2004

(65) Prior Publication Data

US 2005/0070848 A1 Mar. 31, 2005

Related U.S. Application Data

(60) Provisional application No. 60/473,739, filed on May 28, 2003.

(51) Int. Cl.
*A61M 37/00* (2006.01)
(52) U.S. Cl. .................. 604/141; 604/140; 604/146

(58) Field of Classification Search ......... 604/140–146, 604/68–70, 93.01, 131–135, 181, 187, 207, 604/208
See application file for complete search history.

(56) References Cited

U.S. PATENT DOCUMENTS 2,605,763 A * 8/1952 Smoot .................. 604/70

* cited by examiner

*Primary Examiner*—Kevin C. Sirmons
*Assistant Examiner*—Phillip Gray
(74) *Attorney, Agent, or Firm*—David Prashker

(57) ABSTRACT

A self-contained and hand-held power-assisted syringe is provided which is suitable for the controlled injection of fluid material during medical procedures such as coronary angiography procedures which utilize small-bore and small sized guide catheter systems. The present invention provides a greater degree of injection power on-demand than was previously possible in a portable and hand-held syringe; and it can deliver larger volumes of radiopaque contrast medium at greater pressures than was previously possible using a conventional manual syringe. The power assisted syringe, along with all components necessary for its effective use and operation, may be pre-packaged and steriled within a single container and then disposed of after use.

18 Claims, 33 Drawing Sheets

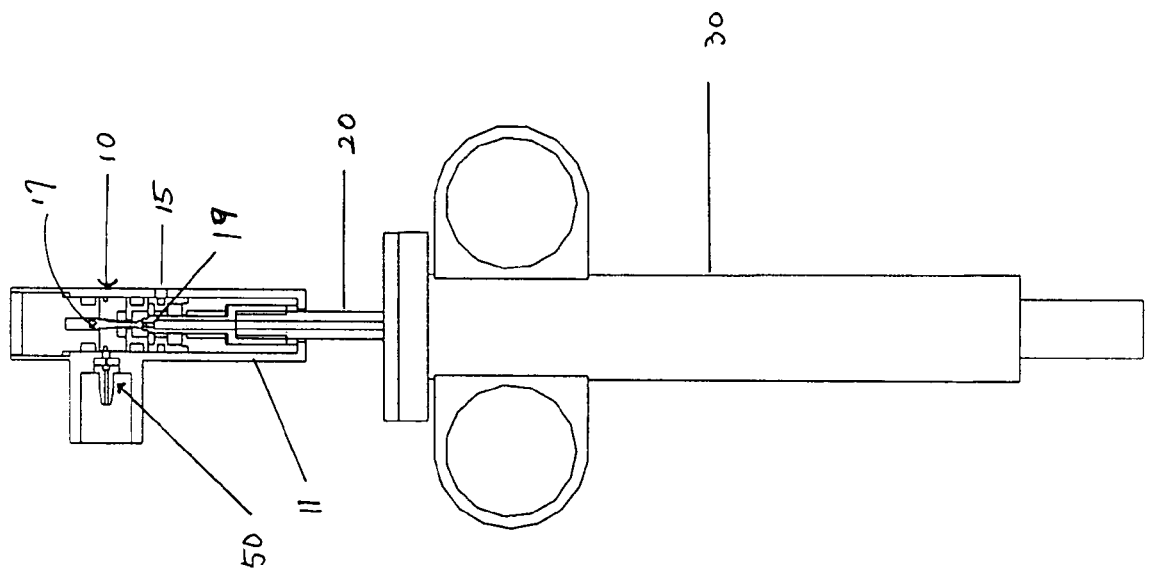

SELF-CONTAINED POWER-ASSISTED SYRINGE

PRIORITY CLAIM

The present invention was first filed as U.S. Provisional Patent Application Ser. No. 60/473,739 on May 28, 2003.

FIELD OF THE INVENTION

The present invention is directed to the field of medical devices and more particularly to an integrated, hand-held power assist syringe device and its uses.

BACKGROUND OF THE INVENTION

Cardiovascular disease is the leading cause of death in the United States, and approximately one million people die of it annually. For this reason, contrast angiography is today an integral part in the diagnosis and treatment of cardiovascular disease. In the year 2000, U.S. cardiologists performed approximately two million diagnostic and therapeutic angiographic procedures according to data from Health Resources Utilization Branch of Center for Disease Control and Prevention/National Center for Health Statistics.

Also, despite recent advances in non-invasive imaging techniques, angiography remains the gold standard for diagnosis of vascular disease. Angiography as a technique involves the placement of a catheter (a thin plastic tube) into a major blood vessel or the heart (catheterization) through another artery or vein found either in the groin or arm (typically the femoral or radial artery respectively). During angiography, the proximal end of the catheter is connected to either a hand-held syringe or an electrically powered injector; and a radiopaque dye (a contrast medium containing iodine) is injected through the catheter in order to make the blood vessels visible on x-ray images (angiogram) and/or fluoroscopic pictures (or moving x-rays).

Throughout the procedure, injections of contrast medium are repeatedly made in varying volumes (usually 1 to 10 cc/sec) and with varying durations of injection (typically 1 to 5 seconds). The resulting angiogram is obtained solely for diagnostic purposes; and is routinely used during a subsequently performed interventional procedure such as angioplasty or stenting—where a balloon is inserted into the blood vessels and inflated to open a stenosis caused by atherosclerotic plaque buildup. Frequent intermittent injections of the radiopaque contrast medium is required during each of these diagnostic and interventional procedures to obtain various views of the blood vessels and for optimal positioning of catheters, guidewires, balloons and stents at the targeted vessels. Traditionally also, coronary angiography has been performed using a disposable manual syringe attached to a manifold system.

The Commonly Occurring Complications of Catheterization:

Once the dye injection procedures are complete, the catheter is slowly and carefully removed from the blood vessel (or heart); and manual compression is applied over the puncture site for 15 minutes, followed by bed rest for 4-6 hours, in order for blood clotting to take place and the arterial or veinal puncture to reseal itself (hemostasis).

Sometimes however, serious complications take place and occur even during simple diagnostic catheterization procedures. Such major complications include (1) formation of pseudoaneurysm (i.e., formation of a cavity of blood around the artery by continuous leakage of blood through the hole due to failure of spontaneous closure of the puncture hole); (2) creation of a hematoma or pseudoaneurysm formation large enough to compress the adjacent nerves causes paralysis of the leg; and (3) continuous bleeding into the free body spaces (such as the pelvic cavity, abdominal cavity or retroperitoneal space) which can cause rapid loss of blood and subsequent hypotensive shock.

These kinds of major complications are known to be closely related to the size of the puncture hole on the access blood vessels, i.e. the size of the catheters. Therefore, interventional procedures, such as coronary angioplasty, are far more likely to produce major complications at the catheter insertion site of the arteries than diagnostic catheterization procedures, owing to the use of larger sized catheters. These complications occur even after a long duration of direct compression time (10 to 60 minutes) upon removal of the catheter from the patient. Also, a long manual compression time period is inconvenient for the attending physicians and, equally important, can be very painful to the patient. For these reasons, the use of larger sized catheters for coronary angiography (CA) has been generally and routinely discouraged.

The recent technological advances in the manufacture of catheters having a smaller outer diameter and a larger inner diameter (such as 4 French diagnostic catheters) and the availability of lower profile balloons and stents have made it feasible to perform coronary procedures with smaller sized guiding catheters. In interventional procedures, the use of smaller sized guiding catheters (for example, 6 Fr) helps avoid the problems and complications described above with respect to large catheters, and most notably reduces the incidence of access site complications. [See for example: Pande et al., "Coronary Angiography With Four French Catheters", *Am J Cardiol*, 1992, 70 (11):1085-1086; Nasser et al., "Peripheral Vascular Complications Following Coronary Interventional Procedures", *Clin Cardiol*, 1995; 18:609-614; Muller et al., *Am J Cardiol* 1992; 69:63-68; Davis et al., *Heart Lung*, 1997, 26:119-127; and Metz et al., *Am Heart J*, 1997, 134:131-137].

Conventional Manually Operated Syringes:

The conventional, manually operated syringe (typically 10-12 cc in fluid containing capacity) is in common use and has been adequate for injection of radiopaque contrast medium through the relatively large-bore catheters which range in size from about 6-7 French for diagnostic procedures or from 7-8 French guiding catheter for interventional procedures. The manual syringes conventionally used for the injection of contrast medium are typically made of various plastics such as polypropylene and polycarbonate. These syringes include a barrel having a liquid discharge opening at one end, and a nozzle through which the contrast medium of choice is ejected. The act of fluid ejection is effected by means of a plunger which has a displaceable piston at the distal end of the barrel; and the body of the syringe has either a ring or a grip at the proximal end which can be held by the user's index and third fingers. The displaceable piston can then be actuated by the user's thumb in a forward and backward motion made in response to the coordinated movement of the operator's hand and fingers at the proximal end of the barrel.

As is apparent, an adequate pressure force is needed to operate a syringe. A non-human driving mechanism, such as an electrical motor, provides this quantity of pressure force in automated syringes. Many syringes, however, are operated using only the manual force generated by a human hand. Although typically less sophisticated than automated syringes, manually operated syringes continue to be widely used because they are inexpensive; are easy to use; are disposable; offer excellent operator control; and do not require complex and bulky driving mechanisms.

Pressure Force Problems of Manual Syringes:

One of the disadvantages in performing angiography using a smaller sized diagnostic catheter (such as a 4 to 5 French catheter) and a guiding catheter (such as a 6 French catheter) coaxially and for internally carrying hardware (such as balloon catheter or stent to be positioned inside a blood vessel) is that much higher injection pressures are required to introduce adequate quantities of radiopaque fluids and to produce adequate opacification of coronary flow. For example, force pressures in the range of 300 to 500 psi are needed for delivery of x-ray dye at a rate of 3 to 5 cc/sec for small sized catheters in comparison to a pressure force of less than 150 psi with larger sized catheters. [See Danzi et al., "A Randomized Comparison Of The Use Of 4 And 6 French Diagnostic Catheters And The Limits Of Downsizing", Int J Cardiol, 2001, 80(1):5-6; Resar et al, "Percutaneous Transluminal Coronary Angioplasty Through 6 F Diagnostic Catheters: A Feasibility Study", Am Heart J, 1993, 125(6):1591-1596; Saito et al, "Evaluation Of New 4 French Catheters By Comparison To 6 French Coronary Artery Images", J Invasive Cardiol 1999, 11(1):13-20; Dodge et al, "Coronary Artery Injection Technique: A Quantitative In Vivo Investigation Using Modern Catheters", Cathet Cardiovasc Dian, 1998, 44 (1):34-39)].

This high force pressure requirement makes the use of manual syringes (previously used in percutaneous coronary procedures with small sized catheters) functionally inadequate—since, with a 10-ml manual syringe, an operator can generally produce a hand pressure force only in the range of about 20-130 psi. The maximum pressure force which can be manually exerted is only about 130 psi; and is thus generally inadequate for injections through small sized catheters. Additionally, with any conventional manual syringe, the amount of pressure force which can be delivered by hand is inconsistent and will vary from person to person. Accordingly therefore, the injection flow rate and the fluid volume able to be delivered is likely to be very variable and the hand-generated pressure force will be somewhat unpredictable. Such undesirable conditions are only further exacerbated by the use of smaller sized catheters. [See for example, Brown et al., "Limitation In Use Of Five French Coronary Catheters", Int J Card Imaging, 1991, 7(1):43-45; Franken G. and E. Zeitler, Cardiovasc Radiol, 1978, 1:21-26; Ireland et al., Cathet Cardiovasc Diagn, 1989, 16:199-201; Saito et al., "Evaluation Of New 4 French Catheters By Comparison To 6 French Coronary Artery Images", J Invasive Cardiol 1999, 11(1):13-20; Dodge et al., "Coronary Artery Injection Technique: A Quantitative In Vivo Investigation Using Modern Catheters", Cathet Cardiovasc Dian, 1998, 44 (1):34-39].

These long-recognized limitations of the conventional manual syringe can and often do result in suboptimal quality of angiographic studies and frequently necessitate repeat injections—which, in turn, lead to toxic effects from contrast overdose such as renal or heart failure [McCullough et al., "Acute Renal Failure After Coronary Intervention: Incidence, Risk Factors, And Relationship To Mortality", Am J Med, 1997, 103:368-375].

As a consequence, there have been considerable efforts to make the conventional manual syringe more powerful by making various modifications in the shape and the ergonomics of the syringe, such as those disclosed by U.S. Pat. Nos. 4,925,449 and 6,616,634 respectively. Nevertheless, the various modifications developed to date for manual syringes have not been performance sufficient; and the modified syringes' injection flow rates and fluid volume capacities remain functionally inadequate and continue to cause suboptimal imaging results.

In addition, there have been other developments directed towards mechanisms for increasing the actuation force on the manual syringe by utilizing either internal or external springs to displace the plunger of the syringe, such as are described by U.S. Pat. Nos. 5,318,539 and 5,951,517 respectively. However, it remains very difficult to achieve the requisite injection pressure either reliably or in sufficiently high force in order to perform angiography using these spring-based actuated syringes.

Mechanical Power Injectors:

In the past, mechanical power injectors capable of providing higher-pressure fluid delivery have been adapted and used to overcome the disadvantages of the manual syringe during diagnostic and interventional coronary angiographic procedures. This has been especially true when the quality of imaging is hampered by the small size of the diagnostic catheter—as for patients with high coronary resistance or flows (due to hypertension, left ventricular hypertrophy, aortic regurgitation, or cardiomyopathy); and when there are interventional devices within the lumen of the guide catheter [See for example: Angelini P., "Use Of Mechanical Injectors During Percutaneous Transluminal Coronary Angioplasty (PTCA)", Cathet Cardiovasc Diagn, 1989, 16:193-194; and Goss et al., "Power Injection Of Contrast Media During Percutaneous Transluminal Coronary Artery Angioplasty", Cathet Cardiovasc Diagn, 1989, 16:195-198]. Nevertheless, mechanical power injectors have not been accepted by the majority of cardiologists because they were found to be cumbersome; to be expensive; and to have a number of other problems which are discussed in greater detail below.

In general, there are three types of mechanical power injectors: electric, hydraulic, or pneumatic (see Abram's Angiography, "Basic Types of Pressure Injectors", pages 171-175, $4^{th}$ edition, Little, Brown Company]. Each of these types of power injectors can provide the extra volume and power (between 100-1200 psi.) when a large syringe (65 to 130 ccs) is loaded into the power drive mechanism. Currently, electrically motorized injection devices are the most widely used and constitute a syringe connected to a linear actuator [as described by U.S. Pat. Nos. 4,006,736; 4,854,324; 5,269,762 and 5,322,511 respectively]. When used, the linear actuator is connected to a motor, which is controlled electronically. The operator determines via the electronic control a fixed volume of contrast material to be injected at a fixed rate of injection. The fixed rate of injection provides a specified initial rate of flow increase and a final rate of injection until the entire volume of fluid material (contrast media) is injected.

Mechanical power injectors can deliver a precise volume of contrast medium at higher pressure, resulting in more consistent coronary opacification. Enhanced visualization through power injection may be particularly beneficial in patients in whom opacification by manual syringe injection is difficult, such as patients with hyperdynamic or with high flow states (as may occur with aortic stenosis/insufficiency or hypertensive cardiovascular disease) and those patients with large caliber or dilated atherosclerotic vessels. Power injectors potentially can also enhance visualization when using smaller profile diagnostic and guiding catheters; and is especially important in interventions employing 5 to 6 Fr guides, in which visualizing coronary lesions through its internal annular space around indwelling balloon catheters and stent delivery systems by manual injection may be limited. [See for example: Goldstein et al, "A Novel Automated Injection System For Angiography", *J Invas Cardiol*, 2001,14:147-152].

It will be noted and appreciated, however, that these mechanical power injector devices also have some serious deficiencies: There is no interactive control between the operator and machine, except to start or stop the injection. Thus, any change in flow rate can occur only by stopping the machine completely and resetting the operating parameters. This lack of ability to vary the flow rate of fluid injection during the course of the procedure results in a suboptimal quality for angiographic studies because the optimal flow rate of injections typically varies considerably between different patients and different phases of cardiac cycles.

In the cardiovascular system, the rate and volume of contrast medium injection is dependent on the size of patient, the target organ and the blood vessels, as well as upon hemodynamic factors such as blood flow rate and pressure within the chamber or blood vessel being evaluated. In most cases, these parameters/factors are not known precisely and can change rapidly as the patient's condition changes in response to the variables of stress, different drugs, personal illness, or individual physiology. Consequently, the initial injection of contrast medium may be insufficient in flow rate to outline the structure on x-ray imaging, thereby necessitating another injection of medium—which can lead to toxic effects from overdose of contrast medium such as kidney or heart failure. Conversely, an excessive injection rate may injure the blood vessel or heart being evaluated, and also cause the catheter to become internally displaced (from the jet of contrast material exiting the catheter tip)—thereby resulting in severe adverse health outcomes such as life-threatening vascular or cardiac injuries (exemplified by dissection, or perforation of the artery, or cardiac arrhythmia).

In addition, some cardiologist have tried to use mechanical power injectors which were remotely activated using a hand or foot switch [See for example: Goss et al., "Power Injection Of Contrast Media During Percutaneous Transluminal Coronary Angioplasty", *Cathet Cardiovasc Diagn* 1989, 16:195-198; and Angelini, P., "Use Of Mechanical Injectors During Percutaneous Transluminal Coronary Angioplasty", *Cathet Cardiovasc Diagn,* 1989, 16:193-194]. Others have used a modified hand injector for specific application in percutaneous coronary intervention [See for example: Sanders et al., "Coronary Power Injection During Percutaneous Transluminal Coronary Angioplasty", *Cathet Cardiovasc Diagn,* 1984, 10:603-605; Ireland et al., "Safety And Convenience Of A Mechanical Injector Pump For Coronary Angiography", *Cathet Cardiovasc Diagn,* 1989, 16(3):199-201; and Weiner, R. I. and Maranhao V., "A Modified Hand Injector For Percutaneous Transluminal Coronary Angioplasty", *Cathet Cardiovasc Diagn,* 1987, 13:145-147]. All these attempts to employ mechanical power injectors were found to be cumbersome and clinically unsatisfactory.

More recently, a manually-operated, mechanically-assisted power syringe has been developed [as is disclosed by U.S. Pat. Nos. 5,830,194 and 6,030,368], wherein a syringe is assisted by an attached levered apparatus providing force amplification to the injection. Although providing a mechanically assisted advantage, a major disadvantage of this type of power syringe is its relatively large size and its complete immobility (due to its being fixed on the catheterization procedure table). Another disadvantage of this type of power syringe is the need for a second operator who must press down on a lever in order to actuate the injection action, while a first operator must hold the catheter in the desired position. Furthermore, there is no sense of fine control in either flow rate and/or fluid volume during the activation of lever and the actual injection of contrast medium into the catheter.

For these reasons, despite their having potential advantages, mechanical power injectors are infrequently used for coronary angiography. Operator's resistance to power injection of coronary arteries is based in part on the limitations of presently available motorized injectors, which do not allow the physician immediate control to vary the flow rate during power injection; and often result in insufficient contrast injection or excessive flow [see Goldstein et al, "A Novel Automated Injection System For Angiography", *J Invas Cardiol,* 2001, 14:147-152].

Other Relevant Developments:

1. ACIST Medical Systems (Eden Prairie, Minn., USA) has introduced a software-controlled variable rate syringe injector connected to an automated manifold without stopcocks. The ACIST Injection System (as disclosed by U.S. Pat. Nos. 6,221,045 and 6,344,030 respectively) is composed of four integrated components that include a software-controlled syringe injector, a disposable automated manifold without stopcocks, a disposable hand controller, and a touch screen control panel.

The ACIST Medical Systems injection system is mounted on its own wheeled stand; but is optimally utilized when firmly attached (immobilized) to the catheterization table. The touch screen control panel can be mounted on the syringe injector, but alternatively can be separately attached to the catheterization table and positioned in proximity to the operator. The disposable components (syringe body, manifold, check valves, and tubing) are provided in a separate sterile kit. The system setup is directed in a step-by-step maneuver using touch screen monitor prompts. After the initial setup is completed, the operator calibrates the hand controller and selects the injection program. The system is then ready to be connected to the angiographic catheter for angiography [see Goldstein et al, "A Novel Automated Injection System For Angiography", *J. Invas Cardiol,* 2001, 14:147-152].

Unfortunately, the ACIST injection system has a number of major disadvantages: The system is cumbersome to setup and load; and it requires additional disposable products to accommodate the complex repetitive steps and multiple connections. Moreover, the system has a very high cost for acquiring the essential equipment, for its operation and maintenance, and for the disposable supplies required for its continued use. Additional disadvantages are the injector's large size, its limited portability and its complexity of operation—all of which tend to lengthen the procedure time and to waste other resources such as staffing and facility. For these reasons, such software controlled injector systems for coronary angiography are not widely used; and presently, most laboratories employ only the manual syringe system for selective coronary angiography.

2. Another approach has been to substitute an electromechanical injector as an improvement upon manually-operated syringes. Examples of such injectors are described in U.S. Pat. Nos. 6,221,045; 5,383,858; 4,854,324; 4,677,980; 5,322, 511; and 4,006,736 respectively. These electromechanical injectors are made in the form of a conventional syringe, with the added feature of a force amplification system to overcome the limitations of the conventional manual syringe and power injectors.

3. Some earlier innovations were made in the form of a conventional syringe equipped with force amplications using a liquid gas such as carbon dioxide. In 1956, Gidlund first described a compressed-air injector with a stainless steel syringe that could be placed in a vertical position [Gidlund A., "Development Of Apparatus And Methods For Roentgen Studies In Haemodynamics", *Acta Radiol (Stockh)*, 1956, 130(suppl):1]. The vertical position facilitated the addition of a valve for air removal at the top of the syringe.

Later, in 1960, Amplatz described a pneumatic power injector for injection of contrast medium powered by carbon dioxide cartridges. [Amplatz K., "A Vascular Injector With Program Selector", *Radiology*, 1960, 75:955]. The Amplatz pneumatic power injectors used compressed gases to transmit pressure to a barrel, which were connected to the injector syringe. The device operates under basic pneumatic and hydraulic principles [see Abram's Angiography, "Basic Types Of Pressure Injectors", 4$^{th}$ edition, Little, Brown & Company, pages 171-175]. However, a bulky and heavy pressure regulator was one of the essential parts of these injectors. Each pneumatic power injector weighed more than 5 kg and were not practical for use in any clinical setting.

4. Another approach is the Bourdon device (as disclosed by U.S. Pat. No. 4,323,066; the text of which is expressly incorporated herein by reference). The Bourdon device is a modified syringe that allows the operator to regulate the speed at which injection occurs and can alter the flow rate of injected liquid. Functionally, a gas from a pressurized-gas source flows continuously through the device and exits freely into the atmosphere, thereby wasting large quantities of gas needlessly. Also, the amount of gas required for a single injection procedure is much larger than can be stored in a miniature cylinder; and thus a remote source of pressurized-gas is always required in each instance of use.

5. Still another variation is the Smith et al. syringe device (as disclosed by U.S. Pat. No. 4,861,340; the text of which is expressly incorporated herein by reference). The Smith et al. syringe is intended to provide control of contrast flow rate (as in the Bourdon syringe device described above), but has a configuration that addresses the gas-wasting problem. The syringe is designed for injecting contrast media into the vascular system during angiography; and is composed of two main parts: the injection syringe itself and the gas system. The function of the gas system is to deliver regulated pressurized $CO_2$ gas to the injection syringe to assist the forward motion of the piston. The pressurized gas is contained in a $CO_2$ gas tank and is regulated by the operator. This required pressure regulation allows the operator to adjust the pressure to a desired setting.

It will be noted that pressurized gas is conserved in the Smith et al. syringe design by the use of a configured portal system, which allows gas flow from the pressurized-gas source to occur only during contrast medium injection. This, however, markedly reduces the operator's sensation of flow rate control, which is very critical in practice of cardiac catheterization, in terms of both safety and efficacy.

It will be appreciated that within the Smith et al. system design, the marked reduction in the operator's sensation of flow rate control is caused directly by an undesirably large "dead band". From the operator's perspective, a "dead band" is the difference between the relative motion of the operator's fingers and the displacement of the piston in the syringe barrel. The mechanical distances required to separate axial source ports using O-rings thus dictates the size of the dead band. Increasing or decreasing the contrast flow rate occurs in a step-wise manner as the operator-applied force is varied; and the dead band variances between the steps and the limited number of steps in a practical device markedly reduce the operator's sensation of flow rate control as compared with a conventional manual syringe. The Smith et al. device also requires a pressure regulator, which makes the system cumbersome and difficult to handle. For these reasons, the Smith et al. device was deemed to be clinically impractical and was unfavorably received by medical practitioners shortly after its introduction [see Pande et al., "Randomized Evaluation Of 5 French Catheters For Coronary Angiography With Or Without The $CO_2$ Powered Hercules Syringe", *J Invas Cardiol*, 1992, 4:136-138].

Clearly therefore, there remains a well recognized and long standing need for a power-assisted syringe that can overcome the various problems associated with the injection of contrast medium in the different angiographical procedures. Accordingly, were a syringe apparatus capable of delivering contrast fluid on-demand to a patient to be developed which permits the operator to adjust and increase appropriately the force applied to the syringe and provides feedback parameters with tactile and visual components by which to control the flow rate and volume of the fluid in real time, such an improvement would be seen as having substantive medical benefit and be recognized as a major advance and improvement within the technical field.

SUMMARY OF THE INVENTION

The present invention has multiple aspects and embodiments. A first aspect of the instant invention provides a portable, self-contained and hand-held power assisted syringe comprising:

a barrel assembly having proximal and distal ends and an internal spatial volume for containing and delivery of a fluid material;

a nozzle connected to said distal end of said barrel assembly for ejecting fluid material contained within said internal spatial volume of said barrel assembly;

a plunger assembly comprising a plunger member and a plunger plate slidably disposed within said barrel assembly;

a manually controlled valve housing assembly comprising a source valve and a vent valve which can be opened and closed repeatedly at will, said valve housing assembly being in fluid flow communication with said plunger assembly, and being able to receive pressurized gas from a portable source, and being able to direct and deliver said received pressurized gas on-demand to said plunger assembly;

operating means by which to apply a hand-generated force to said plunger assembly; and means for attaching a portable source of pressurized gas to said valve housing assembly, such that a portable source of pressurized gas can be attached and thereby provide pressurized gas to said valve housing assembly.

A second aspect of the invention provides a method for the power assisted operation of a syringe device, said method comprising the steps of:

obtaining a portable, hand-held power assisted syringe device comprised of
  (i) a barrel assembly having proximal and distal ends and an internal spatial volume for containing a fluid material to be delivered,
  (ii) a nozzle connected to said distal end of said barrel assembly for ejecting fluid material contained within said internal spatial volume of said barrel assembly,
  (iii) a plunger assembly comprising a plunger member and a plunger plate slidably disposed within said barrel assembly,
  (iv) a manually controlled valve housing assembly comprising a source valve and a vent valve which can be opened and closed repeatedly at will, said valve housing assembly being in fluid flow communication with said plunger assembly, and being able to receive pressurized gas from a portable source, and being able to direct and deliver said received pressurized gas on-demand to said plunger assembly, (v) operating means by which to apply a hand-generated force to said plunger assembly, and (vi) means for attaching a portable source of pressurized gas to said valve housing assembly such that a portable source of pressurized gas can be attached and thereby provide pressurized gas to said valve housing assembly;

attaching a portable source of pressurized gas to said syringe device; and applying pressurized gas from said portable source to said valve housing assembly which is then directed and delivered on-demand to said plunger assembly of said syringe device, whereby said pressurized gas causes a power assisted operation of said plunger assembly.

BRIEF DESCRIPTION OF THE FIGURES

The invention may be more easily understood and better appreciated when taken in conjunction with the accompanying drawing, in which:

FIG. 2A is a schematic cross-section view of the first embodiment for the power-assisted syringe illustrated by FIG. 1;

DETAILED DESCRIPTION OF THE INVENTION

Figure 1:
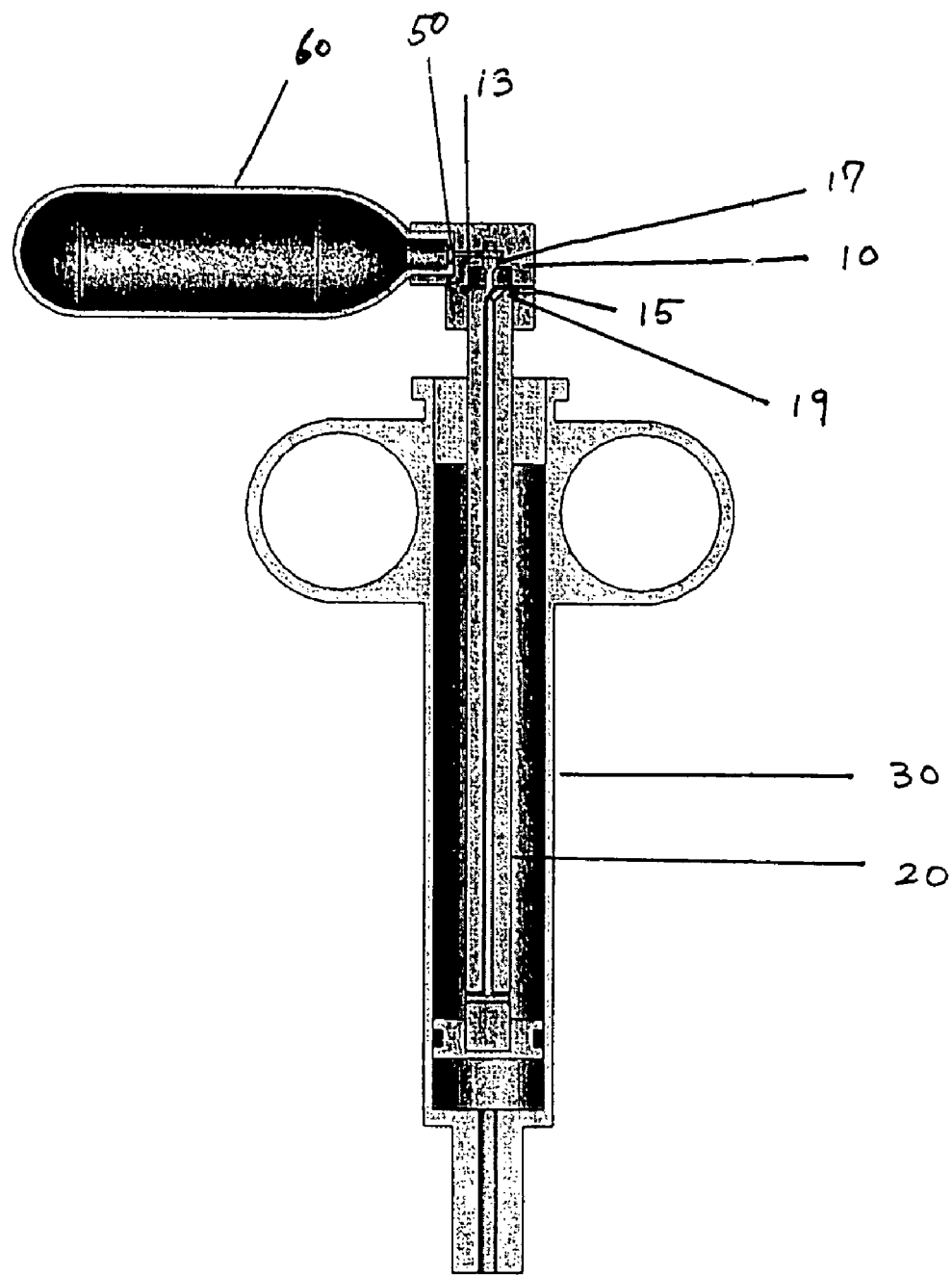
FIG. 1 is a perspective cross-sectional view of a first embodiment for the power-assisted syringe configuration of the present invention.

The instant invention is a power assisted syringe which overcomes the shortcomings of traditional manual syringes, presently available mechanical syringes, and other conventionally known mechanical injectors medically used today in angiography. Among its many unique features, benefits and advantages are the following:

1. The present invention provides a self-contained, power-assisted syringe for the injection of liquids or gases during those medical procedures which use small-bore diagnostic catheters and small guiding catheter systems (such as coronary angiography and interventional procedures respectively). The instant invention provides a greater degree of injection power, which is very desirable in coronary artery interventions and other procedures; and can deliver larger volumes of contrast medium at greater pressure forces than is possible using a conventional manual syringe.

2. The present invention provides a hand-held, fully self-contained syringe which has the appearance, ergonomics, feel, and ease of use similar to that of a conventional manual syringe. Moreover, this improved syringe liberates the physicians' hands and allows him to operate the primary catheterization equipment simultaneously. The power-assisted syringe, along with all components necessary for operation, can be pre-packaged and pre-steriled within a single container and disposed of after use.

3. The present invention does not utilize and does not require a remote pressure regulator valve, nor a remote supply of high-pressure gas, nor any other remote accessory for functional operation. Nothing beyond that which is also necessary for the operation of a conventional manual syringe is needed.

4. The present invention comprises a pressurized-fluid container which is directly integrated into the hand-held syringe device. The components preferably used for mechanical integration and installation of a pressurized-fluid container into the power-assisted device include: a piercing component to open the pressurized fluid container; a sealing component to prevent leak-age of pressurized fluid; and a force applying component, such as threads, to press the pressurized fluid container against the sealing component in order to prevent leakage. Other components will typically include a heat exchanger with gas passage(s); a miniature canister of pressurized gas such as liquid carbon dioxide; and a valve housing assembly having a regulating source valve (a needle valve) adapted to communicate with a pressurized gas source and a regulating vent valve (a needle valve) adapted to vent and exhaust gas.

5. In the present invention, a controlled passageway for the travel of fluid (such as gas) extends through the valve housing assembly, the plunger assembly between the fluid (gas) inlet, and the fluid (gas) outlet, and a by-pass flow passage around an inlet (source) valve. The utilization of regulatory needle valves in this power-assisted syringe is one of the key features with this invention. The needle valves have a slender, tapered point at the end of the valve stem that is lowered through the seat to restrict or block flow. Fluid flows via a by-pass flow passage around the valve and passes through an orifice that is the seat for a rod with a cone shaped tip.

The needle valve dispenses fluid when the activator (for example, manual force, spring or gas) acts on a piston, which shifts the spool or needle into the open position. A second actuator (for example, fluid pressure) forces the fluid to flow. When the valve activator stops, a spring force shifts the spool or needle to the closed position. These small valves are used to accurately regulate the flow of fluids and gases at certain flow rates. The fine threading of the valve stem and the larger seat area allow for precise resistance to flow. In addition, needle valves allow gradual increase in pressure and flow rate. Therefore, needle valves are used to control flow into delicate human body tissues such as blood vessels, which might be damaged by sudden surges of fluid under pressure. Needle valves are also used in situations where the flow must be gradually brought to a halt, and at other points where precise adjustments of flow are necessary or where a small flow rate is desired for medical use. They can be also used as both on/off valves and for throttling function.

6. The present invention also provides a method for power injecting fluid. In essence, the method comprises attaching a source of liquefied gas (having a known vapor pressure) to a power-assisted syringe; and operating the syringe by manually applying a pressure force to a plunger assembly slidably disposed within a barrel assembly. The source of liquefied gas supplies pressurized gas at the vapor pressure to a valve housing assembly which, in turn, directs the pressurized gas to assist in the operation of the plunger assembly.

7. The present invention optionally can also be used as a conventionally acting or ordinary-use syringe when there is a low resistance environment which requires a pressure force not more than can be manually generated by hand. By withdrawing the plunger together with the piston, a liquid medium can be drawn into the interior of the barrel. Then, by moving the plunger together with the piston forwards and back into the barrel (in which the valve can be idle or turned off by a switch mechanism), the liquid medium will be expelled from the barrel through the nozzle. This outcome yields a result which is the same as that obtained with conventional manually operated syringes.

I. The Underlying Limitations of and Requirements for a Clinically Useful Power Assisted Syringe Clinically useful angiograms require a that minimum density (opacity) of radiopaque contrast medium exist in the blood flow of the vessel to be diagnostically evaluated. Typically, a highly concentrated contrast medium [such as Omnipaque (iohexol)-350, Isovue (iopamidol)-370, or Optiray (ioversol)-350] are used for angiogram procedures such as a coronary angiogram. These contrast media contain organically bound iodine [in about 350 mg/ml to 370 mg/ml ranges]; and are very viscous fluids with a viscosity ranging from 9.0 to 11.1 CPS at temperature of 37° C. [a range which is much higher in viscosity than the 1 CPS of water]. The high viscosity of contrast medium fluids result in a high resistance to flow.

The volume flow rate (F) can be calculated according to Poiseuille's equation (for smooth, laminar flow) as:

$$\text{Volume Flow rate } (F) = \frac{(P_1 - P_2)}{R}$$

where $(P_1-P_2)$ is the pressure difference along a tube and R is the viscous resistance to flow of the fluid. In smooth, laminar flow, the viscous resistance (R) depends linearly upon the viscosity of the fluid and the length of the tube, but has a fourth power dependence upon the radius of the tube.

Thus, the volume flow rate (F) can be rewritten as:

$$\text{Volume Flow rate } (F) = \frac{\pi(P_1 - P_2)(r)^4}{8(\eta)(L)}$$

where r is the inner radius of the tube, η is the viscosity of the fluid, and L is the length of the tube. Poiseuille's equation is found to be in reasonable agreement with experiments for uniform liquids (also called 'Newtonian fluids') in cases where there is no appreciable turbulence.

From this equation, one can also draw the following conclusions:
1. The speed of injection can be increased by using contrast medium with low viscosity.
2. The speed of injection can be increased by using short, thin-walled catheters.
3. Increasing the pressure of injection will increase the delivery of rate [see Abram's angiography, "Basic Types Of Pressure Injectors", 4th edition, Little, Brown Company, pages 171-175].

Typically, contrast medium fluid is injected in varying volumes (1 to 10 cc/sec) and durations of injection (1 to 5 seconds) depending on the size and flow of the blood vessels [Dodge et al., "Coronary Artery Injection Technique: A Quantitative In Vivo Investigation Using Modern Catheters", Cathet Cardiovasc Diagn., 1998, 44 (1):34-39]. For good quality coronary imaging, highly concentrated contrast medium fluid (76%, or 370 mg/ml of iodine concentration) should be injected into the right and left coronary arteries (relatively high flowed arteries) at an injection rate of at least 2 to 5 cc/sec for about 2-3 seconds. If the injection time takes substantially longer than approximately three seconds for same total volume of contrast medium (which means less amount per second), the density of the contrast medium in the blood vessel decreases due to increased dilution of the contrast medium with blood flow—thereby reducing its diagnostic usefulness since the morphology and pathology of the vessels will not stand out sufficiently and will become obscured within the background of the field of view.

Therefore, in order to maintain a desired volume flow rate of contrast medium injection for catheters of decreasing size [i.e., for catheters of decreasing radius (r)], Poiseuille's equation indicates that: (i) either the viscosity (η) of the contrast medium must be decreased; or (ii) the length (L) of the catheter must be decreased; and/or (iii) the injection pressure $(P_1-P_2)$ must be increased.

However, in actual clinical practice, the high concentration (highly viscous) of contrast medium cannot be reduced, as any reduction in concentration will significantly compromise the quality of the coronary artery images. Equally important, the length of the catheter must remain fixed (about 90-100 cm) because the anatomic distance between the heart and groin (the catheter entry site) cannot be changed. Thus, the only choice available in practice for maintaining volume flow rate of contrast medium injection when using smaller sized catheters (less than 6 French) is an increase of injection pressure force.

It will also be appreciated that serious complications sometimes take place and occur after the catheterization procedure is completed; and such complications are known to be closely related to the size of the puncture hole made on the access blood vessels to accommodate a specific size of catheter. Accordingly, the smaller the size of catheter employed for the procedure, the smaller the size of the puncture hole in the blood vessel, and the less the risk of subsequent complications. However, smaller sized catheters (such as 4 and 5 French) make manual syringe injection of the viscous contrast medium far more difficult, since their catheter inner diameters also become smaller.

Note that a 4 French catheter has an inner diameter of approximately 1.1 mm—which is about 21% smaller than that of a 6 French catheter (1.4 mm), and approximately 31% smaller than that of a 7 French catheter (1.6 mm). These sizing differences translate into area reductions of approximately 38% and 53% respectively; and also translate into fluid flow reductions of approximately 61% and 78% respectively, according to Poiseuille's equation. Similarly, a 5 French catheter has an inner diameter of approximately 1.2 mm, which is about 14% smaller than that of a 6 French catheter and is approximately 25% smaller than that of a 7 French catheter. These differences translate into area reductions of approximately 26.5% and 43.7% respectively and into fluid flow reductions of approximately 46% and 68% respectively.

Again according to Poiseuille's equation, the fluid flow difficulties caused by any reduction in catheter inner diameter has to be compensated by increasing amount of injection force required to propel the contrast medium of the same viscosity through a smaller-diameter catheter [Dodge et al., "Coronary Artery Injection Technique: A Quantitative In Vivo Investigation Using Modern Catheters", Cathet Cardiovasc Diagn., 1998, 44 (1):34-39]. For these reasons, there is typically no difficulty in obtaining a minimum opacification of the blood vessel with contrast medium injection when using catheters of a 6 French size or larger.

However, even as the internal lumen diameters of the catheter are decreased, operator hand strength is and remains quite limited; and the question of human hand strength becomes a substantive limiting factor for sufficient administration of contrast medium, even when two hands are used. An insufficient manual strength for the operators of a manual syringe often results in an unsatisfactory quality of clinical evaluations. Moreover, with more repetitive injections of fluid and a use of more contrast medium, the operators become subject to a risk of acute or chronic injuries of the wrist, hand and fingers and the patients become subject to a risk of contrast-induced renal failure and more radiation exposure.

II. The Structure of the Power-Assisted Syringe Comprising the Present Invention The present invention is shown as exemplary embodiments by FIGS. 1-16 respectively. It is to be clearly understood that, in some instances, one or more aspects of the invention may be shown in exaggerated or enlarged form to facilitate a better understanding of the subject matter as a whole which constitutes the invention.

1. A Preferred First Embodiment

Figure 2B:
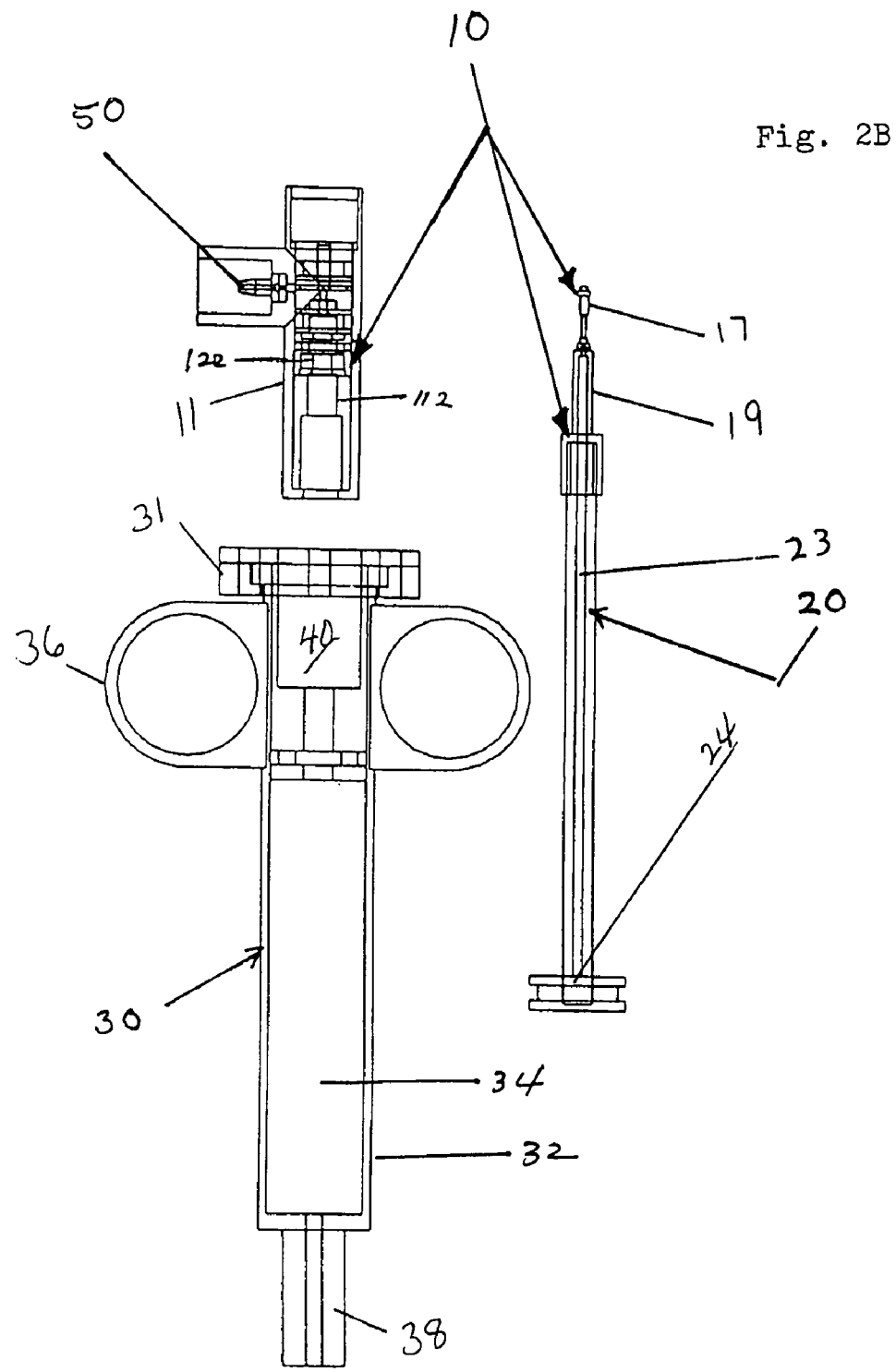
FIG. 2B is a schematic view of the disassembled first embodiment for the power-assisted syringe illustrated by FIG. 1.

A first embodiment of the power-assisted syringe device is shown in alternative cross-sectional views by FIGS. 1, 2A and 2B respectively. FIG. 1 shows a cross-sectional perspective view of this embodiment of the power assisted syringe. FIGS. 2A and 2B are schematic illustrations of a power assisted syringe device of FIG. 1 that has been successfully tested. FIG. 2A shows a cross-sectional schematic view of an assembled device, while FIG. 2B shows a cross-sectional schematic view of an disassembled device.

As a further aid, FIGS. 3A to 3D show exploded views of these same assemblies. As seen therein, the portable and self-contained power assisted syringe comprises a manually controlled valve housing assembly 10, a plunger assembly 20, a syringe barrel assembly 30, attachment means 50 for connecting a portable source of pressurized gas to the value housing assembly 10, and a portable pressurized gas source 60 (seen as a miniaturized gas cylinder). The valve housing assembly 10 is connected via attachment means 50 to the pressurized gas source 60 and will receive a gaseous pressure force directly from the gas source 60; The valve housing assembly 10, in turn, is connected to and is in fluid flow communication with the plunger assembly 20; and is thereby able to direct and to deliver pressurized gas on-demand to the interior of the plunger assembly 20. The plunger assembly 20, in turn, lies within and can pass axially through the linear length and interior spatial volume 34 of the syringe barrel assembly 30.

Also as seen in FIGS. 1-3 collectively, the syringe barrel assembly 30 comprises an upper barrel section 40; a threaded barrel bolt 31; a barrel tube 32 having proximal and distal ends 33 and 35; and an elongated internal lumen (barrel space) 34. A set of finger rings 36 are attached to the exterior surface of the barrel tube 32; and a nozzle 38, having an open passageway 39, is connected to the distal end 35 of the syringe barrel assembly 30 for the ejection of fluid by using the plunger assembly 20. In this first embodiment, the operating means which are used to apply a hand-generated pressure force to the plunger assembly 20 of the syringe device are the finger rings 36 attached to the barrel tube 32.

Figure 3A:
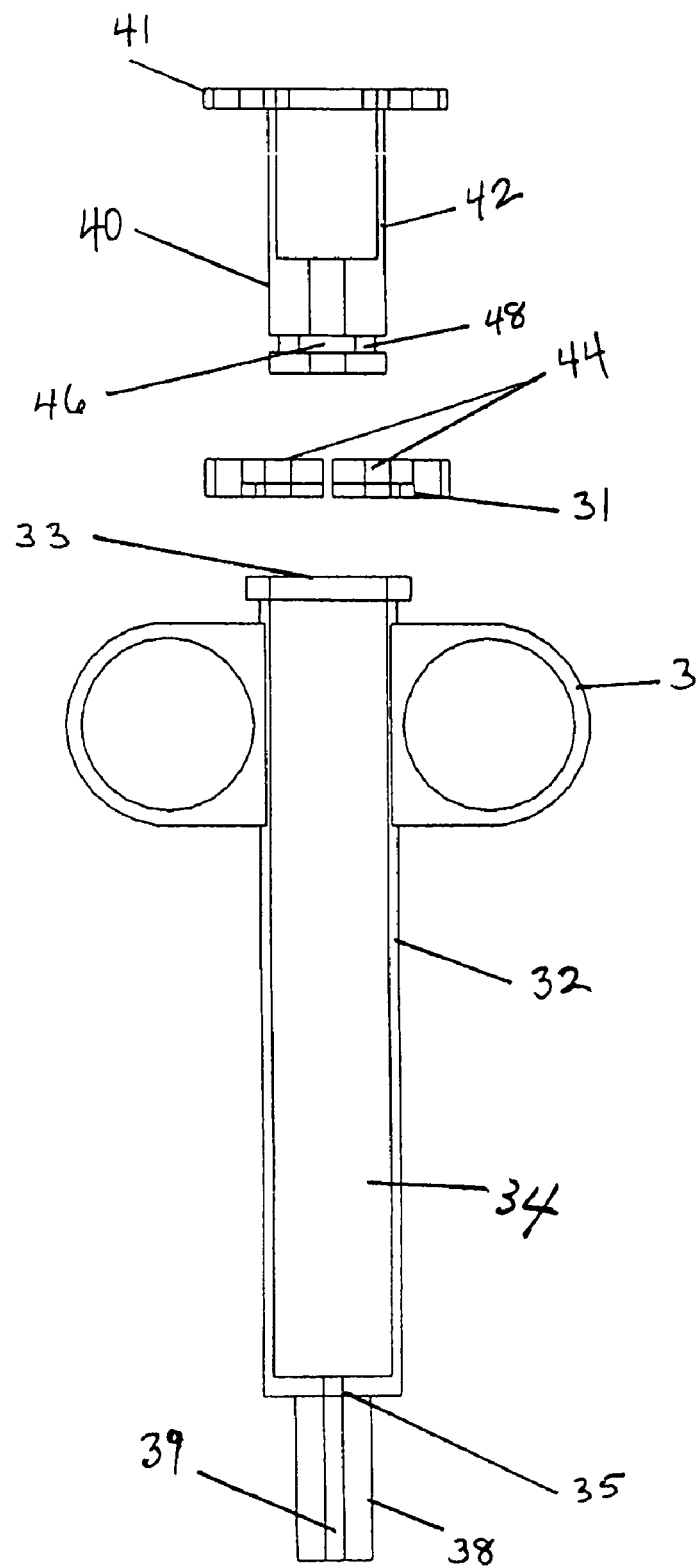
FIG. 3A is an exploded schematic view of the barrel assembly of the first embodiment for the power-assisted syringe illustrated by FIG. 1.

FIG. 3A shows some detailed features of the upper barrel section 40 of the syringe barrel assembly 30. The upper barrel section 40 typically has a barrel plug 42, barrel plug ring(s) 44, at least one bolt circle 41, and inner and outer O-ring grooves 46 and 48. The upper barrel section 40 is joined to the barrel tube 32 via the threaded barrel bolt 31 to form the complete barrel assembly 30.

Figure 3B:
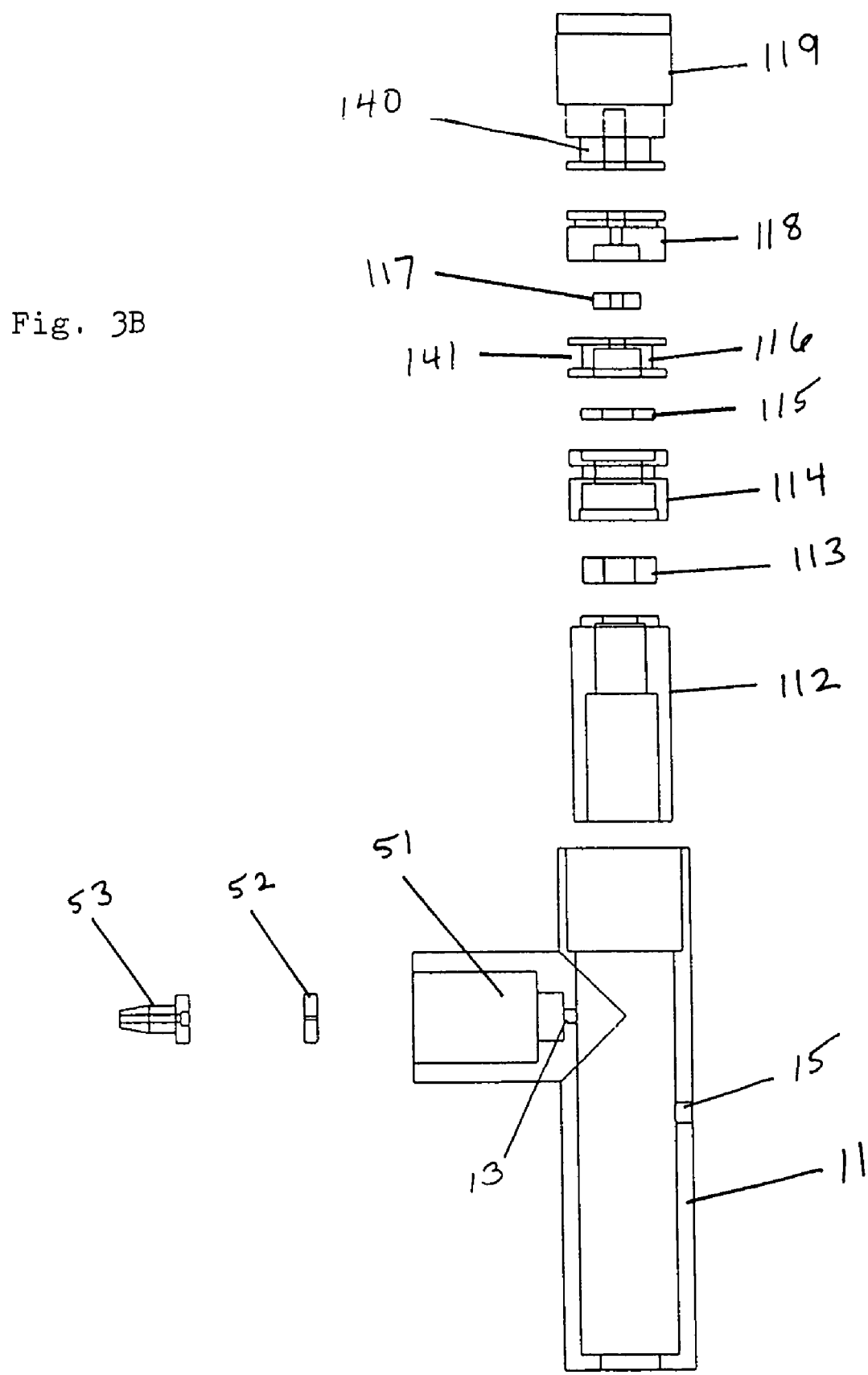
FIG. 3B is a perspective view of the valve housing of the first embodiment for the power syringe illustrated by FIG. 1.

FIG. 3B shows an exploded cross-section view of the structural details and mechanical features for the valve housing assembly 10. As seen therein, the valve housing assembly 10 includes: a valve housing 11, a vent spring housing 112, a vent valve guide 113, a vent housing 114, a vent washer 115, a seal housing 116, a source washer 117, a source housing 118, a housing plug 119, and two O ring grooves 140 and 141. In addition, the valve housing 11 also provides the means for attaching a source of pressurized gas 50 which includes: the receiving chamber 51, the orifice 52, the attaching nib 53.

Figure 3C:
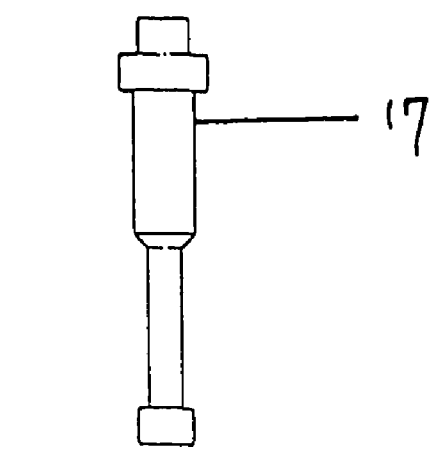
FIG. 3C is an exploded view of the source (inlet) and vent (exhaust) valves of the first embodiment for the power syringe illustrated by FIG. 1.
Figure 3C:
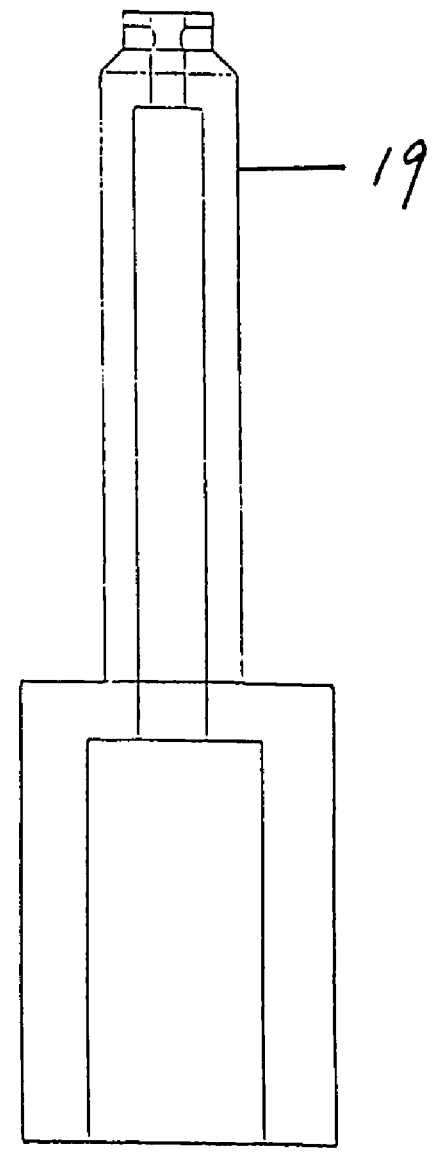

FIGS. 3B and 3C show the valve regulating features of the valve housing assembly in detail. As seen therein, the valve housing assembly 10 comprises several major component parts: a valve housing 11, a gas inlet port 13, a regulating source valve 17, a regulating vent valve 19, and a gas outlet port 15. Also within the valve housing 11 are a source valve sealing surface 102 (see FIG. 4D), a vent valve sealing surface 103 (see FIG. 4D), and a plunger guide bearing surface 122 (see FIG. 4D). The organization, structural arrangement and reciprocal interaction of these valve regulating component parts and features is discussed below.

Figure 3D:
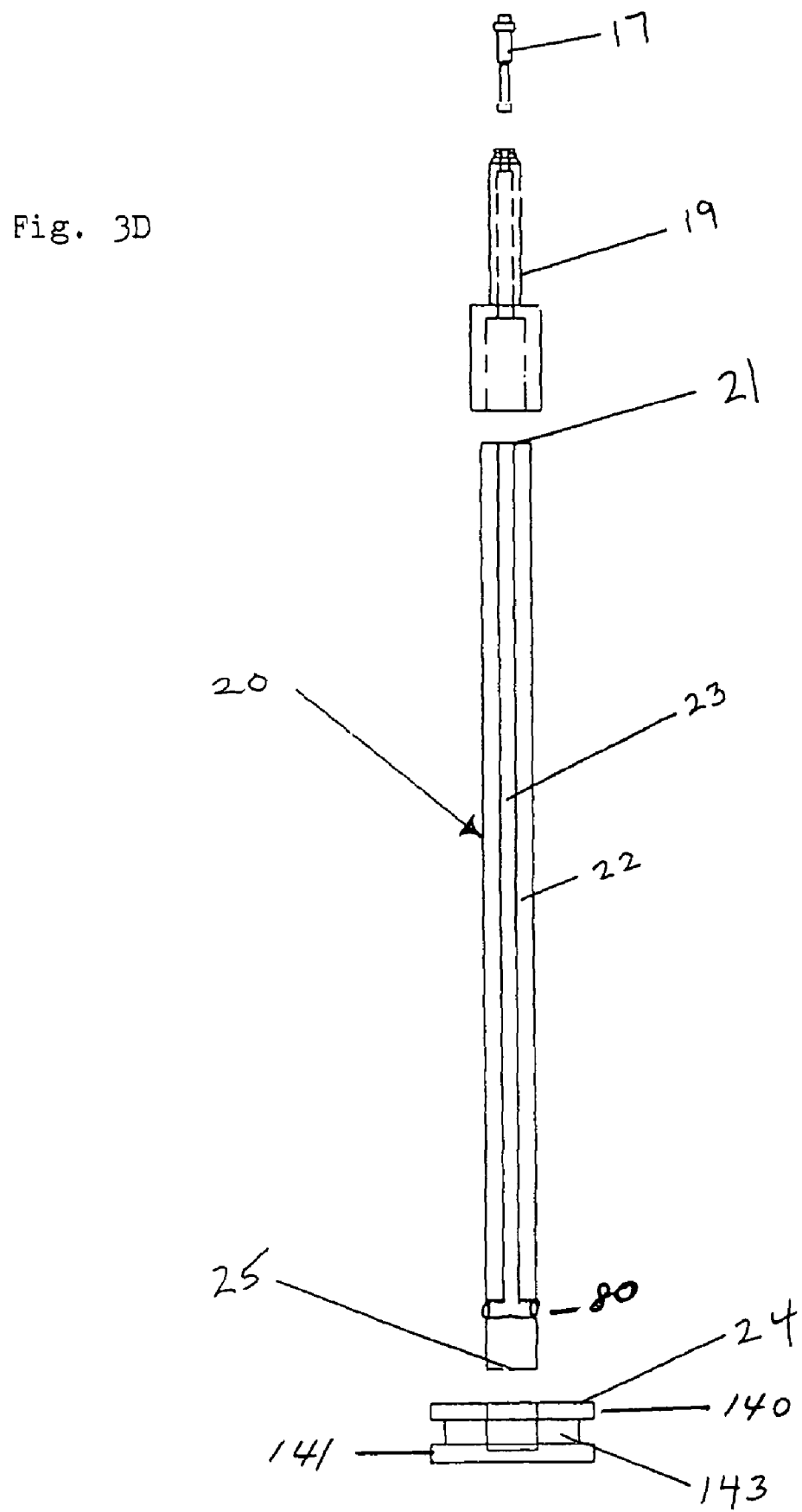
FIG. 3D is a perspective view of the plunger assembly with the source (inlet) valve and vent (exhaust) valve of the first embodiment for the power-assisted syringe illustrated by FIG. 1.

The regulating source valve 17 and regulating vent valve 19 are shown in an overhead perspective view by FIGS. 3C-3D. Each of these is a spring biased, gas regulating valve. The vent valve 19 has an interior hollow channel for the passage of pressurized gas; the source valve 17 does not. These regulating valves 17 and 19 are dimensioned and configured to fit into and reciprocally interact as a stacked pair with the aligned internal inlet and outlet ports 13 and 15, the working space (by-pass flow passage) between the perimeter of the source valve and source valve sealing surface 102 (see FIG. 4), and the valve working volume 120 (see FIG. 4) respectively existing within the interior of valve housing 11. As shown, the regulatory source valve 17 sits upon and is supported by the top of the regulatory vent valve 19. Both of these gas regulating valves are then fitted upon the top (or proximal end) of the plunger member 22 of the plunger assembly 20 as shown by FIG. 2B.

The plunger assembly 20 shown in FIGS. 1 and 2B is illustrated in greater detail by FIG. 3D. The plunger assembly 20 comprises a plunger tube member (or push rod) 22 which has an elongated and centrally disposed hollow channel 23 extending axially over its length and has a solid piston (or circular plunger plate) 24 at its distal end 25. The piston 24 has a longitudinally spaced annular groove 143 around its perimeter and girth which will receive an O-ring, and thereby provide a fluid-tight seal for the plunger assembly while lying within the lumen of the syringe barrel.

As seen in FIGS. 2B and 3D respectively, the regulating vent valve 19 is located at the proximal end 21 of the plunger assembly 20; and the regulating source valve 17 is fitted into the interior of the vent valve 19. A plunger guide bearing surface 122 (see FIG. 4) provides proper alignment of the plunger assembly 20 as a whole when joined to the valve housing assembly 10 and when inserted into the barrel assembly 30.

Figure 4A:
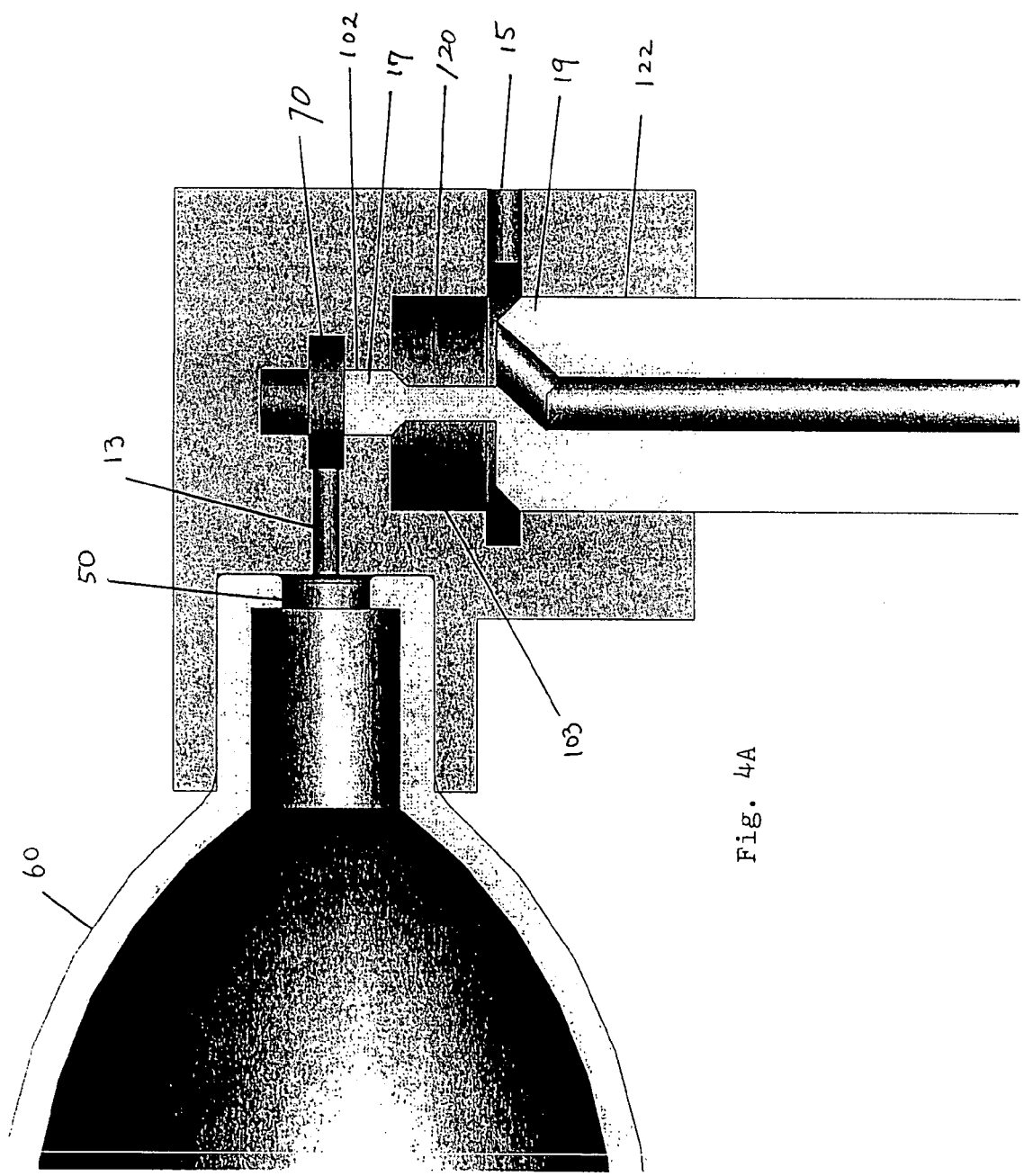
FIG. 4A is a perspective view illustrating the initial position (source valve is closed and vent valve is open to gas outlet port) for the operation of the first embodiment (at rest) for the power-assisted syringe illustrated by FIG. 1.
Figure 4B:
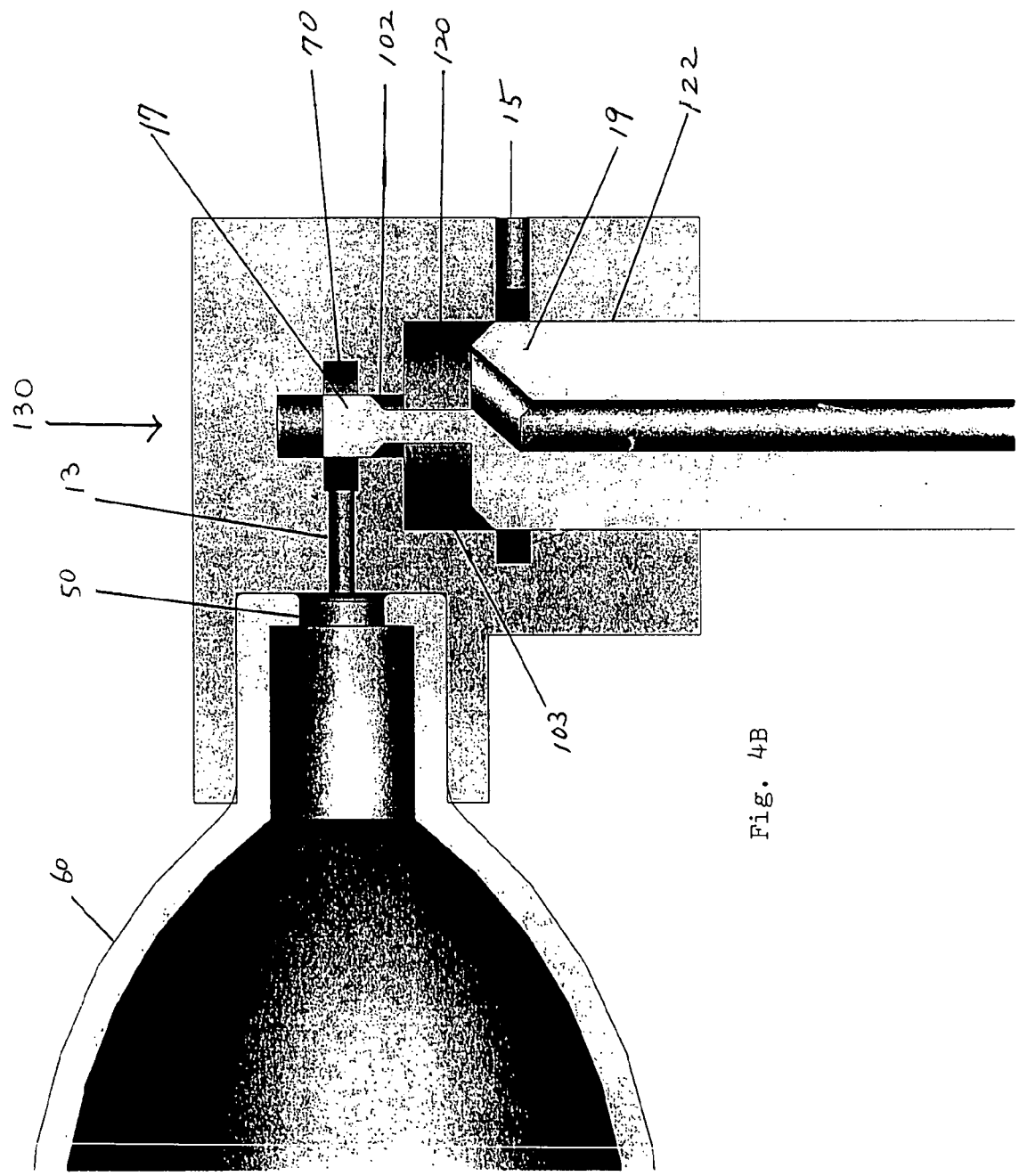
FIG. 4B is a perspective view illustrating a second position (source valve is still closed and vent valve is closed to gas outlet port) in the operation of the first embodiment (at the beginning of the force applied to the plunger) for the power-assisted syringe illustrated by FIG. 1.
Figure 4C:
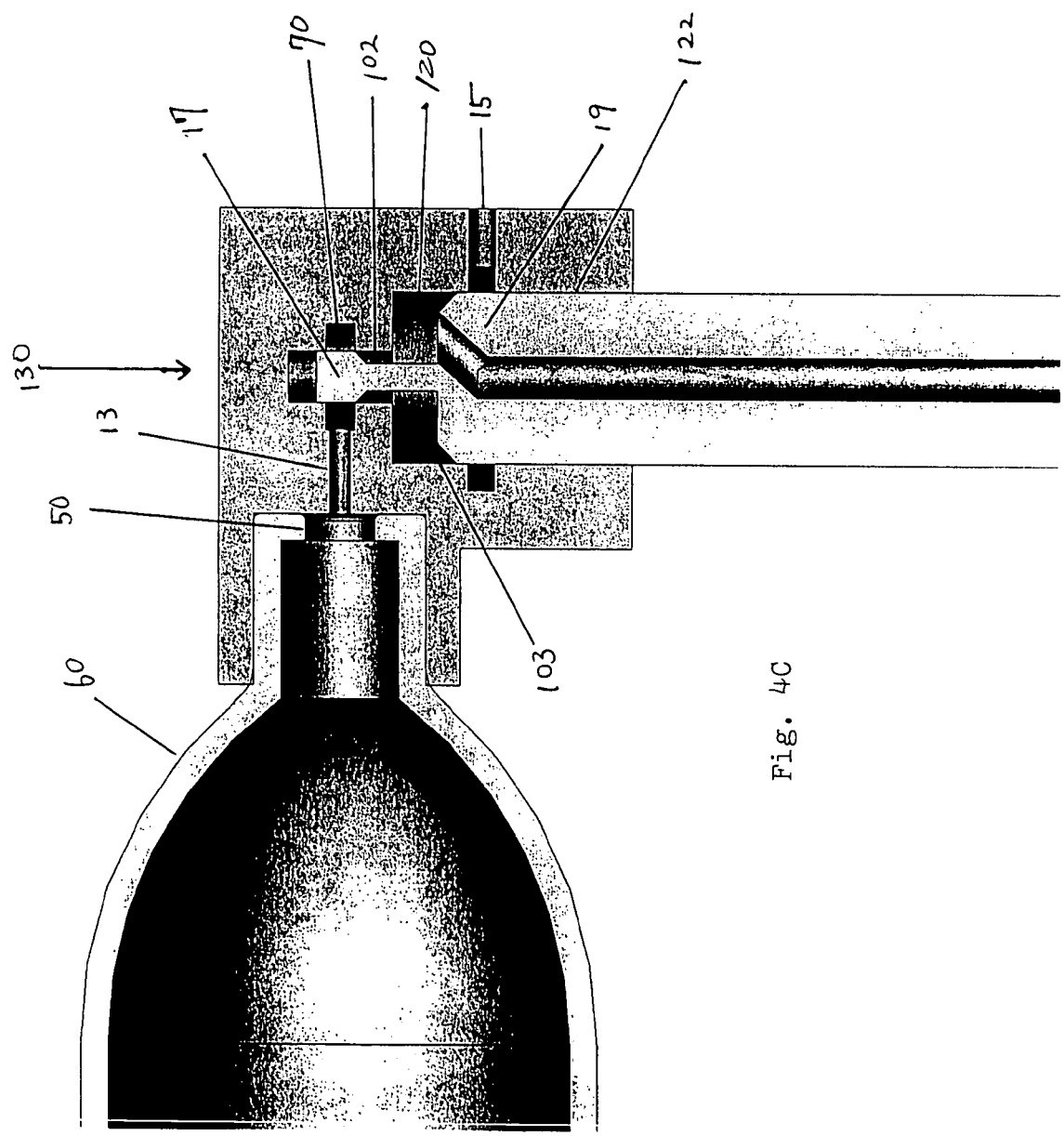
FIG. 4C is a perspective view illustrating a third position (source valve is about to open and vent valve remains closed to gas outlet port) in the operation of the first embodiment (the force continued to be applied to the plunger) for the power-assisted syringe illustrated by FIG. 1.
Figure 4D:
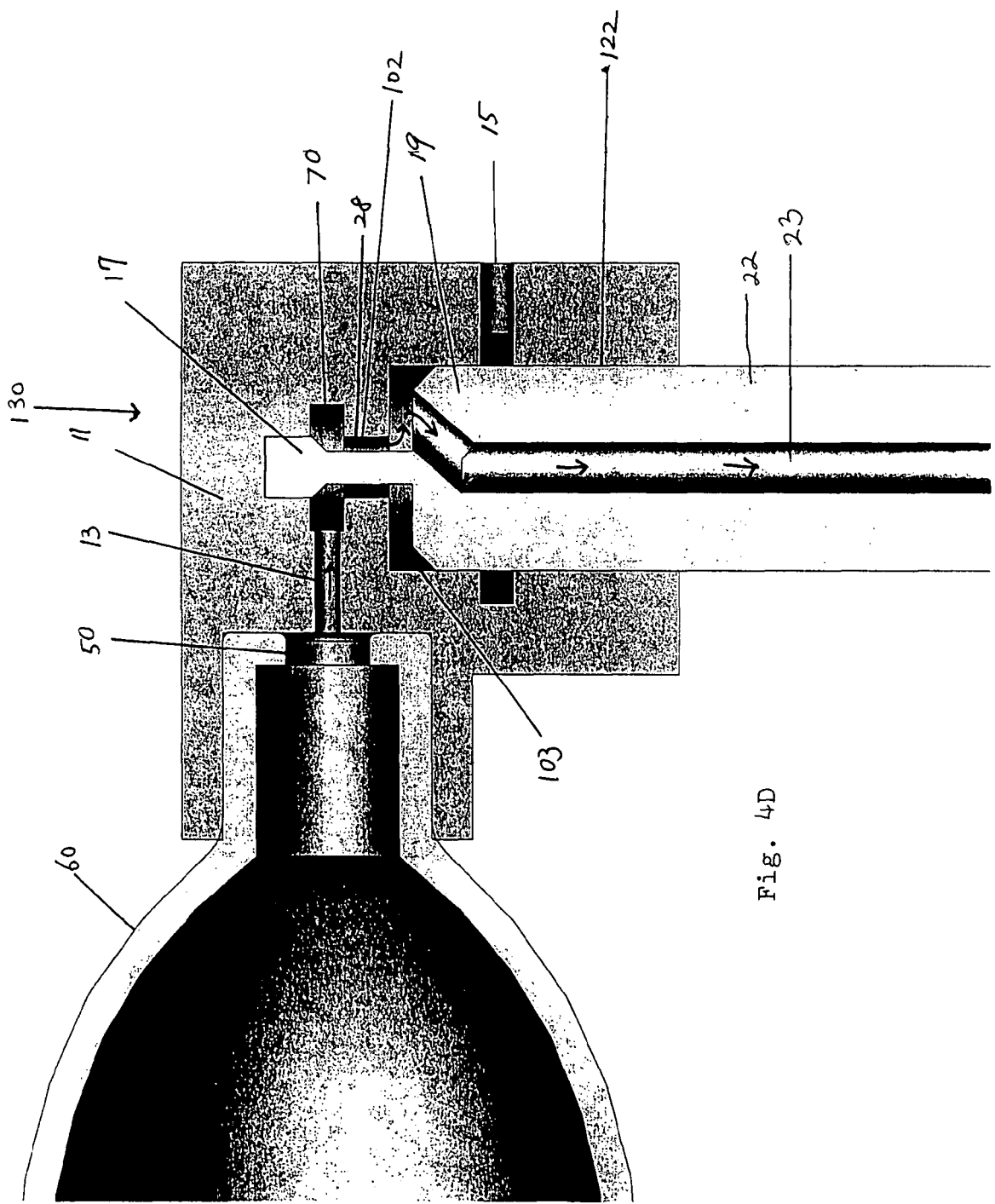
FIG. 4D is a perspective view illustrating a fourth position (source valve is open to gas inlet port and to the plunger tube passage through the space (source port) between the source valve and source valve sealing surface so that gas moves from the gas source to barrel of syringe following arrows) of the operation of the first embodiment (the force continued to be applied to the plunger) for the power-assisted syringe illustrated by FIG. 1.

As seen in FIGS. 3D and 4D respectively, with the source valve 17 in the open position and the vent valve 19 in the closed position, the fluid (gas) flows from the source 60 through the gas inlet port 13, the source port 28 (the space existing as a by-pass flow passage between the perimeter of the source valve and source valve sealing surface), the valve working volume 120 (formed by the space between the perimeter of the vent valve at the proximal end of the plunger 22 and the vent valve sealing surface), into the hollow channel 23 of the plunger member 22 and then into the barrel space 34 proximal to the piston 24.

In this first embodiment, it will be recognized and appreciated that the plunger tube member 22 at its distal end includes a pair of apertures 80 which are in fluid flow communication with the hollow channel 23 of the plunger tube member 22. The apertures 80 permit such pressurized gas as enters and travels through the hollow channel 23 to escape from the interior of the plunger tube member 22 and to pass into the spatial volume of the barrel lumen 34. In this manner, such pressurized gas as is introduced from the gas source 60 through the valve housing assembly 10 must pass through the hollow plunger tube member 22 before entering the lumen 34 of the barrel assembly 30.

Figure 4E:
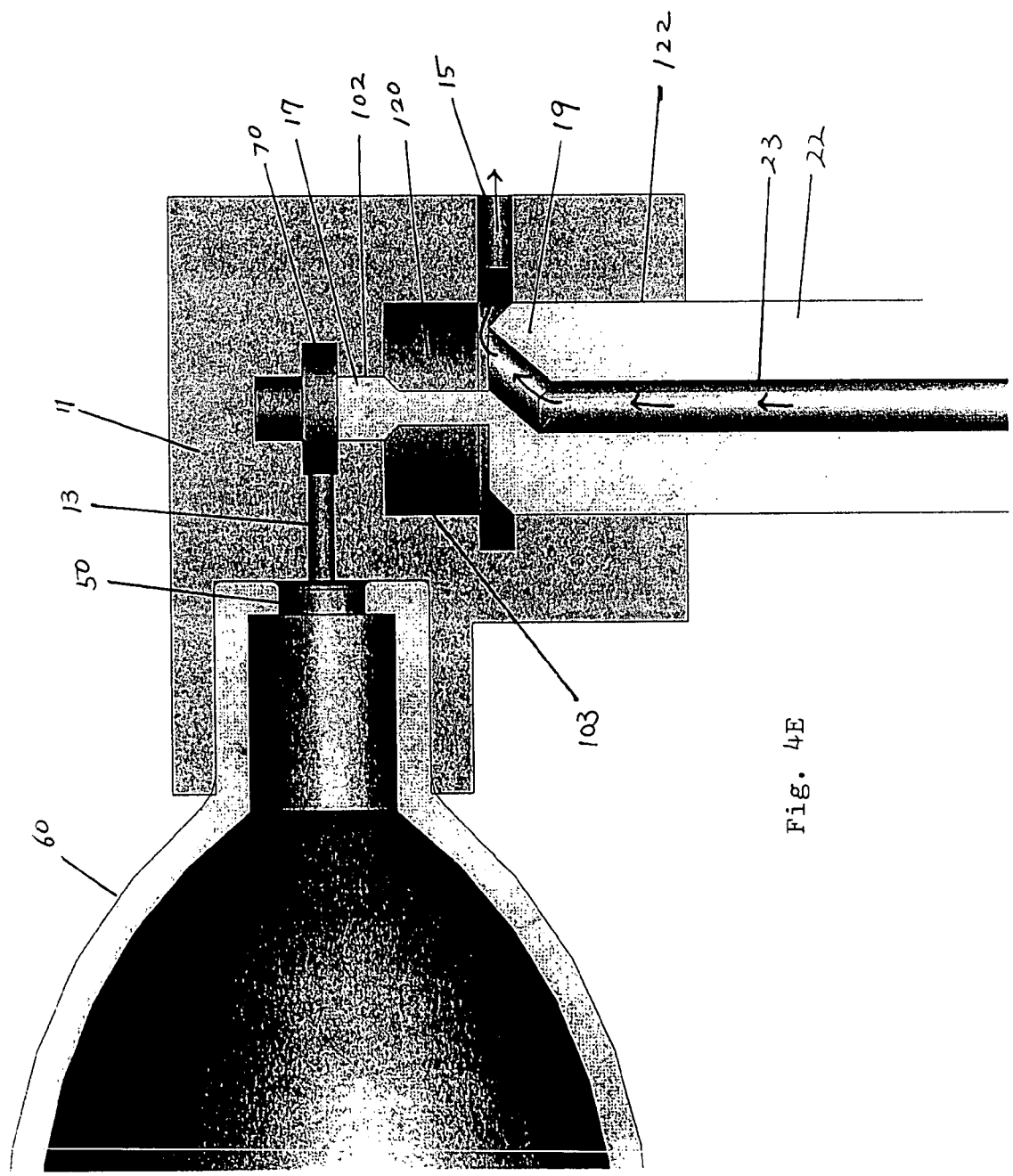
FIG. 4E is a perspective view illustrating a final position (returning to original state with source valve back to closed position and vent valve back to open position so that gas moves from barrel space to gas outlet port following the arrows) in the operation of the first embodiment for the power-assisted syringe illustrated by FIG. 1.

In a reverse manner also (as illustrated in FIGS. 3D and 4E), in the absence of any pressurized gas being released from the source 60—and with the source valve 17 being in the closed position and the vent valve 19 in the open position— such pressurized gas as may be present at any time within the spatial volume of the barrel lumen 34 can pass through the apertures 80 and enter the hollow channel 23 of the plunger tube member 22; then travel upwardly through the hollow channel 23 over the linear length of the plunger tube member 22; and then exit the plunger tube member 22 into and travel through the vent valve 19 within the valve housing 11 for subsequent release and exhaust via the gas outlet port 15 into the ambient environment.

The Essential Operation of the Power Assisted Syringe Device:

FIGS. 4A-4E and analogous cross-sectional FIGS. 5A-5E respectively show the operation of the power assisted syringe of FIG. 1 and illustrate several stages of valve openings resulting from an operator applied and controlled force upon the valve housing assembly.

Figure 5A:
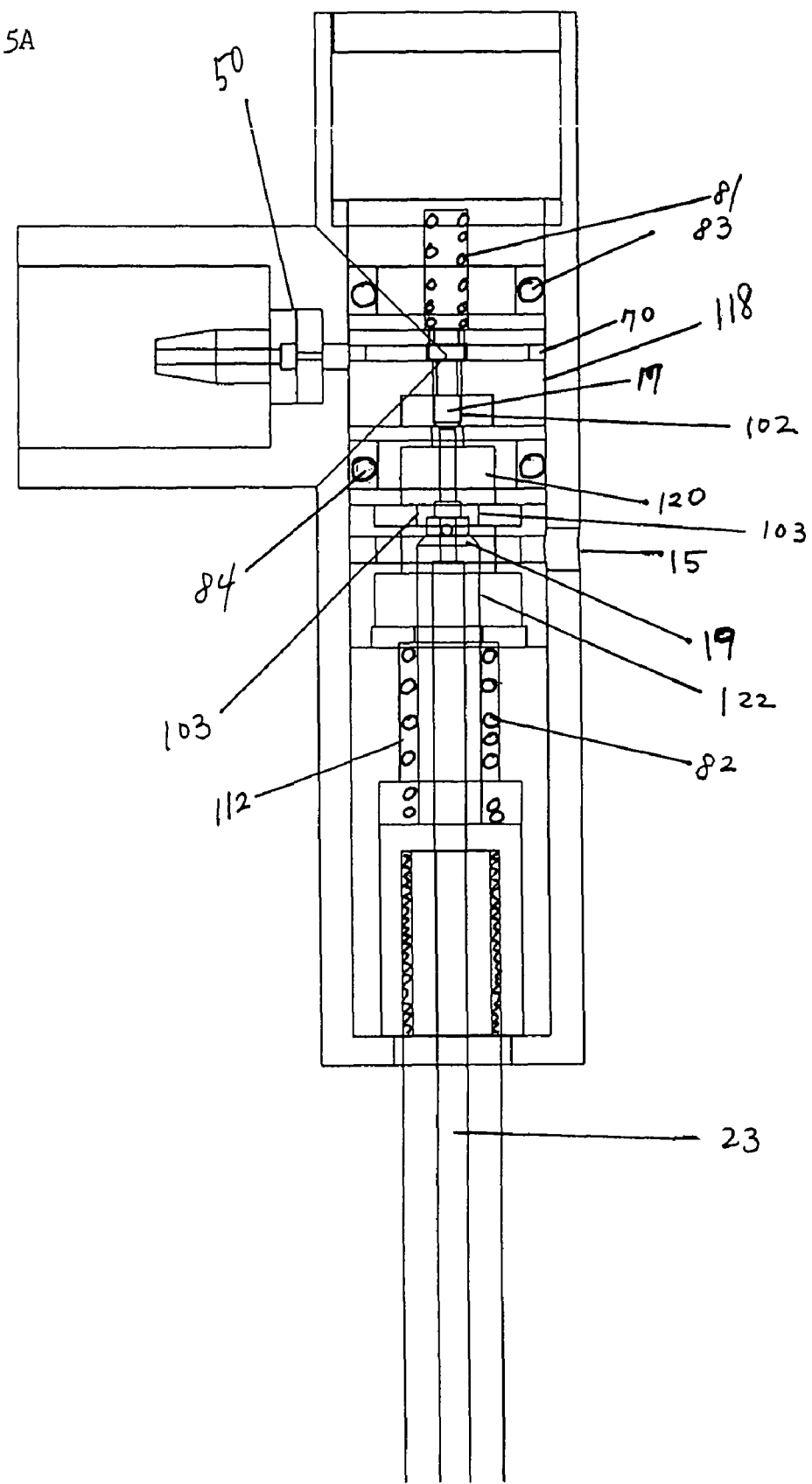
FIGS. 5A-5E show detailed cross-sectional views of the valve operations for the power-assisted syringe of FIGS. 4A-4E, respectively (arrows indicate the fluid gas movement)

FIGS. 4A and 5A respectively show the power-assisted syringe at the stage when no manual pressure or force is being applied by the operator to the valve housing. As seen therein with a schematic cross-section view, the locations of a source valve 17 and a vent valve 19, the plunger tube member 22, and the gas vent port 15 within the interior of the valve housing 11 are indicated.

As shown particularly by FIG. 5A, the locations for the vent valve 19 and the source valve 17 are seen in their aligned position; and one or more bias springs 81, 82 respectively bias each of these valves in their respective positions when no operator force is applied. The source valve 17 is shown as being in the closed position within the valve housing 11, as illustrated in FIGS. 4A and 5A; and the source valve sealing surface 102 is shown as an interface surrounding the perimeter of the source valve 17 within the valve housing 11. The vent valve 19, however, is shown as being in the open position by FIGS. 4A and 5A; and the vent valve sealing surface 103 is also seen as lying within the valve housing 11.

It also will be recognized from FIGS. 1 and 4A that the internal lumen (barrel space) 34 of the barrel tube 32 serves as an open communication pathway for moving the plunger assembly 20 in either direction (forwards or backwards) within the barrel assembly 30; and that the barrel space 34 provides an unrestricted passageway for the flow of fluid with negligible flow resistance between the valve working volume 120 and the working fluid volume capacity of the syringe device at all stages of valve operation. The proximal end of the plunger tube serves as the vent valve 19. The plunger guide bearing surface 122 provides proper alignment of the source valve 17 and vent valve 19 when force is applied to the valve housing 11.

Figure 5B:
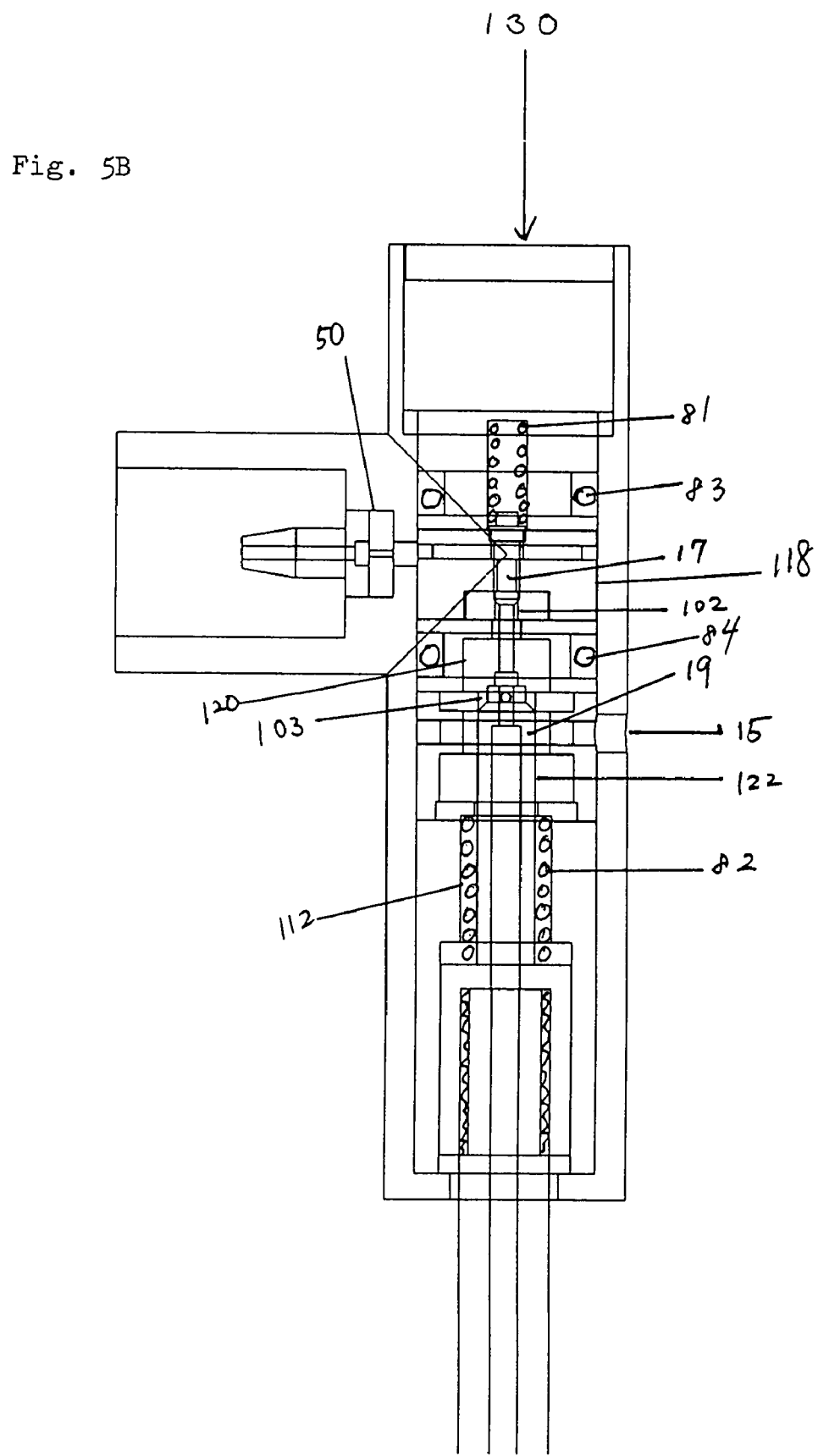

FIGS. 4B and 5B illustrates the initial result of applying a hand-generated force 130 to the top of the valve housing 11. As shown therein, the plunger member 22 (having a hollow channel 23) is axially displaced a short distance, with the plunger guide bearing surface 122 aligning the movement into the interior of valve housing 11. This movement causes substantive identical displacements at the source valve 17 and vent valve 19. When the plunger member 22 is slightly displaced as illustrated in FIG. 4B, the vent valve 19 makes initial contact with the vent valve sealing surface 102, and this results in contact closure of the gas outlet port (or exhaust vent) 15. The source valve 17 now also has reduced contact with the source valve sealing surface 102, as compared to its position within FIG. 4A.

The Different Sources of Dead Band:

The difference in valve position seen by comparing FIGS. 4A and 4B illustrates the first of three different sources of "dead band". Structurally, dead band is the difference between the displacement changes occurring within the valve housing assembly 10 and the positional displacements of the plunger assembly 20 when a force 130 is applied to the top of the valve housing 11. This first source of dead band is determined by the amount of flow area required to rapidly vent pressurized gas from the plunger assembly working volume when the operator stops applying force (i.e., contrast medium injection is complete). For example, the dead band of FIG. 4B may be 0.010 to 0.030 inches of axial displacement. However, the displacement can be controlled at the time of manufacture to be any desired distance. For example, the dead band displacement could be decreased as far as possible so long as performance is not substantially affected.

Figure 5C:
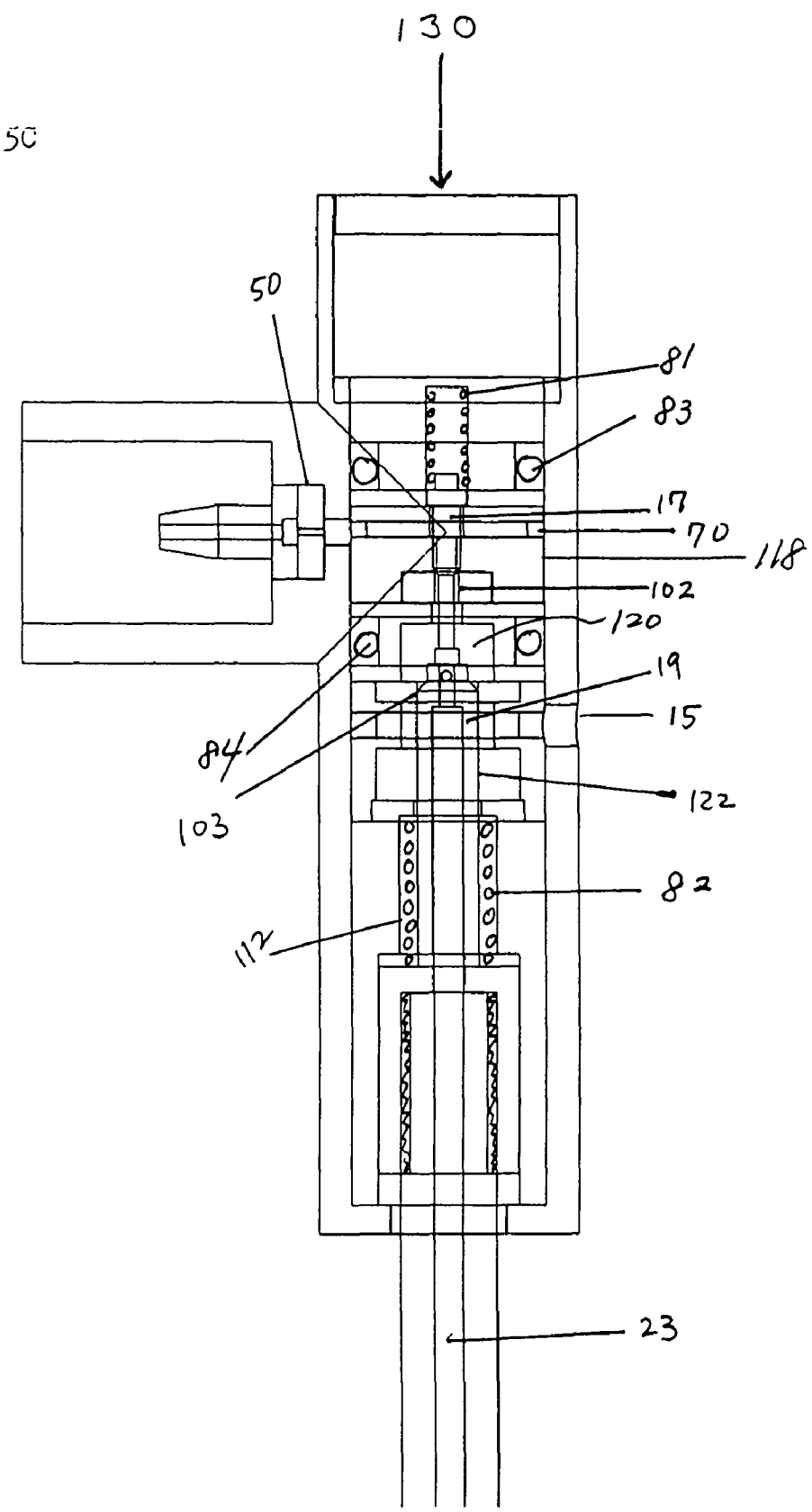

FIGS. 4C and 5C show the situation when the plunger member 22 has been displaced farther in distance and position than that seen in FIG. 4B. As seen in FIG. 4C, the vent valve 19 has increased contact with the vent valve sealing surface 103, but the source valve 17 now has only limited closure contact—i.e., it has been forced upwards into the valve housing by the positional change. The plunger member displacement illustrated by the positional differences for the needle valve positions seen in FIGS. 4B and 4C represents the dead band associated with the closing of the gas outlet by the vent valve immediately before opening the source needle valve into the communication with the gas inlet 13. This second source of dead band may be 0.005 to 0.015 inches of displacement distance. However, it can be controlled at the time of manufacture to be any desired distance. For example, the vent valve dead band could be decreased as far as possible so long as performance is not affected. Overlap of the source valve and vent valve should be decreased as much as possible or eliminated to improve the issues with deadband.

Figure 5D:
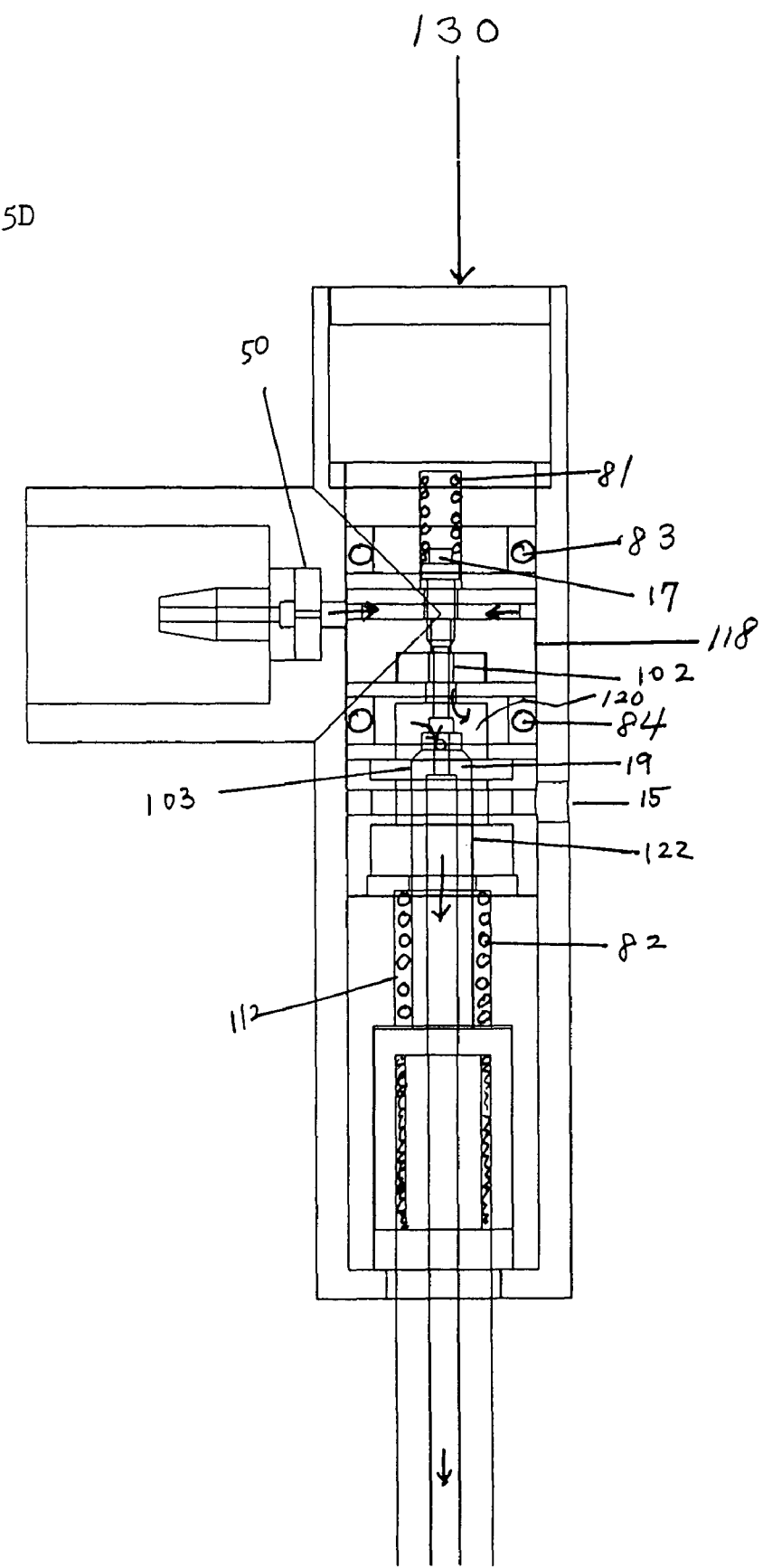

FIGS. 4D and 5D illustrate the open valve position for the regulatory source valve 17 which no longer has contact with the source valve guide bearing surface 102. Only subsequently will there be an introduction and flow of pressurized gas (vapor pressure) 60 through the gas inlet 13, the hollow channel of the heat exchange passage 70, the exposed source port 28 (a by-pass flow passage via the space between the perimeter of the source needle valve and source sealing surface), the valve working volume 120 (the space between the vent valve sealing surface 102 and the vent valve 19), the hollow channel 23 of the plunger 22, and the barrel space 34 of the barrel 32 (see the arrows indicating flow passage of gas).

The displacement of the plunger assembly 20 as a whole is best illustrated by the difference in position of the source valve 17 with respect to the plunger member 22. The positional differences seen between FIGS. 4C and 4D represent the continuously variable cross sectional area between the perimeter of the source valve 17 and the source valve sealing surface 102 for gas flow passage created by the movement of the source valve 17. Increasing or decreasing the applied force upon the valve housing 11 correspondingly increases or decreases, respectively, the cross-sectional area of the source port 28 for fluid flow. This increase or decrease in cross-sectional area also results in a dead band. The size of the dead band depends upon the cross-sectional area for flow required to achieve a desired injection rate of contrast medium—which depends on other parameters, including catheter size, orifice size, and the numbers and locations of side holes of the catheter, etc. This third source of dead band can be as little as 0.001 inches or as much as 0.030 inches in displacement distance, depending on the load. It can be also controlled at the time of manufacture to be any desired shape, size and length of the source valve. For example, the dead band could be decreased so long as performance is not affected.

Finally, when the act of power-assisted contrast medium injection is completed, the hand-generated manual force 130 previously applied to the top of the valve housing 11 is voluntarily terminated by the operator; and the axial displacement of the gas source valve 17 and the gas vent valve 19 becomes immediately reversed—via the biased springs contained within each of these regulators. The reversal result is an immediate return to the original position and alignment illustrated herein by FIGS. 4E and 5E.

Figure 5E:
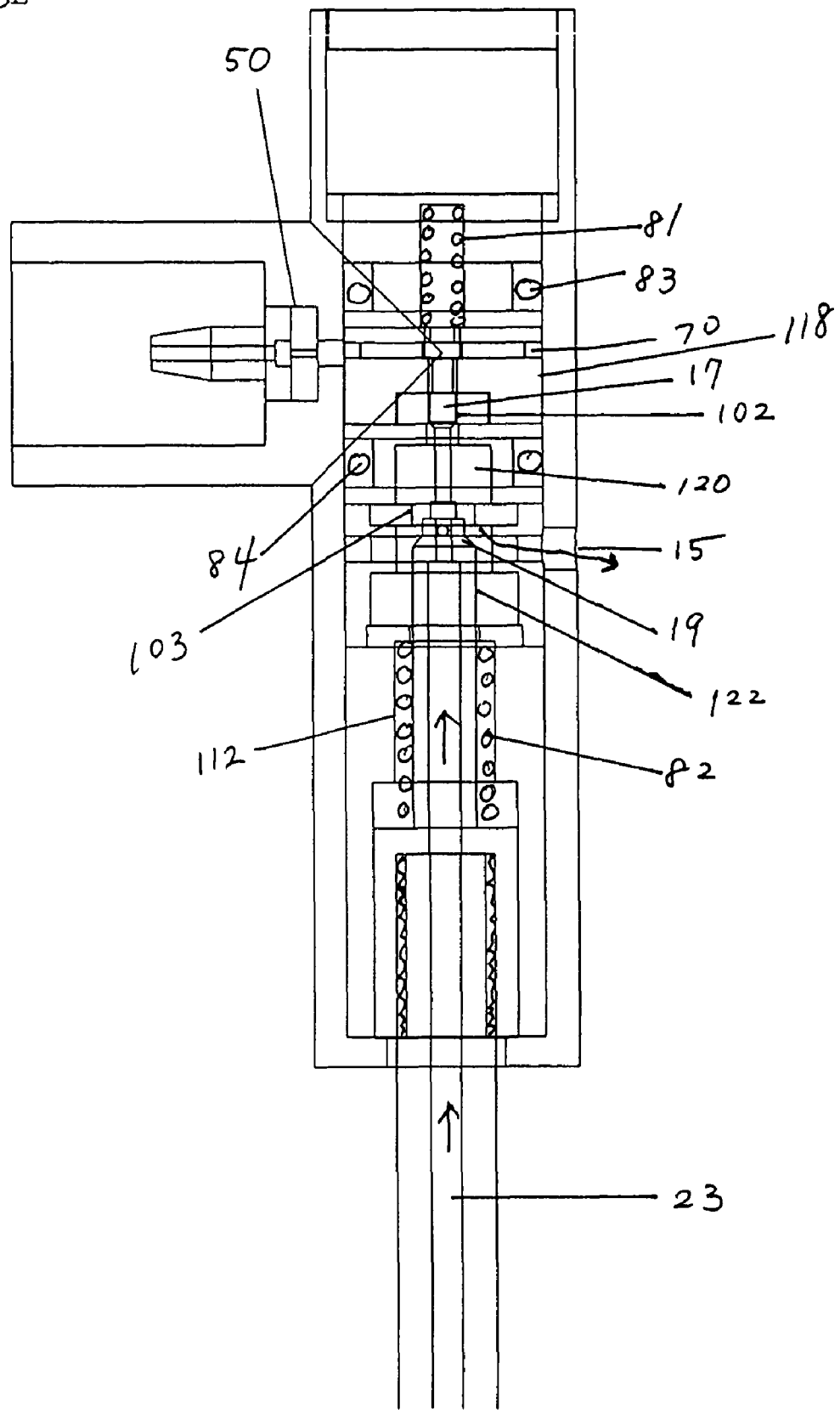

FIGS. 4E and 5E illustrate the closed source valve position, with the source valve 17 being in full contact with the source valve guide bearing surface 102, and the vent valve 19 being in an open valve position. The gas flows from the barrel space 34 through the hollow channel 23 of the plunger member 22 and the gas outlet port 15 into the ambient space (see arrows indicating flow passage of the gas) when the force previously applied to the top of the valve housing 11 is terminated, an event which occurs when the act of contrast medium injection is completed.

The Gaseous Pressure Force:

In the preferred embodiment, the source of pressurized gas 60 (shown by FIGS. 1 and 4A-4E respectively) provides the vapor pressure force and supplies the power assist to the syringe device. The pressurized gas typically is in a liquefied state and has a known or easily determinable vapor pressure. The pressurized gas provided by the source 60 in liquefied form maintains a constant vapor pressure while the liquefied gas remains in its source container. No pressure or gas controlling mechanism is required for the source.

The pressure force (vapor pressure) provided by the source is maintained until all the liquefied gas is expended and exhausted, at which point the container source 60 can be physically removed and easily replaced. Those persons ordinarily skilled in this technical field will appreciate that vapor pressure is a function and direct variable of the temperature of the liquefied gas in the source container. For example, at 68 degrees F (room temperature), liquefied $CO_2$ will have a vapor pressure that is sufficient to provide an operating pressure force of up to approximately 800 psi.

In most embodiments, the power-assisted syringe of the present invention will allow for the easy transferability of a source of pressurized gas, preferably as a conventional miniature $CO_2$ cartridge or gas canister. The pressurized gas supply will typically comprise a metallic canister or cartridge that may be transported, stored, and optionally used at room temperature or in any other (warmer or colder) environment. Suitable (miniature sized) canisters will hold quantities of liquid gas fluid that are sufficient to perform the conventional range of medical procedures.

In preferred embodiments, it is particularly desirable that a miniature pressurized-gas cylinder (or gas cartridge), such as a $CO_2$ cylinder, be directly integrated into the power-assisted syringe as the source of liquefied gas. The attachment components required for mechanical integration and installation of a miniature gas cylinder into the syringe device would typically include a piercing component to open the pressurized fluid container; a sealing component to prevent leakage of pressurized fluid; and a force applying component, such as threads, to press the pressurized fluid container against the sealing component to prevent leakage. The disposable cartridge has a frangible seal, and the seal may be breached by a fitting which threadably engages a casing in which the cartridge is received. The fitting may include a sealing body such as a rubber washer to avoid leakage of fluid, while the fitting and casing may include gripping surfaces to facilitate breaching the seal. In alternative embodiments, a miniature pressurized-gas cylinder can be installed internally within the shaft of the plunger or integrated with valve housing assembly internally within the shaft of the plunger.

Optional Additional Components:

A number of additional components may optionally added and be fully integrated into the power assisted syringe device. For example, a flow limiting means, such as an orifice valve, may be used to restrict or to control fluid flow from the pressurized-fluid container, thereby preventing the contrast flow rate from exceeding a maximum value or regulating the injection rate of contrast medium with a gauge. In a preferred configuration, the orifice valve is of fixed size.

Also, because the fluid from the pressurized-fluid container source may be in a two-phase state and/or at a reduced temperature, it is desirable to have heat exchange means to warm the gaseous fluid at the interface. Additionally, such heat exchange means may include flow passages within the syringe device. Such flow passages may be integrated into high heat capacity components and/or into components designed for high heat transfer to the environment.

In addition, the apparatus will often include other specific mechanisms and features for controlling the flow rate of gas—such as flow resistant valves, surge volume chambers, and/or pressure relief valves—with or without being programmed by incorporated computer chips/microprocessor controllers or other electronic control systems, a solenoid valve, a rotatable valve, a timing switch, a timing circuit, a pneumatic ram, a flow interrupter, and a flow gauge and controller used in combination.

Furthermore the needle valves are often designed with a metal needle (generally brass, bronze, or stainless or other alloys of steel) and an elastomeric seat (generally PVC, CPVC, PTFE, or use a wide range of brand name plastics and thermoplastics). While this is the most common form, some regulatory valves are available that have metal-metal, plastic-plastic, or plastic-metal needles and seats. These variations can be designed with specific applications in mind, especially situations where corrosion, high or low temperatures or extensive wear are possible as well as with various modifications in their configuration for different situations. These include threaded, socket-weld or buttweld, push on, solder end, clamp, grooved end, flangeless wafer-style, lugged, mechanical joint, and flanged. Additional optional components such as actuator system may be integrated into the power assisted syringe device. Valve actuation methods for control valves may include electric, pneumatic, hydraulic, and manual methods. The valve system also may have a valve actuated by a piezoelectric, magnetoresistive, or solenoid device to control the flow of fluid through the valve system.

Also, an actuator operatively may engage the valve member and is operable to selectively move the valve member to at least one of the closed and open positions to close and open the fluid orifice. Some control valves may come configured as a multi-piece design; and can include a small slight feed valve, a butterfly valve, a gate valve, a ball valve, a solenoid valve, a globe valve, a diaphragm valve, a pinch valve, a knife valve, a plug valve, a ball check valve, and a Barstock valve.

Flow controls (pneumatic) allow metered flow of fluid in one or both directions. A flow meter can be incorporated with valves such as needle valves, which are capable of accurate flow control. Flow controls (pneumatic) can also be configured in-line or at right angles. In an in-line configuration, the inlet and outlet ports are on the same axis. In a right angle configuration, the inlet and outlet ports are perpendicular.

Choices for pneumatic flow controls may include unidirectional (one-way), bi-directional (two-way) or three-way. In a one-way configuration the valve permits metered (restricted) flow in one direction and free flow in the reverse direction. In a two-way configuration, the valve provides for metered (restricted) flow in both directions. In a three-way configuration, the control provides flow control in three directions.

The present invention also may utilize mechanisms and features to supply and inject contrast medium fluid to the patient,—such as an injection syringe, a pressure gauge, a flow resistance valve, Joule-Thomson valve, stopcocks, and connecting tube. All of these are also commonly used in combination to provide fluid to the patient. The apparatus also would include mechanisms and features for providing a continuous flow of fluid through the catheter using a flow resistance valve and stopcock, which flushes out residual fluids (e.g., blood, saline).

Further Operational Details of the Power Assisted Syringe Device:

To better illustrate the operation of the power assisted syringe shown in FIGS. 1-3 respectively, views of several stages of valve operation are presented by FIGS. 4A-4E respectively. Also, the views illustrated by FIGS. 5A-5E are analogous to views shown by FIGS. 4A to 4E respectively.

Shown within FIG. 5A are a source valve spring 81 and a vent valve spring 82, which are used to bias the plunger member 22 in the desired position. FIG. 5B also illustrates a heat exchange passage 70, which is formed by a circumferential groove in the source housing 118. At least one radial flow passage connects this circumferential passage with the source valve 17.

Thus, during assembly of the power assisted syringe device, the source housing 118 is installed with at least one radial flow passage, with the source housing 118 being located preferentially one-hundred-eighty (180) degrees [in theory, in a range of 1 to less than 360 degrees; or in solenoid form] from the high-pressure cylinder inlet. In this way, the two-phase fluid exiting the cylinder (and passing through the orifice) must travel 180 degrees around the circumference of the source housing 118 before entering the radial flow passage(s). All of these passages provide heat exchange surfaces by which to warm the fluid and to convert the two-phase fluid to a gaseous state.

Note also that in an alternative embodiment, the heat exchanger can be incorporated into the parts other than valve housing assembly such as gas canister (cartridge), within the adaptor of gas canister, between the gas canister and valve housing assembly, as a separate structure or unit or can be installed in the form of filter, micro-turbine, nozzle or film such as Kapton heater film.

2. A Preferred Second Embodiment

A second embodiment of the power-assisted syringe is illustrated by FIGS. 6-9 respectively. This second embodiment is structurally and functionally similar in every respect—but two—to the first embodiment described above. The substantive differences are: (i) a plunger tube member in the plunger assembly which, for most of its linear length, is only slightly smaller in dimensions and internal spatial volume than the size and volume of the lumen in the barrel assembly; and (ii) the pressurized gas from its source is directed into and is contained solely and exclusively within the hollow channel of the plunger tube member without ever entering into the lumen of the syringe barrel as such.

Figure 6:
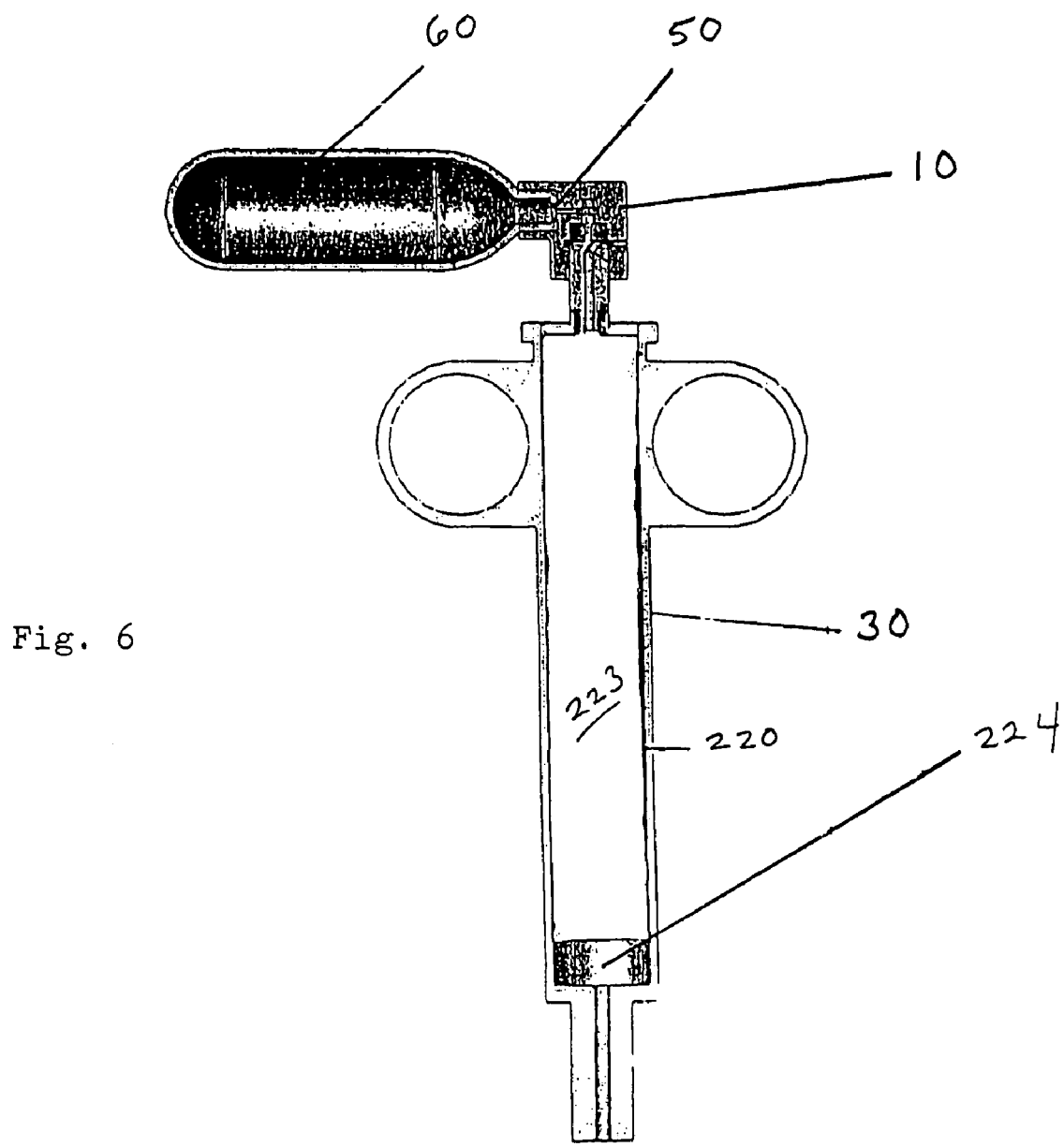
FIG. 6 is a perspective cross-sectional view of a second embodiment for the power-assisted syringe configuration of the present invention.
Figure 7:
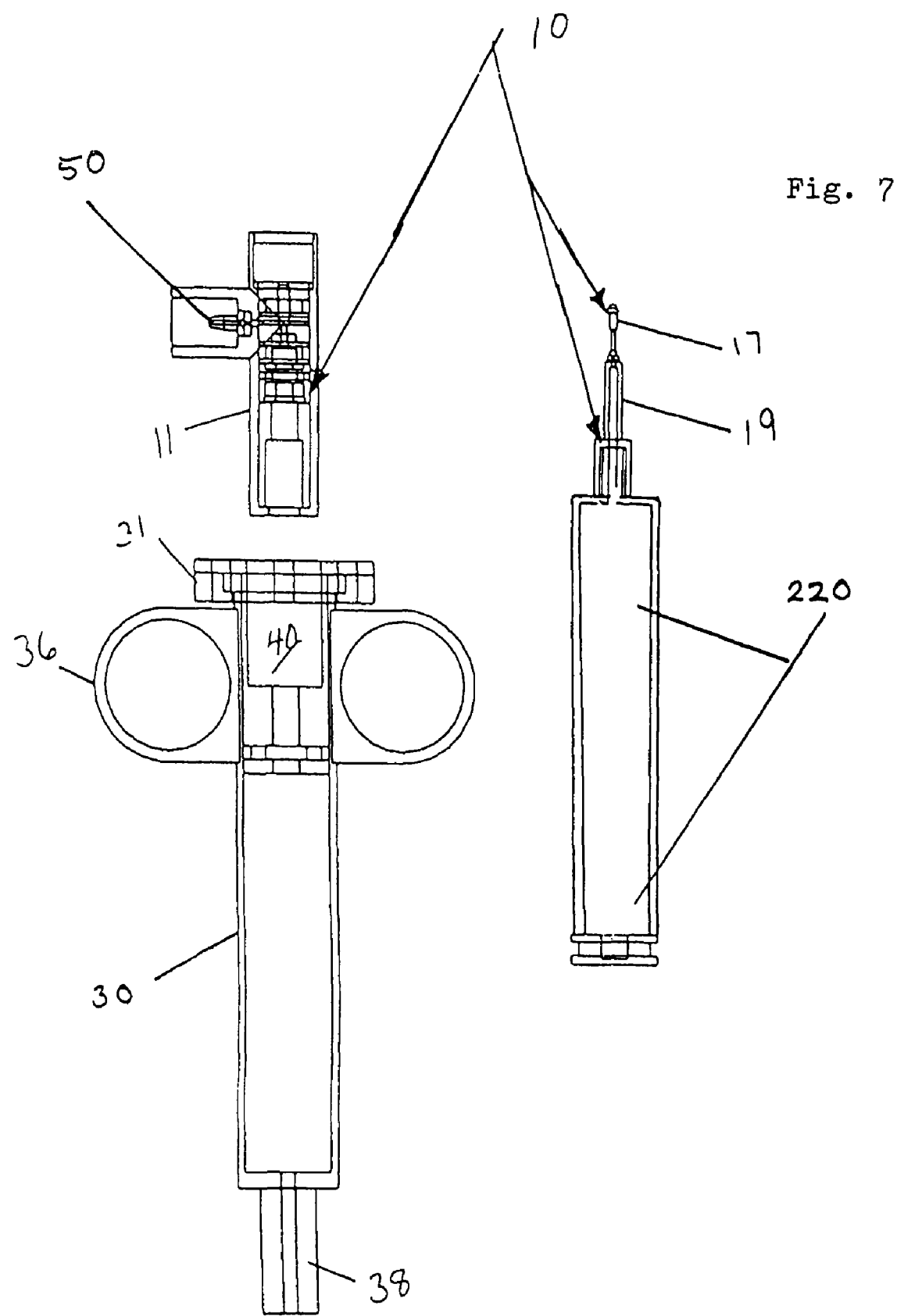
FIG. 7 is a schematic view of the disassembled second embodiment for the power-assisted syringe illustrated by FIG. 6.
Figure 8:
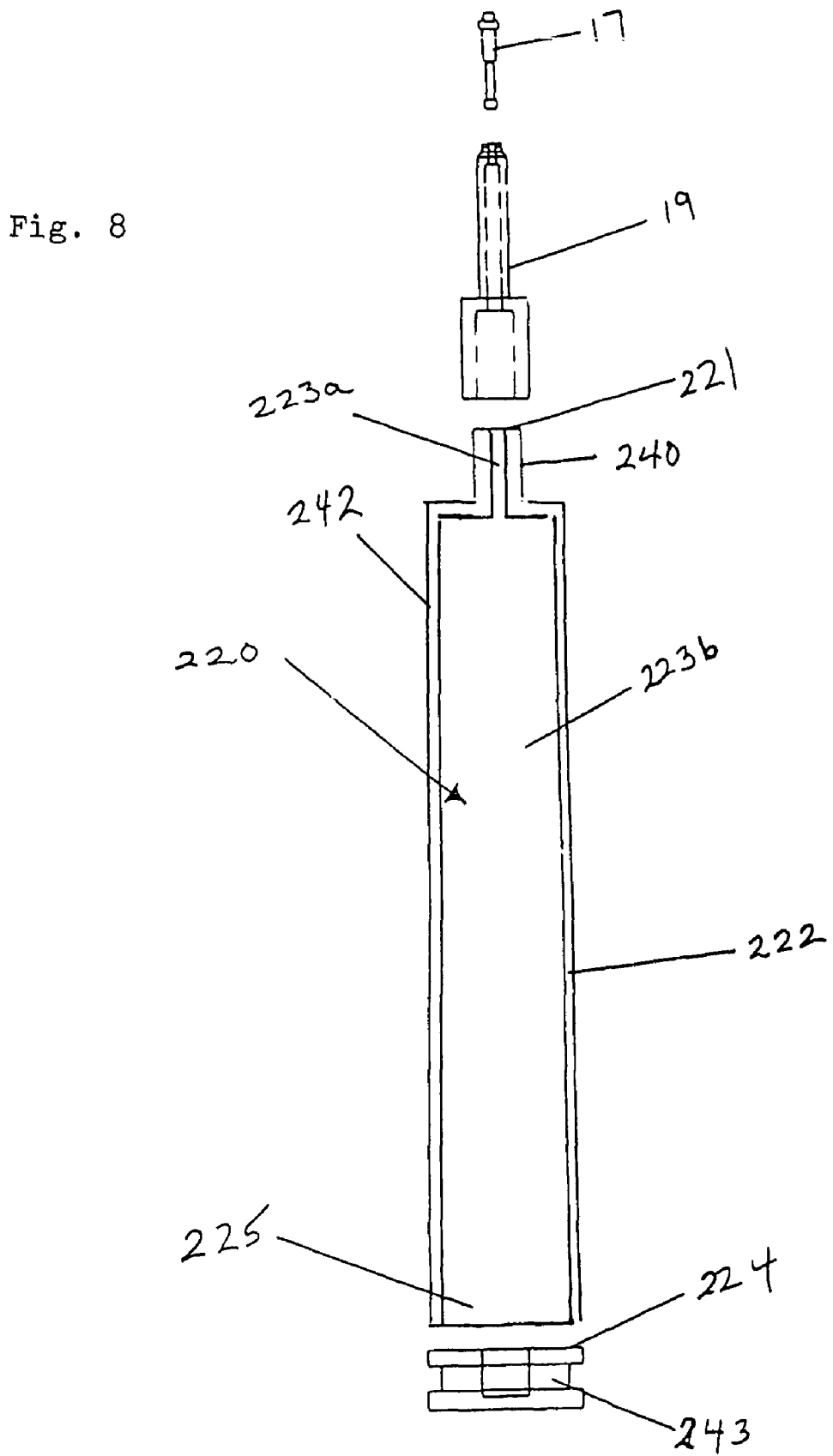
FIG. 8 is a view of the plunger assembly with the source valve and vent valve of the second embodiment for the power-assisted syringe illustrated by FIG. 6.

FIG. 6 presents a perspective view off this second embodiment for the assembled power-assisted syringe; and FIG. 7 schematically shows the component parts of the unassembled power-assisted syringe. As seen therein, the portable and self-contained power assisted syringe comprises a manually controlled valve housing assembly 10, a plunger assembly 220, a syringe barrel assembly 30, attachment means 50 for connecting a portable source of pressurized gas to the value housing assembly 10, and a portable pressurized gas source 60 (seen as a miniaturized gas cylinder). The valve housing assembly 10 is connected via attachment means 50 to the pressurized gas source 60 and will receive a gaseous pressure force directly from the gas source 60 through the heat exchange passage. The valve assembly 10, in turn, is connected to the plunger assembly 220; and is able to direct and to deliver pressurized gas on-demand to the interior of the plunger assembly 220. The plunger assembly 220, in turn, lies within and can pass axially through the linear length and interior spatial volume 34 of the syringe barrel assembly 30. FIG. 8 reveals the relationship of the plunger assembly 220 with respect to the source valve 17 and the vent valve 19. FIG. 8 is thus directly comparable to FIG. 3D described previously herein (for the first embodiment), but shows the dimensions and spatial volume of the hollow channel 223 of the plunger tube member 222 to be far larger in size.

The plunger assembly 220 shown in FIG. 8 comprises a plunger tube member (or push rod) 222 which has a narrow upper portion 240 and a broad lower portion 242. Within the narrow upper portion 240 is a centrally disposed hollow channel 223a, which extends axially only for a short distance. In comparison, the broad lower portion 242 is an elongated cylinder and has a large spatial volume 233b which extends over its linear length. At the distal end 225 of the plunger tube member 222 is a solid circular plunger plate (or piston) 224. The circular plunger plate 224 has a longitudinally spaced annular groove 243 around its perimeter and girth which will receive an O-ring, and thereby provide a fluid-tight seal for the plunger assembly while lying within the lumen 34 of the syringe barrel assembly 30.

Figure 9:
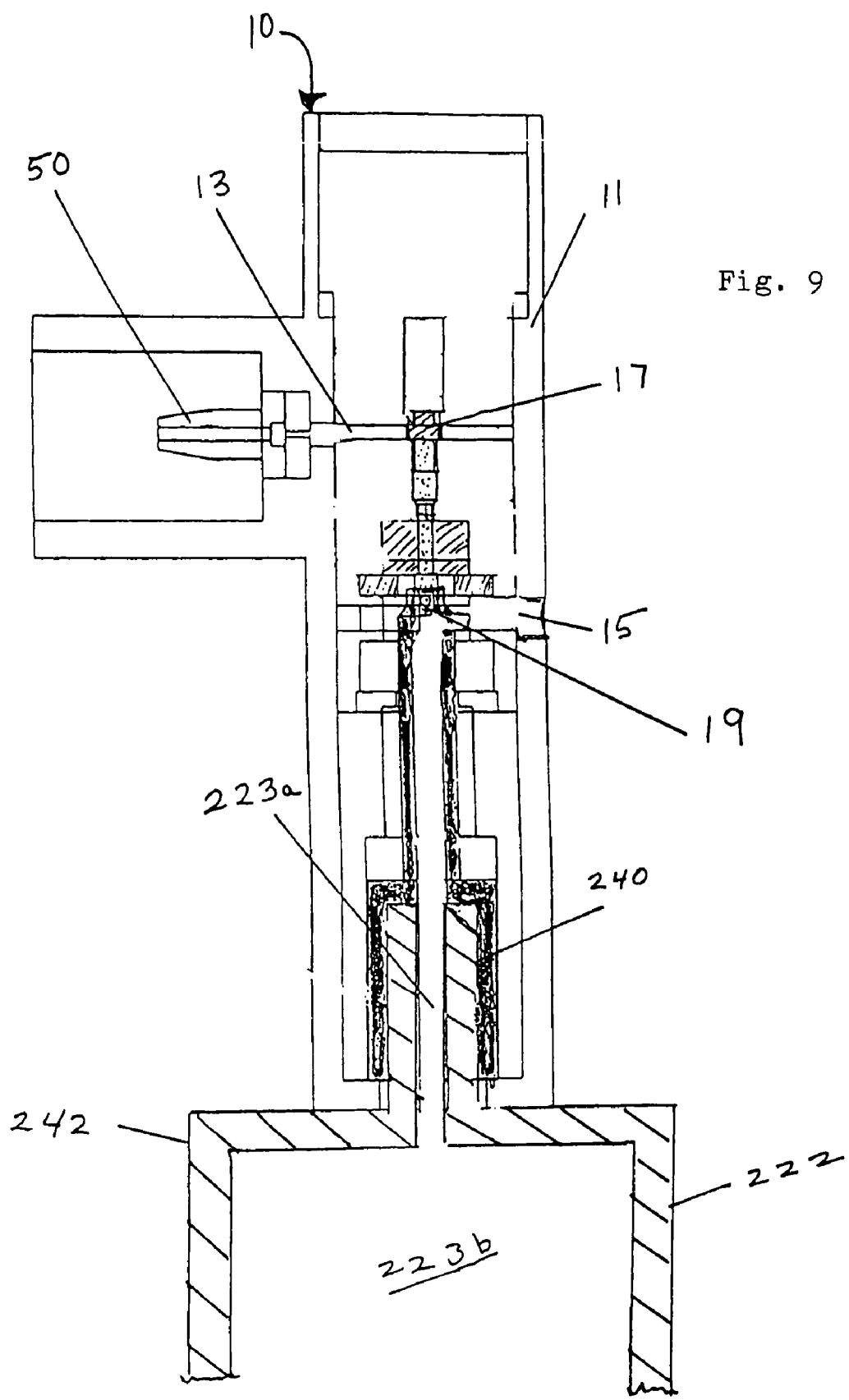
FIG. 9 shows detailed cross-sectional views of the valve housing assembly and the proximal part of the plunger assembly of the second embodiment in combination.

Also as seen in FIG. 9, the source valve 17 and the vent needle valve 19 are in stacked linear aligned position; are collectively joined together; and are in fluid flow communication with the hollow channel 233a disposed within the narrow upper portion 240 of the plunger tube member 222. In this manner, as illustrated by FIG. 5D, such pressurized gas as is introduced from the gas source 60 through the valve assembly 10 must pass through the hollow channel 233a and into the broad spatial volume 233b of the plunger tube member 222.

In this second embodiment, it will be recognized and appreciated that neither the plunger tube member 222 nor the plunger plate 224 have any apertures, exit holes, ports, or channels of any kind at the distal end 225. Accordingly, unlike the first embodiment of the present invention, there is no portal for nor escape of pressurized gas into the barrel lumen at any time after the gas enters and travels through the narrow hollow channel 223a and the broad spatial volume 233b of the plunger tube member 222. Thus, when pressurized gas is introduced from the gas source 60 through the valve assembly 10, it is always contained solely and exclusively within the narrow hollow channel 233a and the broad spatial volume 233b of the plunger tube member 222.

In the reverse manner also, in the absence of any pressurized gas being released from the source 60, such pressurized gas as may be present at any time within the broad spatial volume 223b of the plunger tube member 222; then travel upwardly through the narrow hollow channel 233a; and then exits from the plunger tube member 222 into and through the vent valve 19 and the gas outlet port 15 within the valve housing 11 for release into the ambient environment.

Another alternative modification of this preferred second embodiment is that a part of plunger tube member 222 can move forward or backward in a form of telescoping with at least one slidable part of the plunger member, or expandable/contractable plunger member within the barrel tube in response to internal gaseous pressure, which results in forward or backward movement of the piston of the plunger.

3. A Preferred Third Embodiment

A third embodiment of the power-assisted syringe is illustrated by FIGS. 10-13 respectively. This third embodiment is structurally and functionally similar in every substantive respect—but two—to the first embodiment described previously herein. The substantive differences are: (i) the valve assembly is attached to the syringe on the side of the barrel assembly; and (ii) the pressurized gas from its canister source is directed into and is contained solely and exclusively within the lumen of the syringe barrel as such—without ever entering into or travelling through the hollow channel of the plunger member in the plunger assembly.

Figure 10:
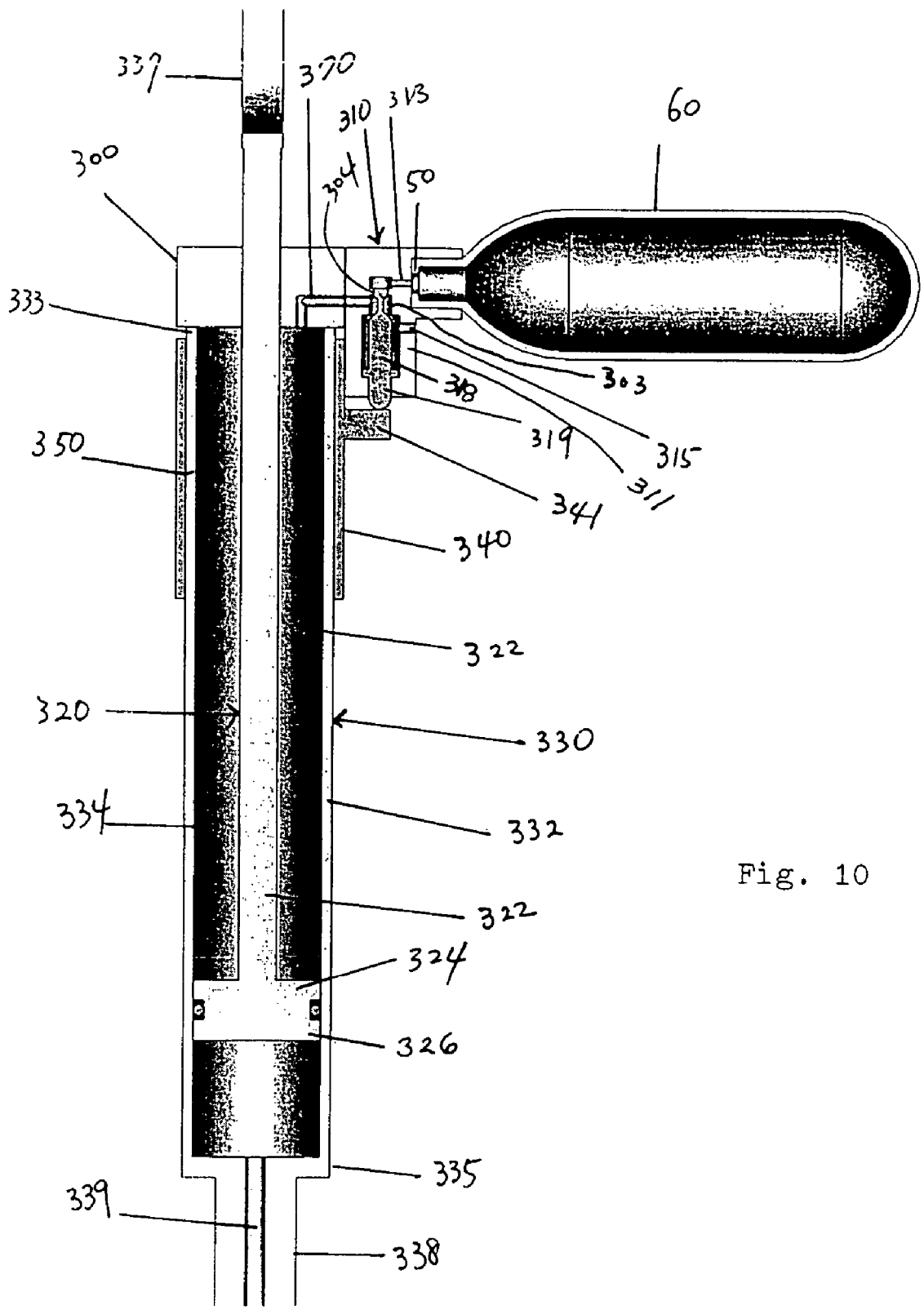
FIG. 10 is a perspective cross-sectional view of a third embodiment for the power-assisted syringe configuration of the present invention.
Figure 11:
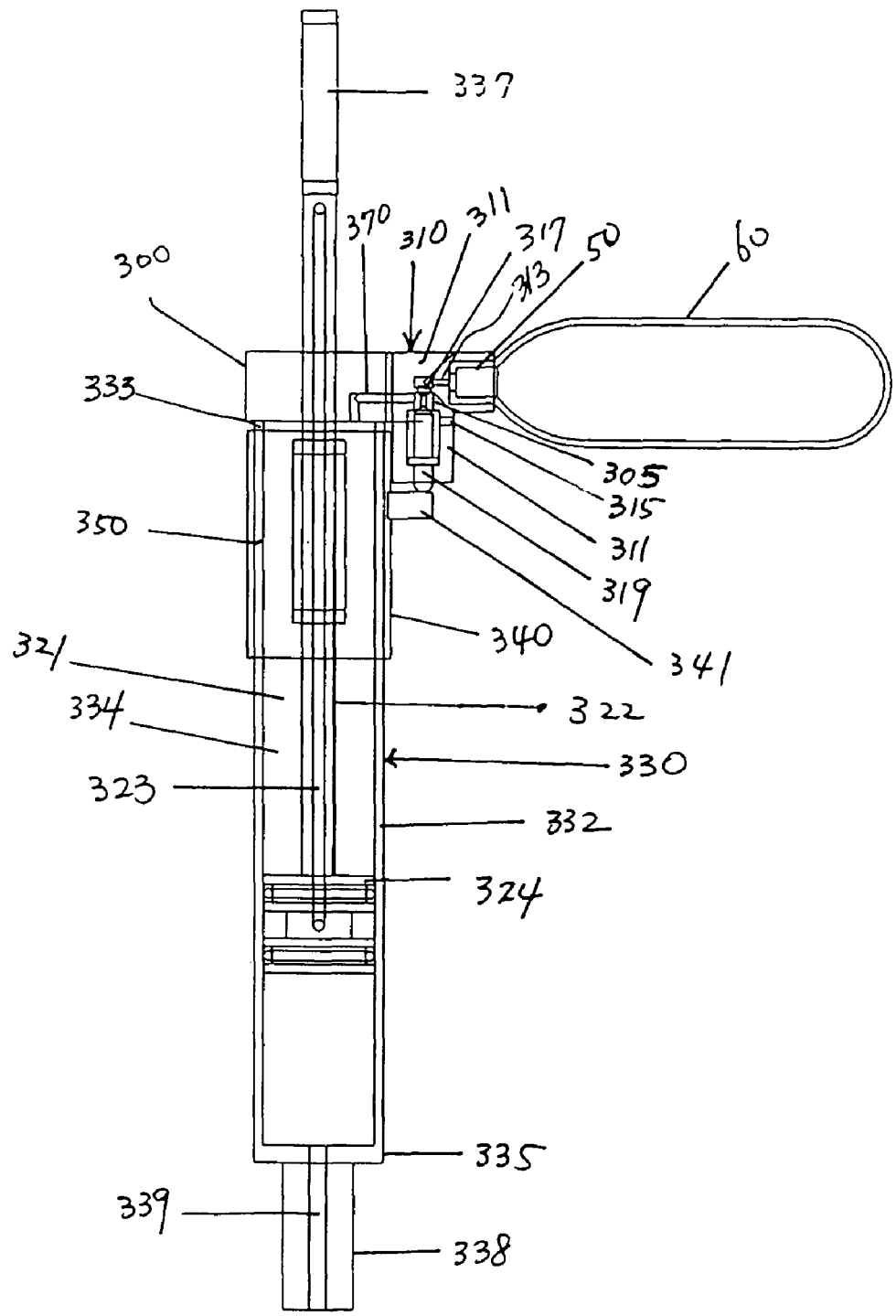
FIG. 11 is a side schematic view of the third embodiment for the power-assisted syringe illustrated by FIG. 10.
Figure 12A:
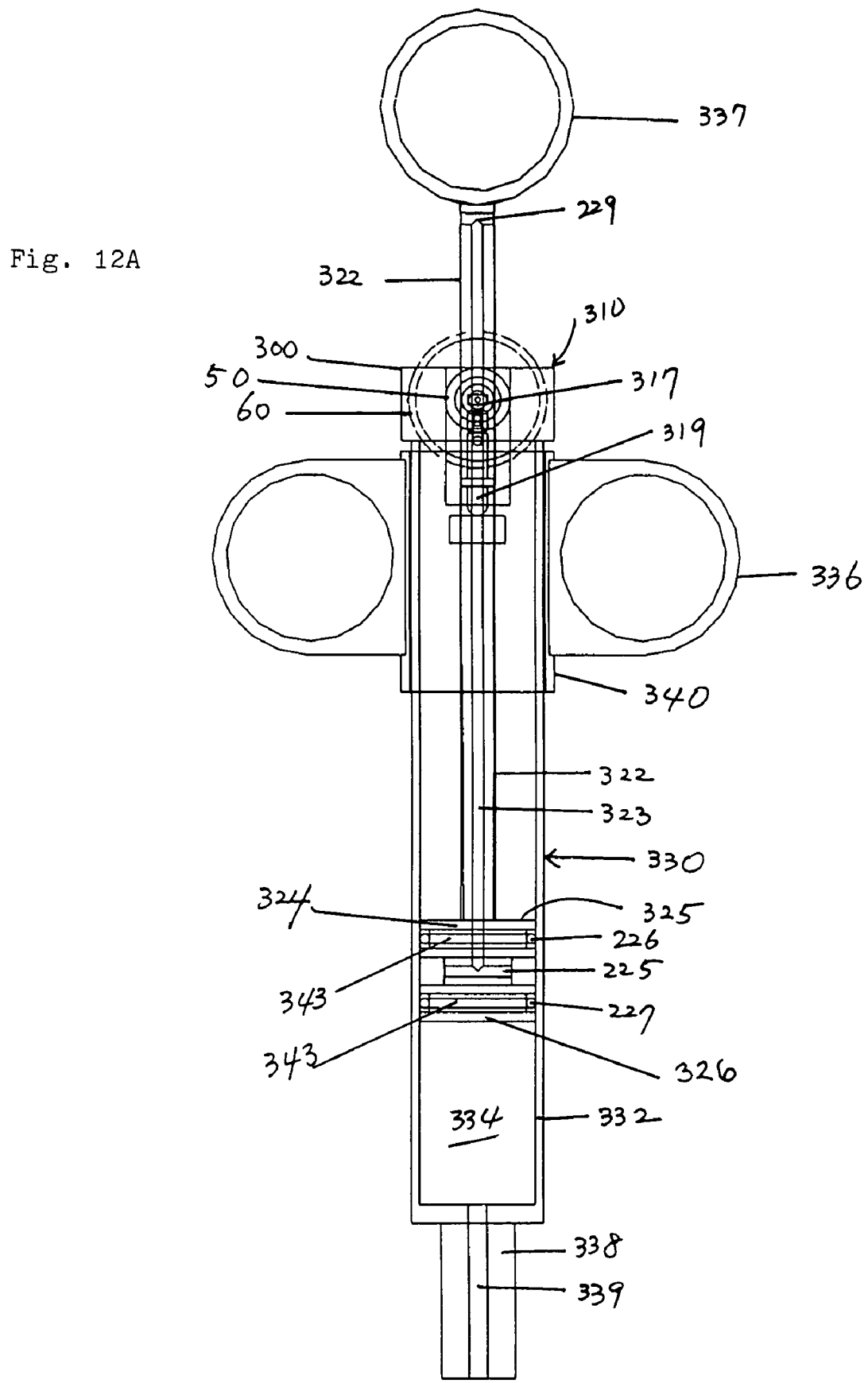
FIG. 12A is a front schematic view of the third embodiment for the power-assisted syringe illustrated by FIG. 10.
Figure 12B:
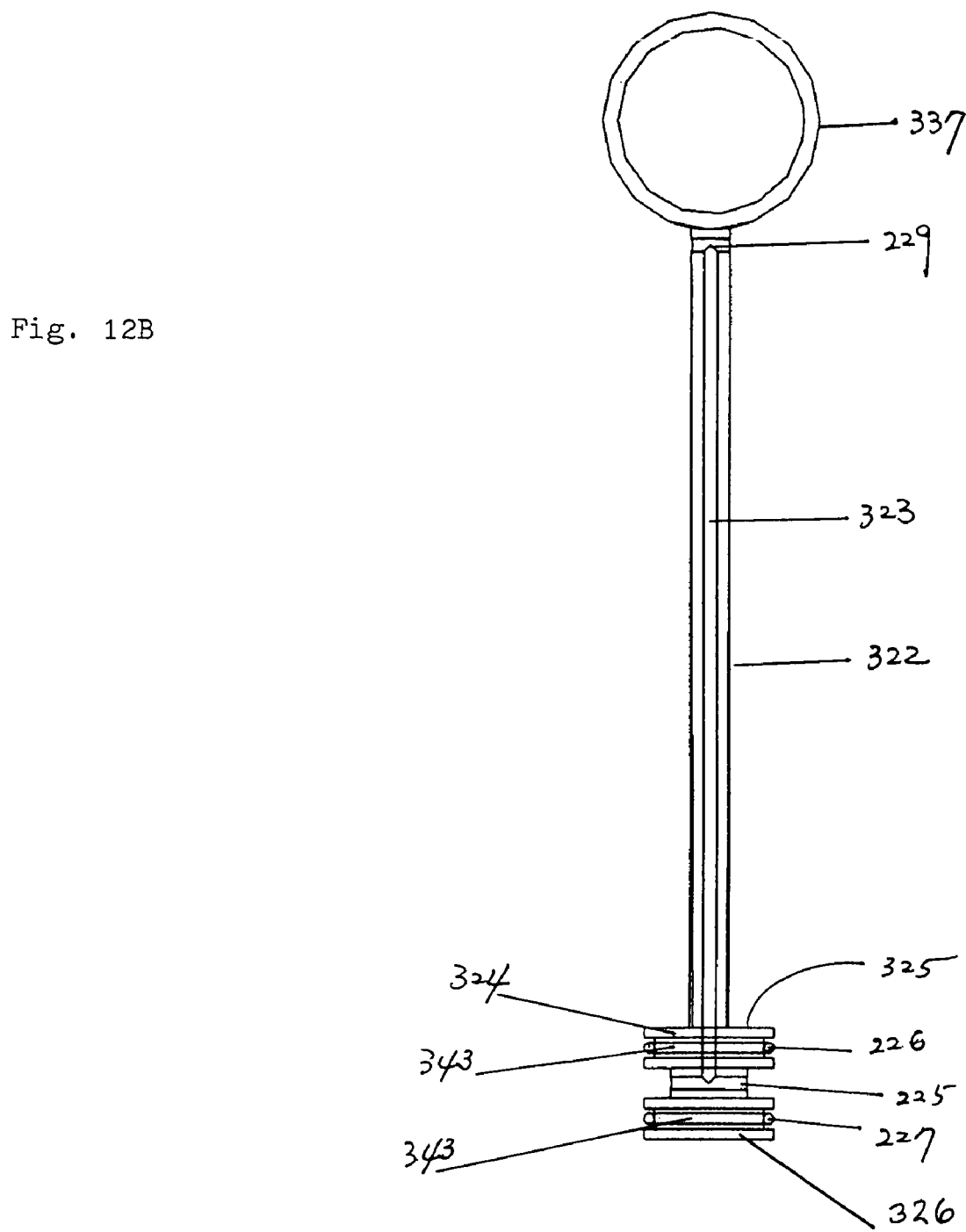
FIG. 12B illustrates the plunger assembly having a blow-by passage safety feature according to the third embodiment of the invention.

FIG. 10 illustrates a perspective view of this third embodiment for an assembled power-assisted syringe; and FIGS. 11 and 12 respectively schematically shows the component parts of an assembled power-assisted syringe in front and side cross-sectional views. As seen therein, the power-assisted syringe device has a slidable collar 340. The valve housing assembly 310 is attached on the side of the barrel assembly 330; and comprises a syringe barrel access channel 370; a gas inlet port 313, a regulating source (inlet) valve 317; a gas outlet port 315, and a regulating vent (exhaust) valve 318, each of which is contained within the valve housing assembly 310 attached alongside of the barrel assembly 330. The mechanism of gas containment and flow control is similar to that described herein for the first embodiment, except that the valve assembly is attached to the syringe on the side of the barrel assembly 330 in this third embodiment.

Details of the syringe barrel assembly 330 are shown by FIGS. 10-12 respectively. As seen therein, the syringe barrel assembly 330 comprises an upper barrel section 350, a barrel tube 332 having proximal and distal ends 333 and 335, and an elongated internal lumen 334. A nozzle 338 having an open passageway 339 is connected to the distal end 335 of the syringe barrel assembly 330 for the ejection of fluid by using the plunger assembly 320.

The manual operating means (such as one or more finger rings) are attached to a collar that is slidably positioned around the barrel. The manual force for injection is applied to the finger ring(s) 336 and a thumb ring 337 positioned on the syringe body and to the top of the plunger tube member 322, respectively; and is transferred to the sliding collar 340 that is positioned around the exterior of the barrel tube 332. Also, in one exemplified format of the third embodiment, a cap that closes the active gas space behind the plunger assembly 320 can be incorporated with the valve housing assembly 310.

The plunger assembly 320 comprises a plunger member (or push rod) 322 which can be entirely solid over its linear length; or, alternatively and optionally, have an elongated and centrally disposed hollow channel 323 extending axially over its linear length as illustrated in FIGS. 11 and 12. The plunger member 322 has two solid circular plunger plates 226 and 227, respectively joined at its distal end 325 [as seen in FIGS. 10-12 respectively]; and each circular plunger plate has a longitudinally spaced annular groove 343 around its perimeter and girth which will receive an O-ring, 226 and 227, respectively, and thereby provide a fluid-tight seal for the plunger assembly within the internal lumen of the syringe barrel. The plunger member 322 has two solid circular plunger plates 324 and 326, respectively joined at its distal end 325 [as seen in FIGS. 10-12 respectively]; and each circular plunger plate has a longitudinally spaced annular groove 343 around its perimeter and girth which will receive an O-ring, 226 and 227, respectively, and thereby provide a fluid-tight seal for the plunger assembly within the internal lumen of the syringe barrel.

The hollow channel 323 of the plunger tube member 322 may provide for a safety feature by the presence of a leakage or blow-by passage 225 positioned between two o-ring seals, first O-ring seal 226 and second O-ring seal 227, on the plunger tube member 322. The blow-by passage 225 allows for venting of gas that may leak through the first seal 226 to the ambient atmosphere. The vented gas travels through the passage opening 225, through hollow channel 323 of the plunger tube member; and then is released through the passage exit port 229 before it can potentially leak through the second o-ring seal 227 and become inadvertently injected into the patient. This blow-by passage feature can be also optionally incorporated in the first embodiment of the power assisted syringe.

As seen in FIGS. 10-12 respectively, the source (inlet) valve 317 and the vent (exhaust) valve 318 are in stacked aligned position and are collectively joined together in series. By this arrangement, there is a fluid flow communication and channel alignment in the valve housing assembly 310 which extends commonly among and is shared through the source (inlet) valve 317, and the vent (exhaust) valve 318.

Figure 13A:
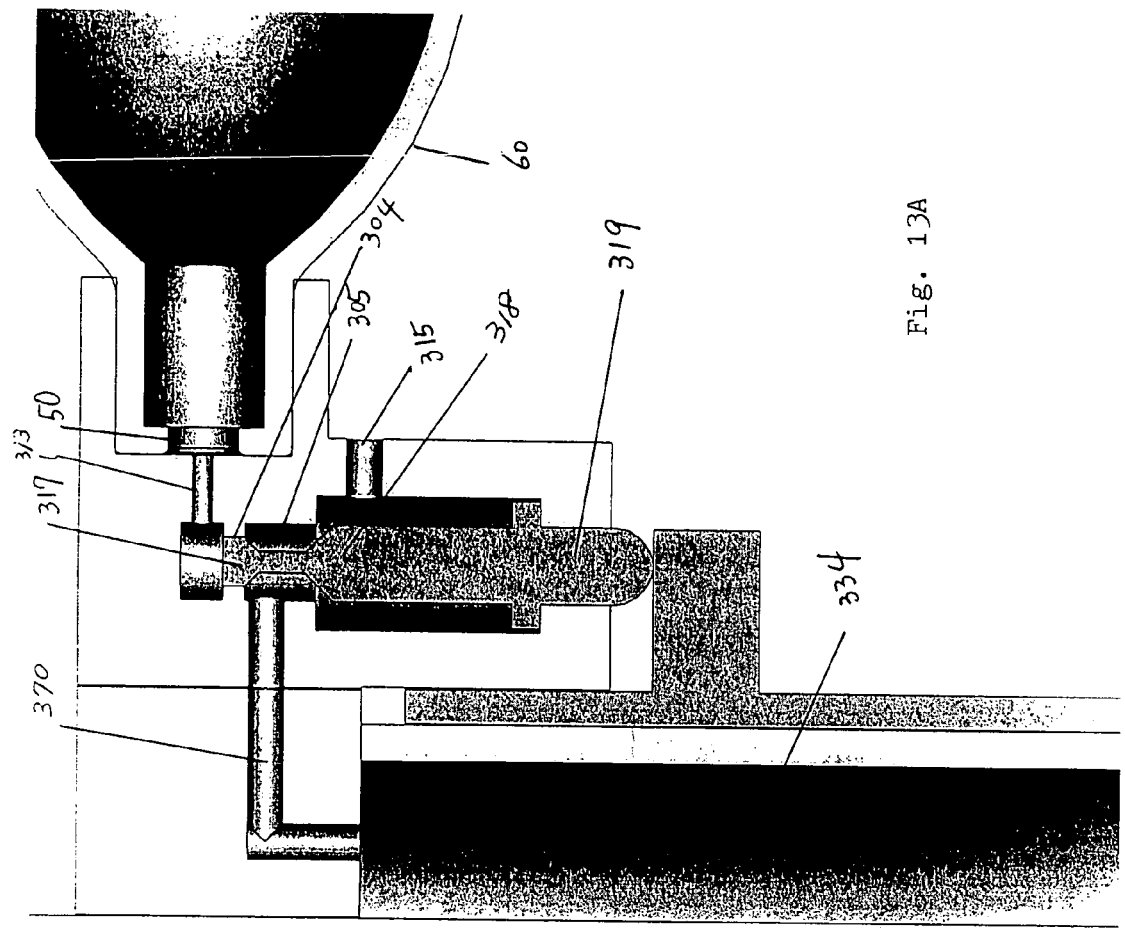
FIG. 13A is a perspective view illustrating the initial position (source valve is closed and vent valve is open to gas outlet port) for the operation of the third embodiment (at rest) for the power-assisted syringe illustrated by FIG. 10.
Figure 13A:
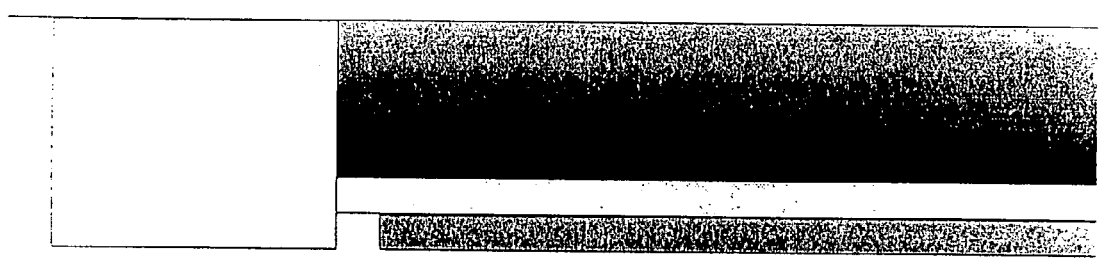
Figure 13B:
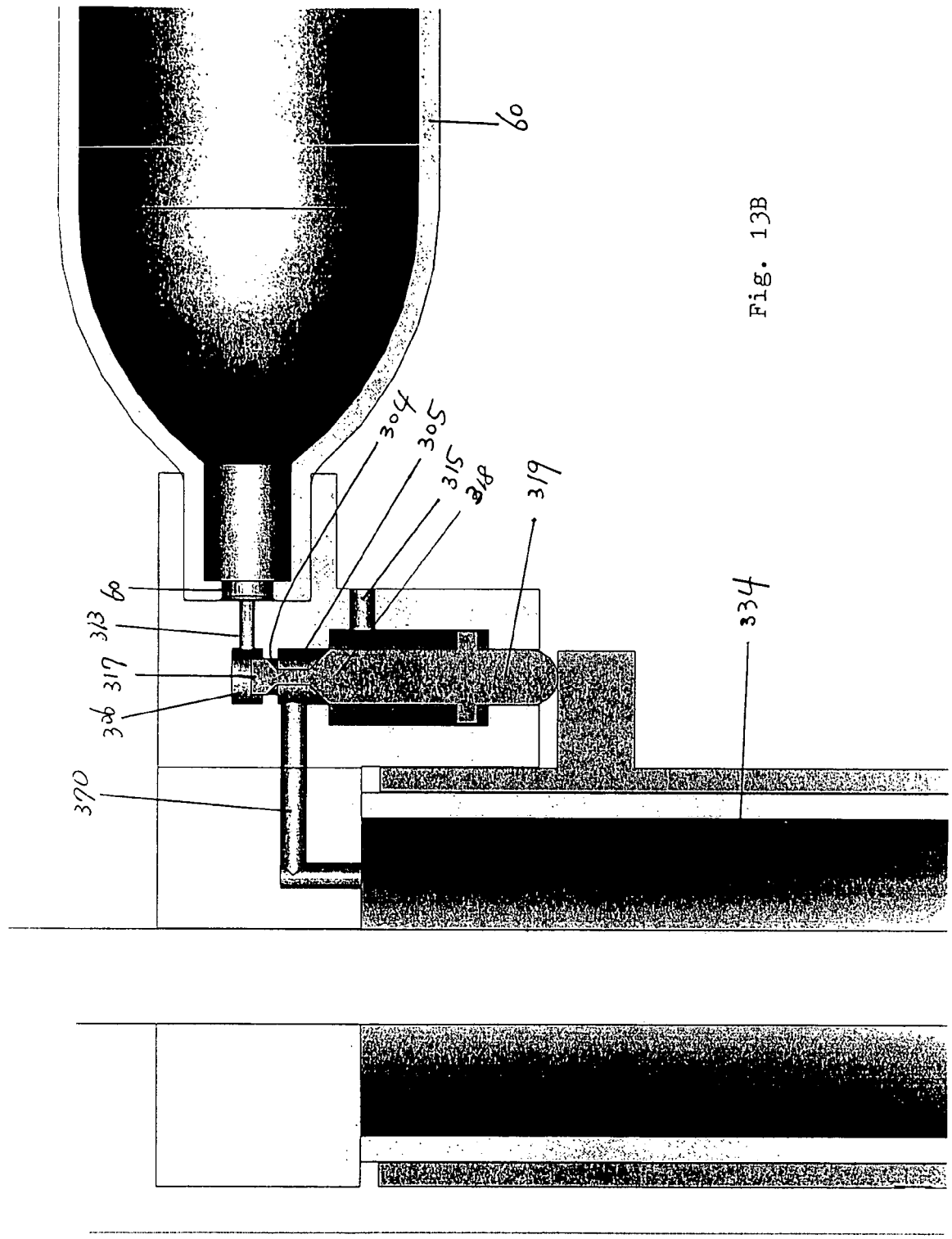
FIG. 13B is a perspective view illustrating a second position (source valve is still closed and vent valve is closed to gas outlet port) in the operation of the third embodiment (at the beginning of the squeezing force applied to the top of the valve housing against the slidable collar protrusion in contact with the engageable valve piston)) for the power-assisted syringe illustrated by FIG. 10.
Figure 13C:
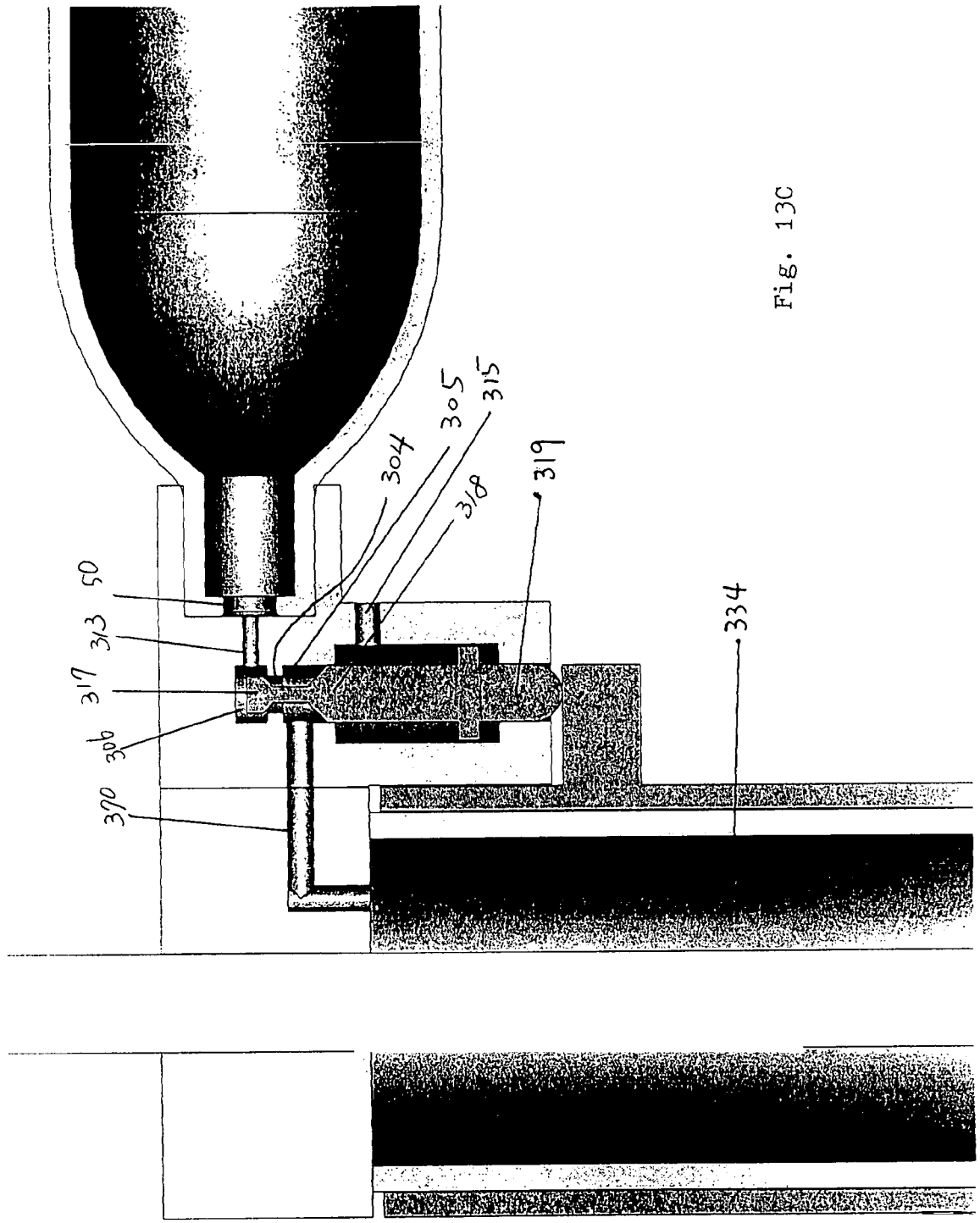
FIG. 13C is a perspective view illustrating a third position (source valve is about to open and vent valve remains closed to gas outlet port) in the operation of the third embodiment (the squeezing force continued to be applied to the top of the valve housing against the slidable collar protrusion) for the power-assisted syringe illustrated by FIG. 10.
Figure 13D:
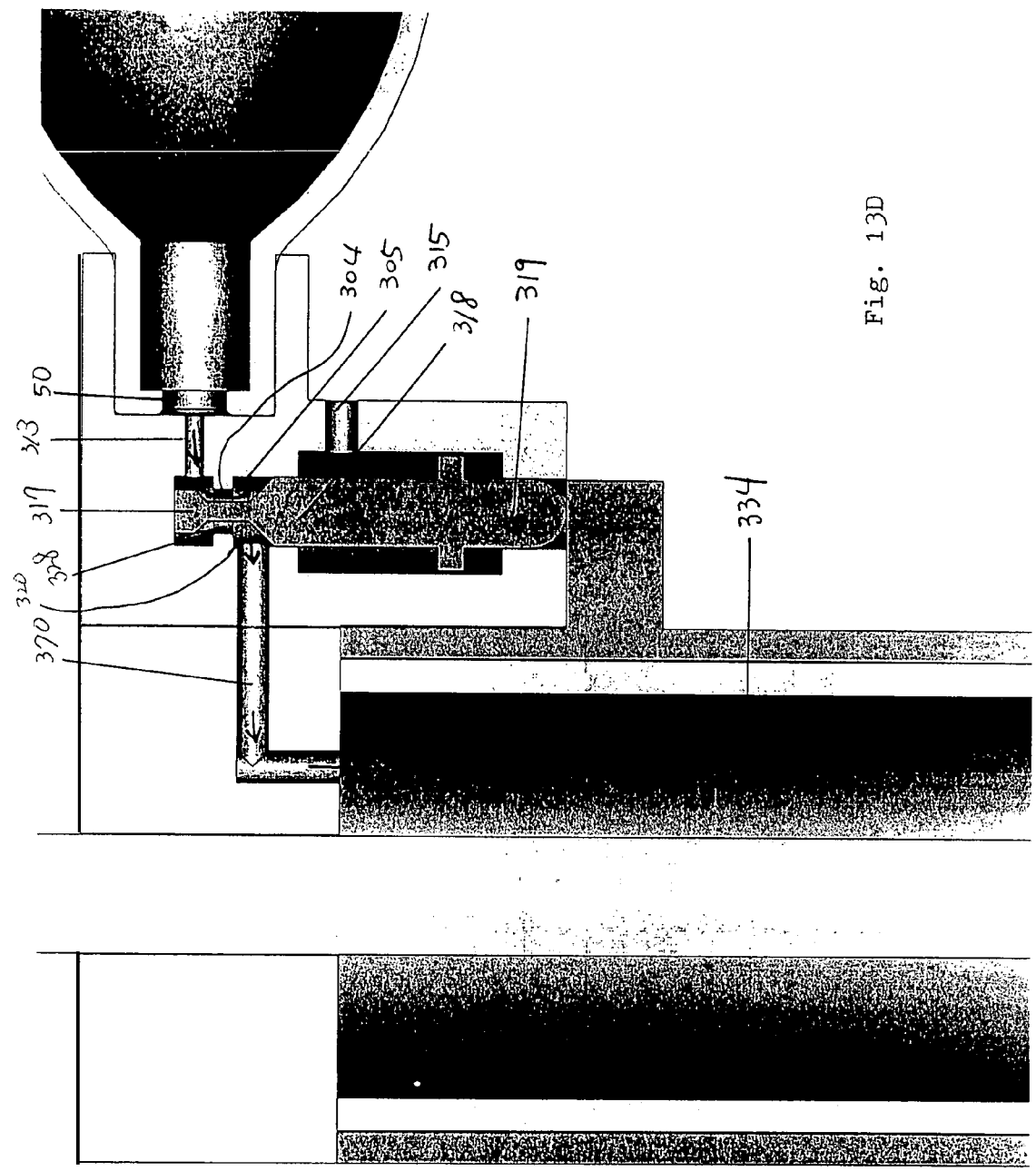
FIG. 13D is a perspective view illustrating a fourth position (source valve is open to gas inlet port and to the barrel access channel through the space (source port) between the source valve and source valve sealing surface so that gas moves from the gas source to barrel of syringe following arrows) of the operation of the third embodiment for the power-assisted syringe illustrated by FIG. 10.
Figure 13E:
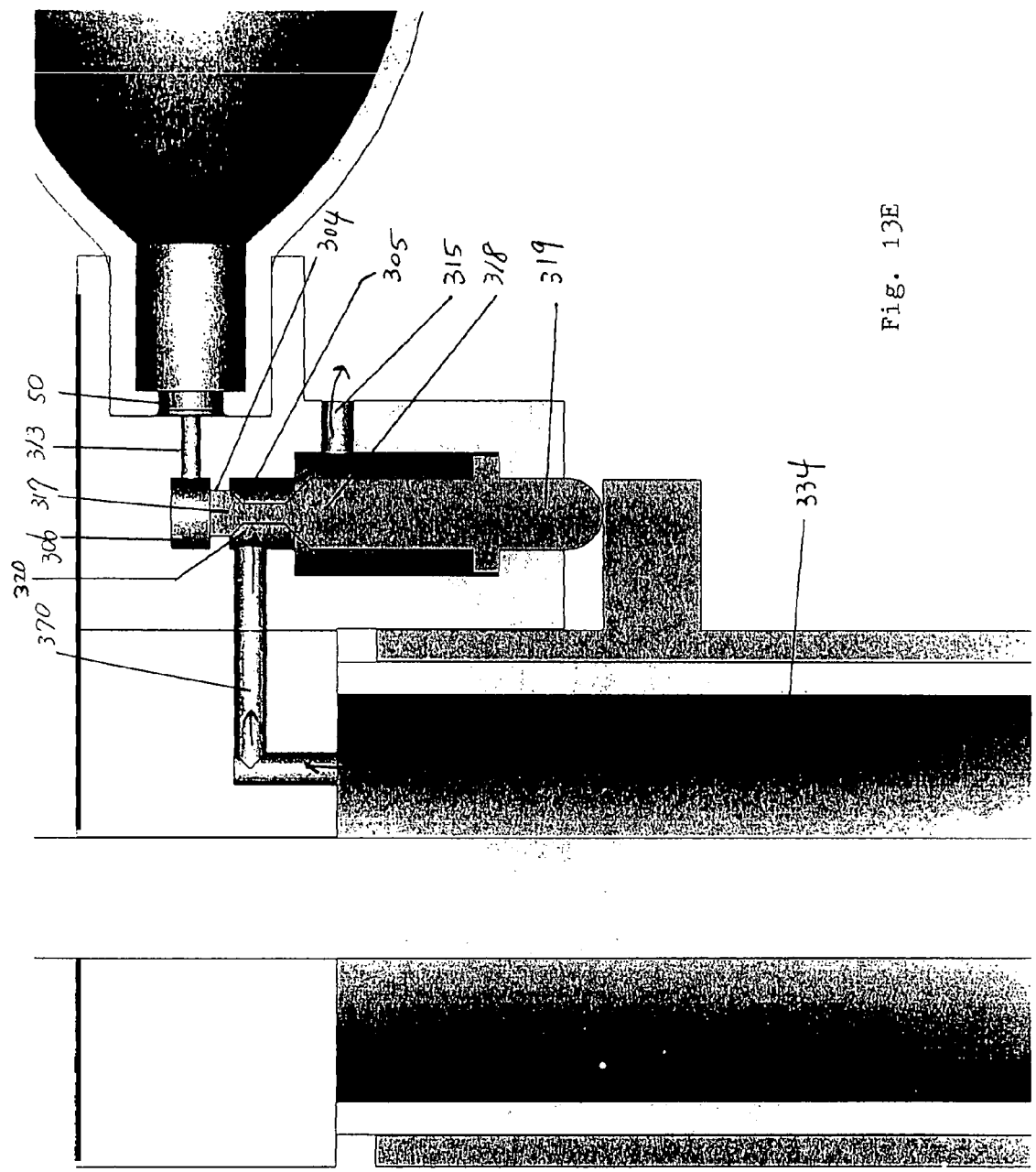
FIG. 13E is a perspective view illustrating a final position (returning to rest stage with source valve back to closed position and vent valve back to open position so that gas moves from barrel space to gas outlet port following the arrows) in the operation of the third embodiment for the power-assisted syringe illustrated by FIG. 10.
Figure 14:
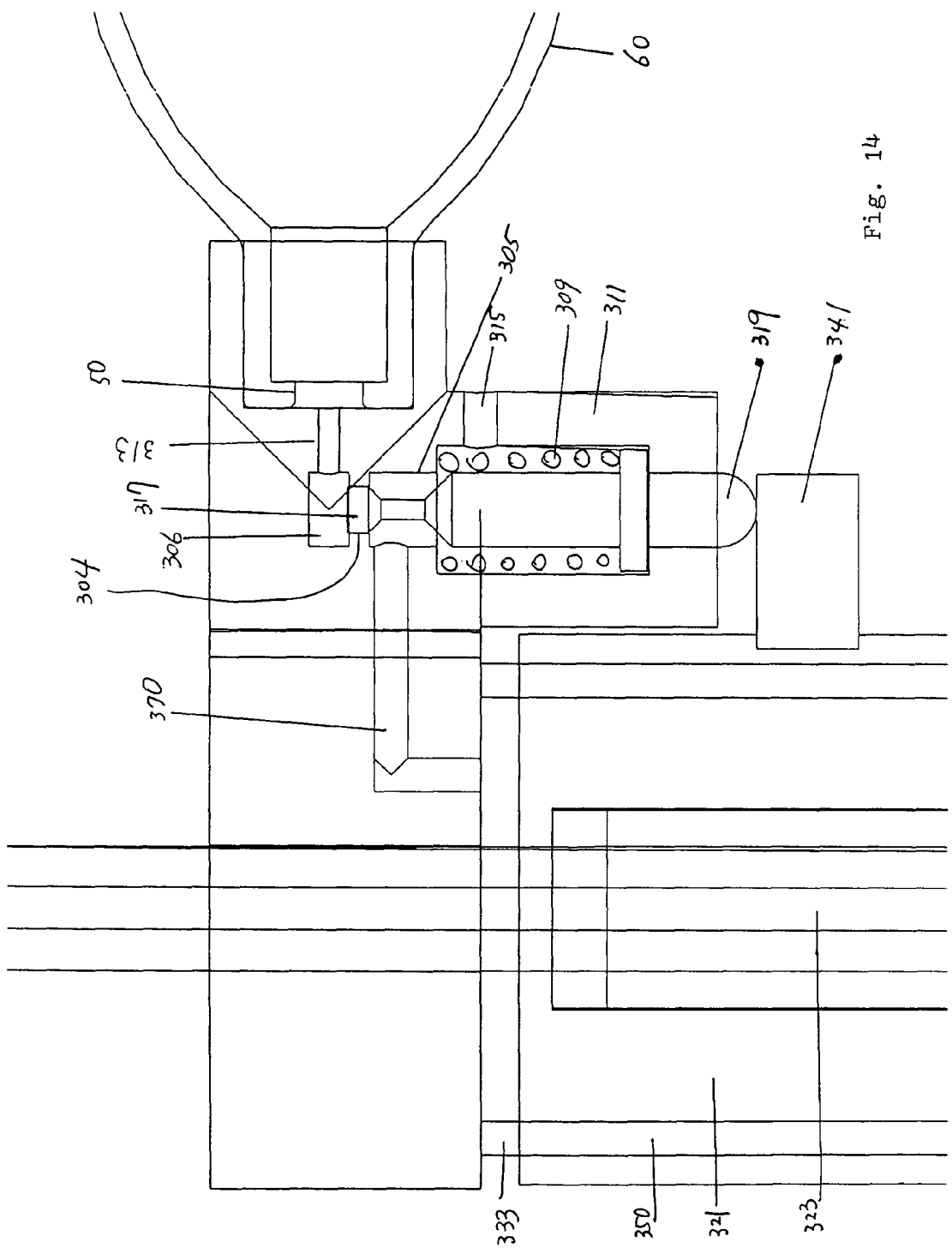
FIG. 14 shows detailed cross-sectional view of the third embodiment for the power-assisted syringe of FIG. 13A as an example.
Figure 15:
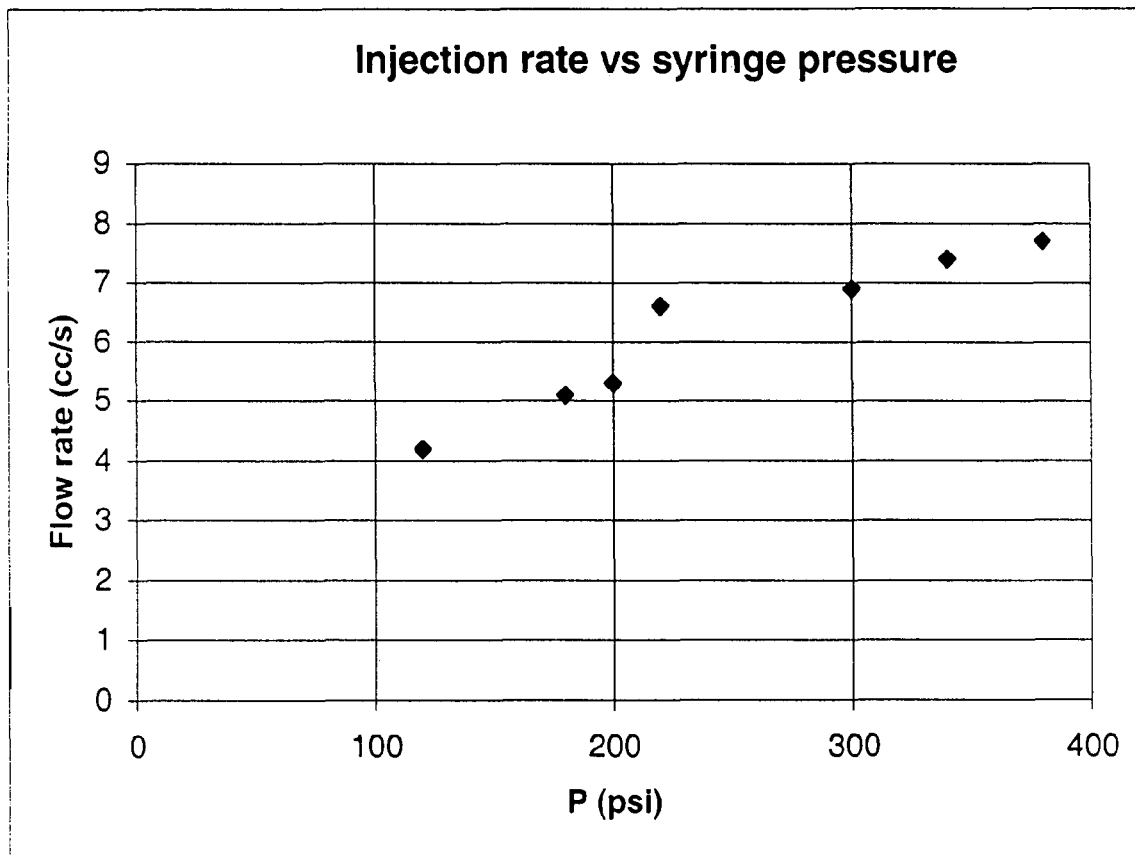
FIG. 15 is a graph showing injection rate vs. syringe pressure (proto-type power assisted syringe based on the first embodiment) using a 4 French (with 0.035-inch diameter lumen), 100 cm-long catheter.
Figure 16:
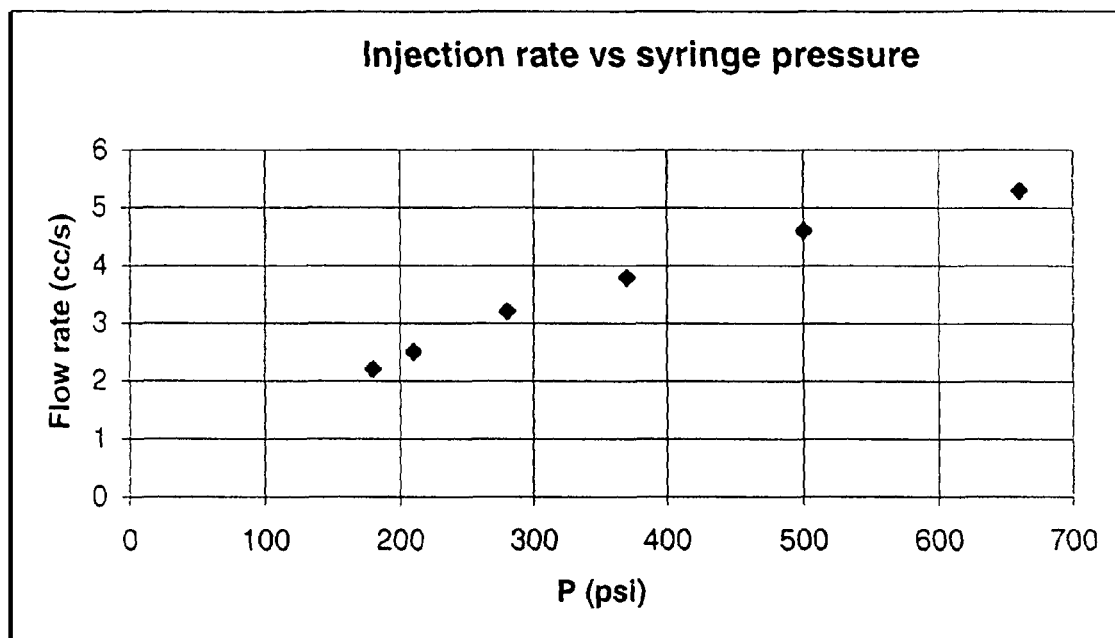
FIG. 16 is a graph showing injection rate vs. syringe pressure (proto-type power assisted syringe based on the first embodiment) using a 4 French (with 0.035 inch diameter lumen), 100 cm-long catheter when the flow resistance of the catheter was adjusted using a clamp.

FIGS. 10-14 shows that the sliding collar 340 has a protrusion 341 that can contact the valve assembly 310 upon application of an applied force. The valve assembly 310 contains a regulatory inlet and outlet valve construction (such as a needle valve) comprising an engageable valve piston 319 to control the source (inlet) valve 317 and vent (exhaust) valve 318. The regulatory valve structure is biased by at least one spring 309 in a position, such as illustrated by FIG. 14, at which the vent (exhaust) valve 318 is in the open position and the source (inlet) valve 317 is in the closed position.

FIGS. 13A-13F respectively show the operation of the power-assisted syringe and illustrate several stages of valve openings resulting from an operator applied force upon the valve housing 311. FIG. 13A shows the power-assisted syringe at the stage when no manual pressure or force is being applied to the valve housing 311 by the operator. FIG. 13A shows a perspective cross-section view of the plunger tube member 322, a syringe barrel access channel 370, the source (inlet) valve 317, and the vent (exhaust) valve 318 in their aligned positions within the interior of the valve housing 311 with respect to the gas source 60. As shown therein, the source (inlet) valve 317 and the vent (exhaust) valve 318 are seen in their aligned position; and one or more springs bias each of these regulatory valves in their respective closed and open positions when no operator force is applied.

Note that the source (inlet) valve 317 lies adjacent to and is in on-demand fluid flow communication with the gas inlet port 313; which in turn, is joined to and is in fluid flow communication with the gas source 60 (via the attachment means 50). Note also that the source (inlet) valve 317 lies adjacent to and is in on-demand fluid flow communication with the syringe barrel access channel 370; which in turn, is in fluid flow communication with the internal spatial volume (the lumen) 334 of the barrel assembly 330. In similar fashion, the vent (exhaust) valve 318 lies adjacent to and is in on-demand fluid flow communication with the gas vent port 315; and is also in on-demand fluid flow communication with the syringe barrel access channel 370.

Accordingly as described previously herein, the aligned placement and interaction of the source valve sealing surface 304 and the gas inlet port 313 with the source (inlet) valve 317 function in combination and collectively form the inlet valve regulating assembly. In a similar fashion, the vent (exhaust) valve 318 lies adjacent to the gas outlet port 315, which in turn, is in fluid flow communication with the ambient environment. In this manner, the aligned placement and interaction of the vent valve sealing surface 305 and the gas outlet port 315 with the vent (exhaust) valve 318 will function in combination and collectively form the outlet valve regulating assembly.

FIGS. 13A and 14 shows that the source (inlet) valve 317 is in the closed position (via its biased spring). Thus, the inlet valve regulating assembly is closed even while the gas inlet port 313 is unobstructed and in direct open communication with the gas source 60. In contrast, the vent (exhaust) valve 318 is seen as being in the open position (via its biased spring); and lies in open flow communication with both the gas vent port 315 and the syringe barrel access channel 370. In this manner, the internal spatial volume 334 of the barrel assembly 330 is accessed and is vented to the ambient environment by the outlet valve regulating assembly, while the inlet valve regulating assembly remains closed.

FIG. 13B illustrates the initial result of applying a hand-generated force to the top of the valve housing 311 against the collar protrusion 314. As shown therein, the top of the biased source (inlet) valve 317 is axially moved and is displaced upwards a short distance into the interior of inlet valve chamber 306; and the vent (exhaust) valve 318 moves into the initial contact with the vent (exhaust) valve sealing surface 305. This results in a partial obstruction and partial contact closure of the gas outlet port 315.

FIGS. 13C and 13D respectively further illustrate the operation of the third embodiment for the power-assisted syringe. As seen therein, as the manual force applied to the top of the valve housing 311 against the collar protrusion 341, is increased, the spring biased source (inlet) valve 317 is farther axially moved and is displaced ever-upwards a greater distance into the interior of the inlet valve chamber 306, such that it creates an annular space between the perimeter of the source (inlet) valve 317 and the source (inlet) valve sealing surface 304. Consequently, there is a free flow and unobstructed flow of gas from the source 60 to and through the space between the source (inlet) valve 317 and the source (inlet) valve sealing surface 304; and then into the syringe barrel access channel 370; and in turn, into the internal spatial volume 334 of the barrel assembly 330. Concomitantly and concurrently, the continued axial displacement of the vent (exhaust) valve 318 completely removes it from access to the gas outlet port 315. Thus, as the vent (exhaust) valve 318 becomes ever-more axially displaced, it makes full closure contact with the vent valve sealing surface 305; and this results in complete obstruction and direct contact closure of the gas outlet port 315.

Also as illustrated in FIG. 13D, as the manual force is increased, the close engagement of the valve piston 319 by the collar protrusion 341 closes the vent (exhaust) valve 318 and moves the source (inlet) valve 317 into its fully open position, i.e., without having contact with the source (inlet) valve sealing surface 304. Subsequently, the introduction and flow of pressurized gas (vapor pressure) 60 occurs through the hollow gas inlet channel (heat exchange passage) 313, the exposed source port 328 (space between the perimeter of the source (inlet) valve 317 and source valve sealing surface 304), the valve working volume 320 (the space between the vent valve sealing surface 305 and the vent (exhaust) valve 318), syringe barrel access channel 370, and into the barrel space 334 of the barrel 332 (see the arrows indicating passage of gas).

As illustrated in FIG. 13E, subsequently upon disengagement of the manual force, the converse occurs—i.e., the vent (exhaust) valve 318 is opened and the source (inlet) valve 317 is closed. The active pressure in the space between valves is connected to the barrel space 334. The gas flows from the barrel space 334 through the syringe barrel access channel 370, the valve working volume 320, the gas outlet port 315, and into the ambient environment (see arrows indicating flow passage of the gas), when the force previously applied to the top of the valve housing 11 is terminated—an event which occurs when the act of contrast medium injection is completed.

The engagement and disengagement of the operable valve piston is performed by a squeezing action of the operator to initiate and provide the gas power assist. In one embodiment of this structural design, there is an overlap position between the closing of the vent (exhaust) valve and the opening of the source (inlet) valve, as shown in FIG. 13C. This overlap results in dead band; but can be controlled at manufacture to any desired amount, for example 30 mils. Alternatively, this connection between the piston and valve housing can be a tapering design in which the overlap of the open and closed states of the source (inlet) and vent (exhaust) valves is performed by increasing flow resistance. Thus, instead of "infinite" resistance between clearly separated source (inlet) and vent (exhaust) valve open and closed states, a "finite" resistance is instituted and obtained between the open and closed states of the valves by transferring a gradually increasing flow resistance caused by the tapering of the piston and/or passages of the valve housing assembly. The configuration provides for smooth operation by an operator.

4. Other Formats, Features and Properties

Alternative Formats:

The present invention has been designed for simplicity so that the valve housing assembly controlling the power-assisted gas flow does not slide or move within either the plunger assembly or the barrel assembly. Thus, in one alternative embodiment comparable to the first embodiment described herein, the valve housing assembly is attached externally to the plunger assembly; and yet, in another alternative embodiment, the valve housing assembly is attached internally to the plunger assembly.

Furthermore, the valve housing assembly as whole can be a structural element which is rigidly attached to the plunger assembly. As an useful alternative, however, the valve housing assembly can also be flexibly and separately connected to and be in fluid communication with the plunger assembly; and, in this format, is attached in such a manner that the plunger assembly can move freely and independently from the valve housing assembly. For example, as shown by the third preferred embodiment, the valve housing assembly can be attached to the barrel assembly rather than to the plunger assembly. Also, in other formats utilizing the arrangement and design of the present invention, the valve housing assembly can be incorporated into any part of a component that transmits the squeezing force necessary to engage the engageable valve piston.

On-Demand Power Assistance:

In many embodiments, the present invention provides gas generated power assistance on-demand and only when desired by the operator. Thus, the use of power assistance is truly an optional feature, which can be turned on or off at will by a mechanical switch.

The power-assisted system may further comprise a hypsometer with a thermocouple, pressure transducer, capillary tube, thermistor, or the like, coupled to the barrel or plunger to determine a temperature and/or pressure of fluid in its lumen or space between them. This allows for accurate real time monitoring of variables (pressure or temperature) that effect the efficacy and safety of the system. An indicator system, such as a warning light or audio signal, may additionally be coupled to the thermocouple to provide a signal to an operator of the system when there is failure of the system such as leakage or overflow of gas.

In addition, signals from a pressure monitoring port and a thermocouple connector may be transmitted to the controller. This allows the use of a feedback control system for initiating, regulating, and halting the supply of pressurized fluid from fluid supply system. More specifically, the controller will often provide a control signal to the fluid supply system in response to signals from pressure monitoring port and/or thermocouple connector.

If desired, a fluid shutoff system can be optionally included to inhibit the flow of gas into the syringe in response to a pressure failure in the syringe—by a circuit connected to a shutoff valve. The circuit may be powered by a battery; and the battery may also be electrically coupled to a heater for heating the fluid supply therein to room temperature or warmer so as to enhance the fluid pressure and pressure performance.

The power-assisted syringe may further comprise at least one rupture disk molded into a proximal or distal part of the syringe. In some instances, it may be desirable to mold rupture discs into the body of the syringe to preclude such failures or prevent burst of the syringe. The gas supply can also be coupled with a gas pulse mode effecting the introduction of a pulse of gas pressure into the syringe;

Alternatively, as indicated in the preferred embodiments of the present invention, the syringe device can be designed to provide power assist only after a pre-chosen minimum force has been applied by hand. The magnitude of the minimum hand-generated force needed to activate the power assist for the syringe can be controlled by the resistance of the springs used to bias the regulators/valves in a position at which the gas inlet valve is closed and the gas vent valve is open. Such a structural arrangement and design allows the operator to inject contrast medium by hand in those situations where only minimal hand pressure is required and without needlessly wasting the gas power assist feature. For example, the gas power assist would not generally be needed if the contrast medium is injected back into a containment or storage unit.

III. Fabrication and Use of the Invention

Fabrication of a Power Assisted Syringe Device:

The power assisted syringe embodiments illustrated by the figures of the Drawing provided herewith are based upon preferred designs intended primarily for fabrication of metal components with automated or semi-automated machine tools. However, any commercially manufactured or salable products comprising an embodiment of the present power assisted syringe may also be based upon manufacturing designs that include injection-molded components. All such manufactured embodiments are therefore deemed to be within the spirit and encompassed by the scope of the present invention.

Also, while the invention described herein with its various components comprises a complete system for performing injection of medically useful fluids, it will be expressly understood that particular components or individual sets of components may be used as a part system, or as an add-on system, in similar, modified, or duplicated device arrangements for a variety of applications in medical as well as non-medical uses.

In addition, the syringe casing and fittings may comprise a variety of polymer and/or metallic materials including: nylon, polymide; PI polymide; peek polyetheretherketone; Kevlar; polyvinulidene fluoidie (PPS); graphite; polyethlene terephthalate (PET); polycarbonate (Glazing); PTFE; turfnol laminates; acetal delrin; acrylics; viton or polyurethane (for o-rings); metals and various metal alloys (stainless steel, aluminum, cobalt, titanium, nitinol, zinc, cadmium, gold, platinum, gold, copper, silver, bronze, nickel), boron nitride in a polyethylene (for better heat transfer); but may alternatively comprise any of a wide variety of materials.

In the exemplary embodiments described above, some portion of the fittings and accessories are off-the-shelf items which are sized and adapted to receive and open a standard, commercially available pressurized fluid cartridge. The casing and sealed components of the fitting may be fabricated by assembling and/or modifying components sold commercially by iSi Gmbh (located in Vienna, Austria); Leland Limited (South Plainfield, N.J.); and iSi North America (Fairfield, N.J.); but may alternatively comprise any of a wide variety of materials.

The Manner of Using the Present Invention:

The power assisted syringe comprising the present invention is simple and easy to use. For example, when a small amount of x-ray dye needs to be used in patients at high risk for renal failure, a short and gentle push of the plunger member will result in 1 to 2 cc of contrast bolus which rapidly traverses the blood vessel and produces a radiopaque image of excellent quality with minimal use of x-ray dye. This power-assisted syringe allows physicians more control during angiography while enhancing their pressure force power several fold.

Moreover, the use of a vapor pressure system to power and drive the plunger into and through the syringe barrel, along with the ability to use the fingers to grip the handle such as finger rings, enables the operator to generate syringe pressure forces up to 800 psi. The use of this power assisted syringe is advantageous over an electromechanical injector, because the gas-assisted syringe enables the operator to control the exact delivery of contrast medium, 0.1 to 60 ml, in real time as the vessel is visualized under fluoroscopy. In this manner, excellent quality images can be obtained while using a markedly reduced volume of contrast material and avoiding waste of the contrast material.

It will be noted and appreciated that the present invention does not require pressure force adjustment or calibration either before or during a medical procedure. Thus is there never any action or activity such as the adjustment of a pressure regulator valve. The power-assisted syringe device may therefore be used with a wide range and variety of catheters, catheter sizes, and catheter systems, each having its own and individual fluid flow resistance characteristics. No adjustment or calibration is required to use any of the conventionally known catheters in order to achieve a desired flow rate of fluid such as contrast medium. The present invention also allows for a fine adjustment of gas flow rate directly to control the contrast medium flow rate, as for example by using at least one needle valve.

Using a conventional $CO_2$ cartridge, a physician can perform approximately 20 to 30 injections of radiopaque contrast media with an 8 g cartridge over a 20-30 minute time period. If additional injections are needed, the empty cartridge can be quickly and easily removed (e.g., unscrewing, sliding, or grippling) from the syringe device and replaced with a full cartridge. Alternatively, larger canisters (such as up to 45 g in size) can be used with a power syringe, which accommodates the bigger size of the syringe and injection of contrast media in larger amount.

The design structure of the present invention also helps to reduce the waste of pressurized gas. In many embodiments, the pressurized gas is only utilized to assist in contrast fluid injection when a hand generated force is applied to move and distally displace the plunger assembly and the valve housing assembly with respect to the barrel assembly—i.e., only when the syringe is engaged to inject contrast medium into the blood vessel of the patient.

IV. Intended Uses and Applications

1. The present invention can be used for delivery of any fluid or flowing material to the cardiovascular system, gastrointestinal tract, biliary tract, genitourinary system, peritoneal cavity, thoracic cavity, spinal canal, ventricular system of the brain, or any other body cavity to facilitate their diagnostic and therapeutic medical and surgical procedures—with or without fluoroscopic, endoscopic, angioscopic, ultrasonic, MRI (magnetic resonance imaging) or laparoscopic visualization and guidance.

2. The power-assisted delivery system of the present invention can also be used for delivery of liquids, flowing solids or semi-solids (gels) such as medications, thrombolytic drugs, stem cells, genes, DNA and RNA fragments, micro-organism, vaccines, and surgical glues or cements, or a mixture which uses one or more of them in combination. These materials are often needed during diagnostic or therapeutic medical, veterinary, biological, genetic, and dental procedures (i.e., angiography, veterbroplasty, and interventional procedures). The power-assisted delivery system can also be used for inflating balloons during angioplasties, cyro-angioplasty (cryoplasty), and valvuloplasty; and for stent expansion and deployment for the various blood vessels and organs in normal or abnormal conditions.

3. In addition to the foregoing, the power-assisted delivery system can also be used for dissecting tissue planes; for removal of stones or foreign bodies from the body; for delivery of oxygen or other gaseous materials via the airway or other routes for resuscitation or anesthesia of the patients; for distending the stomach or the intestine; for creating a jet stream or Venturi effect with forceful and rapid injection of fluid sufficient to achieve certain diagnostic and therapeutic effect such as thrombolytic/thrombectomy procedures and other diagnostic and therapeutic procedures using ultrasonic, X-ray, magnetic, Piezoelectric, nuclear or laser energy and devices; for transdermal or trans-organ delivery of medication; for transvascular/trans-endothelial/trans-adventitial or transcardiac/trans-endocardial/trans-myocardial/trans-epicardial delivery of drugs, genetic/cellular material, growth factors (VGEF) or anti-growth factors, genetic and cellular materials, micro-organic materials, vaccines, fluid or medican devices; and for injecting fluid at normal, cold, warm or hot temperature into any empty anatomic space or other cavity in the living body.

4. Furthermore, while the invention described herein comprises a complete system intended primarily for injection of fluids into a living subject, it is expressly understood that the present invention may also be employed as part of a complete system in a variety of different applications. As merely one example, a conventional off-the-shelf syringe pre-filled with contrast medium or other materials used in medical diagnosis or treatment may be used in conjunction and in combination with the power-assisted syringe described herein. The combination use of the instant power-assisted syringe with an off-the-shelf syringe would provide the operator with benefits provided by a minor modification of the system, such as a piggy-back or co-axial syringe joined with and to the power-assisted syringe configuration as a single multi-part system.

5. In another system variation using the present invention, an apparatus is provided to inject gas in a controlled manner into an anatomic body space (such as blood vessels) during diagnostic and therapeutic procedures. The apparatus has a fluid containing cylinder, which provides pressurized gas or a two-phase mixture of pressurized gas and cold liquid. Suitable gas sources will preferably be non-toxic and include liquid carbon dioxide ($CO_2$), liquid nitrous oxide ($N_2O$), liquid oxygen ($O_2$), a fluorocarbon such as $AZ_{50}$.TM. (sold by Genetron of Morristown, N.J.), liquid nitrogen ($N_2$), and/or a variety of alternative pressurized liquid gases.

As these fluids are at quite high pressures within cartridge, they may be in the form of a liquid or gas/liquid mixture, even at room temperature. The canister will typically comprise a metallic structure. Suitable cartridges will hold quantities of pressurized gas that are sufficient to perform conventional angiographic and other medical procedures. Cartridges might have volumes between 2 cc and 100 cc (depending in part on the flash expansion temperatures of the fluid), and may contain between about 5 g and 45 g of pressurized fluid. A typical cartridge might contain a quantity of $CO_2$ or $N_2O$ in a range from about 5 ml to about 20 ml, ideally having about a 10 ml or 8 grams of $CO_2$ or $N_2O$ liquid at about 750 psi. and may contain between about 5 g and 30 g of pressurized fluid. A typical cartridge might contain a quantity of $N_2O$ in a range from about 5 ml to about 20 ml, ideally having about a 10 ml or 8 grams of $N_2O$ liquid at about 750 psi. Conveniently, some of such cartridges are commercially available for use in whipped cream dispensers. As explained below, canisters may be at room temperature or even chilled, but will preferably be warmed gently prior to use. The canister can be heated using a 20 watt to 50 watt, preferably 40 watt, Kapton heater film.

6. In all instances, the present invention provides for a power-assisted injection of fluid as a contrast medium into and through a previously placed delivery catheter. The fluid is delivered using a gas (e.g., $CO_2$) or other cold liquid ($N_2O$, $N_2$, Fluorocarbon, $O_2$, etc) which has a specific vapor pressure at a known temperature. Such power-assist provide syringe pressure force great enough to deliver the desired volume and flow rate of fluid material to the catheter, the implanted tubes or other delivery articles. The power-assist means may utilize any of various additional power sources resulting in various embodiments for power-assisted injection. Such embodiments further described herein use power sources which include (i) a force amplifier, (ii) a gas spring, (iii) a mechanical spring, (iv) electric motor, (v) pneumatic motor, (vi) magnetic motor, (vii) solar or other light power, (viii) thermal power and (ix) a standard contrast injector or the like.

V. A Particularly Valuable Trait and Desirable Feature

The present invention provides a characteristic "look and feel" of a conventional manually operated syringe, characteristics with which those ordinarily skilled in the art have become accustomed. This "look and feel" characteristic is not a superficial or simplistic feature; rather, this characteristic is important and integral to providing critical feedback parameters and is necessary to achieve an acceptable image quality and the safety of the procedure.

The feedback parameters used to control the flow rate include tactile components and visual components; and these are essential perceptions used by the operator to control the flow rate of contrast medium in real time fashion. It is these feedback parameters which allow the operator to interpret whether contrast medium is being injected at the proper rate. Moreover, if and when a change in contrast medium flow rate is deemed to be necessary, the operator then appropriately adjusts the pressure force applied to the syringe plunger in real time.

The two tactile feedback parameters are motion and force. The motion component is provided by the relative rate of finger motion as syringe volume is decreased. The force component is the result of having to provide increased force to achieve a proportional increase in flow rate. This is empirically demonstrated by the data of Tables 1 and 2 below and is graphically illustrated by FIGS. 15 and 16 respectively.

The visual feedback component may be the result of either seeing the plunger moving within the syringe barrel at a particular speed or seeing a fluoroscopic image with contrast density yielding a particular opacity. All of these feedback parameters are considered to be valuable aids by the operator and are constantly used to adjust the force applied to the plunger to achieve the desired image quality during diagnostic or therapeutic medical procedures.

TABLE 1

A 4 Fr (0.035-inch diameter lumen), 100-cm catheter was used to collect data. Water was injected through the catheter at various flow rates. The syringe was filled with 12 cc for each data point. The flow rates were as near constant as could be obtained by applying constant force to the plunger; in other words, no attempt was made to adjust the flow rate to obtain a desired pressure or flow rate. The data is shown below and by FIG. 15.

| Time (sec) | Syringe Pressur | Supply Pressure | Volume flow (cc/s) |
|---|---|---|---|
| 5.38 | Low | 780 | 2.2 |
| 2.87 | 120 | 790 | 4.2 |
| 1.56 | 380 | 790 | 7.7 |
| 2.37 | 180 | 790 | 5.1 |
| 2.25 | 200 | 790 | 5.3 |
| 1.82 | 220 | 790 | 6.6 |
| 1.75 | 300 | 770 | 6.9 |
| 1.63 | 340 | 770 | 7.4 |

TABLE 2

The flow resistance of the catheter was then adjusted using a clamp. The data is shown below and in FIG. 16. Note that even the data point at 660 psi was obtained without applying excessive force.

| Time (sec | Syringe Pressur | Supply Pressur | Volume flow (cc/s) |
|---|---|---|---|
| 5.41 | 180 | 800 | 2.2 |
| 4.78 | 210 | 800 | 2.5 |
| 3.15 | 370 | 800 | 3.8 |
| 2.60 | 500 | 800 | 4.6 |
| 2.28 | 660 | 790 | 5.3 |
| 3.75 | 280 | 790 | 3.2 |

VI. Major Advantages and Particular Benefits of the Present Invention

1. The heat exchange system integrated in the valve housing system allows the elimination of pressure regulator and provides major advantages such as compactness and portability. The power assist syringe device can be used with the same conventionally known manifold system as the traditional manual syringe. Furthermore, it is the first device which is a hand-held power syringe controllable by a single human hand.

2. The various embodiments of the device are simple designs having extra-safety features that allow any leaked gas to be vented through the internal lumen of the plunger before it gets into the system of the patient. The device is also compatible with various pressurized gases such as $CO_2$, $N_2O$, $N_2$, Fluorocarbon and the like.

3. This versatile device provides the ease of use found in manual injector systems while permitting high quality imaging of structures requiring larger volume injections.

4. The power-assisted syringe facilitates the use of smaller catheters in a variety of medical, radiological, and surgical procedures. The smaller sized catheters and reduced use of contrast media reduce the risks associated with the medical procedures such as renal or heart failure and bleeding from the catheter-access artery, and markedly improve patient comfort, thereby allowing for early ambulation and decreased cost.

5. Though only a small volume of contrast medium may be needed, the power-assisted syringe can accelerate the contrast column rapidly to achieve adequate flow and thereby obtain excellent opaque (with radio-opaque contrast medium) or lucent (with gaseous contrast) images. This is achieved without causing blood vessel damage or producing excessive pressures within the cardiovascular system. This ability to accelerate the contrast column rapidly and to use smaller material volumes for each injection allows the operator to use substantially less contrast medium.

6. In its preferred embodiments, the present invention is a hand-held, fully self-contained, power-assisted syringe device capable of providing sufficient pressure force on-demand and is able to inject contrast medium through a catheter at any desired flow rate. Because the power assisted syringe is fully self contained, no remote pressurized gas source is required; and this feature eliminates a sterile/non-sterile interface between the operator and the remote gas source. Moreover, being fully self-contained also eliminates the conventionally required adjustment of a pressure regulator valve at the pressurized gas source by separate personnel. The power-assisted syringe is designed for full operator control with a single hand-manual operation.

7. The present invention is made fully self contained by integrating a miniature pressurized-fluid supply cylinder directly into the syringe device. This aspect of the invention allows the device to be pre-packaged sterile for use by the operator in a manner compatible with a conventional syringe. This sterilization of the invention is possible as a result of an improved valve system internal to the device which provides the operator complete control over the contrast flow rate without pre-adjustment or calibration of the device, and eliminates any need for a pressure regulator valve.

8. The present invention addresses and improves the problems of large dead band zones and the feeling of stepped control by using a source and/or vent valve(s) that adjusts the cross-sectional area for flow in a continuously variable manner, such as a needle valve. Such a valve substantially reduces the dead band zone associated with increasing or decreasing the flow rate of contrast. Using a continuously variable valve also eliminates the operators sensation of stepped flow, thereby providing a sensation of flow rate control comparable to a conventional syringe.

9. The power-assisted syringe is not only able to deliver the required pressures (up to 800 psi) safely but leaves full control with the operator. The availability of the power-assisted syringe will enable operators to obtain improved quality of angiographic studies using a new torquable 4 to 5-Fr catheter (which requires injection pressure up to 500 psi for delivery of x-ray dye at a rate of 5 cc/sec); and allow cardiac catheterization and other procedures to expand rapidly as an outpatient procedure, since the early ambulation of the patients is possible with fewer access-site complications. Most operators would also be more comfortable performing coronary or other angiographic procedures from the smaller-sized arterial routes, such as radial route, if it were needed.

10. The power-assisted syringe device according to the present invention will be useful for various medical procedures in summary as follows:

(a) Cardiology: coronary angiography, coronary interventions, ventriculography, electrophysiology, gene therapy, drug delivery, placement of cardiac and coronary devices, displacement of blood during medical procedures to facilitate endovascular angioscopy, laser instrumentation, and ultrasonography such as optical coherence tomography.

(b) Radiology, Aortic, caval, pulmonary, carotid, renal, visceral and peripheral vascular imaging and interventions. Use in CT, MRI for injection of contrast agents, intraoperative procedures such as aortic stent-graft procedures; stent delivery; embolization coil delivery; thrombolytic agent delivery; delivery of drug or gene; cooling of body, blood vessel, organ, tumor, or blood; delivery or injection of gas into the vessel, gastrointestinal tract, heart, or ventricle of brain.

(c) Other fields: facilitating endoscopic procedures, angioscopic procedures, laparoscopic procedure, ENT and eye procedures, and dermatological procedures, with trans-luminal, intra-cavity or percutaneous delivery of drugs or devices, and facilitating infusion or injection of oxygen into air way or other part of body or organ to promote oxygenation and resuscitation of the patients, and facilitating cryo-surgery with delivery of cryogenic fluids.

(d) Cleaning of medical or other devices such as optic systems, computer system, camera, and display devices.

(e) During laser procedures, MRI, CT and ultrasonic procedures; ablation of tumor or treatment of tumor by infusion of fluid, drug, genetic/cellular material or gas via transdermal or trans-organic or trans-luminal or extra-luminal routes.

(f) Dental procedures involved in high speed injection of fluid, injection of viscous material or semi-solid materials such as cement or glue.

(g) Inflation for medical or non-medical balloons including angioplasty balloon catheter or cryo-angioplasty balloon catheter.

(h) Inflation of tires of automobiles or bi, tri-cycles.

(i) Water gun (j) Painting gun (k) Gun for shooting medical, non-medical, military, defence or toy materials such as metal, plastic, steam, gas, repellent material for insect or animals.

(l) Spraying for medical, non-medical, military or defence materials

While the invention has been described in with what is presently considered to be the most practical and preferred embodiments, it is to be understood that the scope of the instant invention is not to be limited to the disclosed embodiments. Many other embodiments of the invention will be apparent to those skilled in the art from the Specification or the practice of the invention as disclosed herein. It is therefore intended that the Specification and described embodiments be considered as merely illustrative and exemplary, with the true scope and spirit of the invention being stated only by the claims appended hereto.

The invention claimed is:

1. A portable, self-contained and hand-held power assisted syringe suitable for the injection of viscose liquids or gases into small bore diagnostic catheters and small guiding catheter systems, said power assisted syringe comprising:

a barrel assembly having proximal and distal ends and an internal spatial volume for containing and delivery of a fluid material;

a nozzle connected to said distal end of said barrel assembly for the ejection of fluid material contained within said internal spatial volume of said barrel assembly;

a hand operable plunger assembly comprising a plunger tube member which has an elongated hollow channel extending over its length, at least one aperture in said plunger tube member which provides fluid flow communication between said hollow channel and said internal spatial volume of said barrel assembly, and a plunger plate which is joined to said plunger tube member and is slidably disposed within said internal spatial volume of said barrel assembly;

a manually controlled valve housing assembly comprising a source valve and a vent valve which can be opened and closed repeatedly at will, said valve housing assembly being in on-demand fluid flow communication with said hollow channel of said plunger tube member of said plunger assembly, being able to receive pressurized gas on-demand from a portable source, and being able to regulate and deliver said received pressurized gas at variable flow rates on-demand to said hollow channel in said plunger tube member of said plunger assembly;

manual operating means by which to apply a hand-generated force to said plunger assembly; and means for attaching a portable source of pressurized gas to said valve housing assembly such that a portable source of pressurized gas can be attached and thereby provide pressurized gas to said valve housing assembly at a pressure sufficient for the injection of viscose liquids or gases into small bore diagnostic catheters and small guiding catheter systems.

2. A portable, self-contained and hand-held power assisted syringe suitable for the injection of viscose liquids or gases into small bore diagnostic catheters and small guiding catheter systems, said power assisted syringe comprising:

a barrel assembly having proximal and distal ends and an internal spatial volume for containing and delivery of a fluid material;

a nozzle connected to said distal end of said barrel assembly for the ejection of fluid material contained within said internal spatial volume of said barrel assembly;

a hand operable plunger assembly comprising a plunger tube member which has an elongated hollow channel extending over its length, at least one aperture in said plunger tube member which provides fluid flow communication between said hollow channel and said internal spatial volume of said barrel assembly, and a plunger plate which is joined to said plunger tube member and is slidably disposed within said hollow channel in said plunger tube member of said barrel assembly;

a manually controlled valve housing assembly comprising a source valve and a vent valve which can be opened and closed repeatedly at will, said valve housing assembly being in on-demand fluid flow communication with said hollow channel of said plunger tube member of said plunger assembly, being able to receive pressurized gas from a portable source, and being able to regulate and deliver said received pressurized gas at variable flow rates on-demand to said hollow channel in said plunger tube member of said plunger assembly;

manual operating means by which to apply a hand-generated force to said plunger assembly;

means for attaching a portable source of pressurized gas to said valve housing assembly; and a portable source of pressurized gas in fluid flow communication with and providing pressurized gas to said valve housing assembly at a pressure sufficient for the injection of viscose liquids or gases into small bore diagnostic catheters and small guiding catheter systems.

3. The power assisted syringe as recited by claim 1 or 2 further comprising a gas inlet port and a gas vent port within said valve housing assembly.

4. The power assisted syringe as recited by claim 1 or 2 further comprising a heat exchanger joined to said source valve in said valve housing assembly.

5. The power assisted syringe as recited by claim 4 wherein said heat exchanger is incorporated into said valve housing assembly such that said source valve and said heat exchanger constitute an integral unit.

6. The power assisted syringe as recited by claim 1 or 2 wherein said source of pressurized gas is a miniature canister.

7. The power assisted syringe as recited by claim 6 wherein said source of pressurized gas is attached to said valve housing assembly via a threaded fitting.

8. The power assisted syringe as recited by claim 1 or 2 wherein said valve housing assembly directs and delivers pressurized gas to said plunger assembly when said plunger assembly is moved distally.

9. The power assisted syringe as recited by claim 1 or 2 wherein said valve housing assembly further comprises: a gas source regulator valve to receive pressurized gas from said source; and a gas vent regulator valve to vent gas from said barrel assembly.

10. The power assisted syringe as recited by claim 9 wherein said gas source regulator and said gas vent regulator are needle valves.

11. The power assisted syringe as recited by claim 9 wherein said gas source regulator valve and said gas vent regulator valve are not needle valves.

12. The power assisted syringe as recited by claim 1 or 2 further comprising a collar slidably mounted on said barrel assembly, wherein said collar is attached to said manual operating means.

13. The power assisted syringe as recited by claim 12 wherein said valve housing comprises a needle valve assembly, and wherein said needle valve assembly comprises an engageable valve piston to control delivery of said pressurized gas to said plunger assembly when said collar engages said engageable valve piston upon application of said force to said manual operation means.

14. The power assisted syringe as recited by claim 12 wherein said valve housing assembly comprises at least one spring biased valve to control delivery of pressurized gas to said plunger assembly.

15. The power assisted syringe as recited by claim 1 or 2 wherein said the valve housing assembly comprises a heat exchanger and a spring biased valve in combination.

16. The power assisted syringe as recited by claim 1 or 2 wherein said fluid material to be delivered is a radiopaque contrast medium.

17. The power assisted syringe as recited by claim 1 or 2 wherein said plunger assembly comprises a plunger member having an internal hollow channel able to receive pressurized gas from said valve housing assembly.

18. The power assisted syringe as recited by claim 1 or 2 wherein said plunger assembly comprises means for venting excessive gas pressure force.

\* \* \* \* \*